United States Patent [19]
Brugnara et al.

[11] Patent Number: 6,028,103
[45] Date of Patent: Feb. 22, 2000

[54] TRIARYL METHANE COMPOUNDS AND ANALOGUES THEREOF USEFUL FOR THE TREATMENT OR PREVENTION OF SICKLE CELL DISEASE OR DISEASES CHARACTERIZED BY ABNORMAL CELL PROLIFERATION

[75] Inventors: Carlo Brugnara, Newton Highlands; Jose Halperin, Brookline; Emile M. Bellot, Jr., Beverly; Mark Froimowitz, Newton Centre; Richard John Lombardy, Waltham; John J. Clifford, Bedford, all of Mass.; Ying-Duo Gao, Neshanic Station, N.J.; Reem M. Haidar, Malden, Mass.; Eugene W. Kelleher, Somerville, Mass.; Falguni M. Kher, Chelmsford, Mass.; Adel M. Moussa, Burlington, Mass.; Yesh P. Sachdeva, Concord, Mass.; Minghua Sun, Cambridge, Mass.; Heather N. Taft, Littleton, Mass.

[73] Assignees: Children's Medical Center Corporation, Boston, Mass.; Ion Pharmaceuticals, Inc., New York, N.Y.

[21] Appl. No.: 08/822,550

[22] Filed: Mar. 19, 1997

Related U.S. Application Data

[63] Continuation-in-part of application No. 08/618,952, Mar. 20, 1996, and a continuation-in-part of application No. 08/618,760, Mar. 20, 1996, each is a continuation-in-part of application No.08/307,874.

[51] Int. Cl.⁷ .......................... A61K 31/28; C07C 255/04
[52] U.S. Cl. .......................... 514/492; 558/401; 558/405; 558/407; 514/319; 514/358; 514/410; 514/183; 552/101; 552/100; 552/105; 556/489; 560/312; 564/316
[58] Field of Search ................................ 558/401, 405, 558/407; 517/183, 410, 107, 492

[56] References Cited

U.S. PATENT DOCUMENTS

| | | |
|---|---|---|
| 4,006,023 | 2/1977 | McLaughlin et al. . |
| 4,551,526 | 11/1985 | Mai et al. ................................ 544/163 |
| 4,806,685 | 2/1989 | Abraham et al. . |
| 5,273,992 | 12/1993 | Brugnara et al. . |
| 5,358,959 | 10/1994 | Halperin et al. . |
| 5,430,062 | 7/1995 | Cushman et al. . |

FOREIGN PATENT DOCUMENTS

| | | |
|---|---|---|
| 0 323 740 | 7/1989 | European Pat. Off. . |
| 0 583 665 A2 | 2/1994 | European Pat. Off. . |
| 05 58894 | 3/1993 | Japan . |
| WO 95/26720 | 10/1995 | WIPO . |
| WO 96/08240 | 3/1996 | WIPO . |
| WO 96/08242 | 3/1996 | WIPO . |
| WO 96/36631 | 11/1996 | WIPO . |

OTHER PUBLICATIONS

Aldrich Catalog, 1994–1995, Compounds 13,484–8; T8,380–1; 10,130–3; D21,320–9; 32,543–0; 35,890–8; T8,160–4; 25,657–9; T8,470–0; T8,417–7; T8,360–7; S36, 533–5; S50,949–3; 37,411–3; 37,152–1; 30,151–5; 27,520–4; 34,182–7; 35,889–4; S84,240–0; S79,226–8; 27,519–0; S64,640–7; S81,477–6; 36,005–8; S70,627–2; S34,966–6; S87,739–5; 11,500–2;S 83,881–0; S58,110–0; 21,560–0; S91,408–8; S60,147–0; S83,571–4; S82,654–5; S8,388–2; S94,371–1; S87,649–6; S83,719–9; S83,042–9; S82,162–4; S81,468–7; S82,290–6; S79,387.
Ando and Ikeno, 1979, *Tetrahedron Lett.* 51:4941–4942.
Bartroli et al., 1992, *Arzneim–Forsch./Drug Res.* 42:832–835.
Benjamin et al., 1986, *Blood* 67:1442–1447.
Benzaquen et al., 1995, *Nature Medicine* 1:534–540.
Berkowitz and Orringer, 1984, *Am. J. Hematol.* 17:217–223.
Beutler and West, 1976, *J. Lab. Clin. Med.* 88:328–333.
Bontems et al., 1992, *Biochemistry* 31:7756–7764.
Brugnara, 1995, Advanced Course and International Symposium on Membrane Transports and Channels: Program and Abstracts Lecture 34.
Brugnara et al., 1993, *J. Clin. Invest.* 92:520–526.
Brugnara et al., 1993, *J. Biol. Chem.* 268(12):8760–8768.
Brugnara et al., 1994, *Blood* (220a):865.
Brugnara et al., 1995, *JPET* 273:266–272.
Brugnara et al., 1995, The 20th Annual Meeting of the National Sickle Cell Program, p. 138.
Brugnara et al., 1996, *J. Clin. Invest.* 97(5):1227–1234.
Burgess and Bodey, 1972, *Antimicrobial Agents and Chemotherapy* 2(6):423–426.
Byers et al., 1993, *Melanoma Res.* 3:247–253.
Carter et al., 1994, *J. Am. Coll. Cardiol.* 24(5):1398–1405.
Charache and Walker, 1981, *Blood* 58:892–896.
Charache et al., 1995, *N. Engl. J. Med.* 332(20):1317–1322.
*Chemical Abstracts*, 1993, 119:92, col. 2, abstract No. 63033j.
Clark et al., 1982, *J. Clin. Invest.* 70;1074–1080.
Conte et al., 1992, *Arzheim–Forsch./Drug Res.* 42:847–853.
Conte et al., 1992, *Arzheim–Forsch./Drug Res.* 42:854–858.
Corbett et al., 1996, *J. Exp. Ther. Oncol.* 1: 95–108.
De Franceschi et al., 1994, *J. Clin. Invest.* 93: 1670–1676.
De Franceschi et al., 1996, *Blood* 88(648a):2580.
Douchene et al., 1992, *Arzheim–Forsch./Drug Res.* 42:861–863.
Duhm et al., 1974, *Postgraduate Medical Journal Jul. Suppl.* :13–16.

(List continued on next page.)

*Primary Examiner*—Johann Richter
*Assistant Examiner*—Ebenezer Sackey
*Attorney, Agent, or Firm*—Fish & Richardson P.C.

[57] ABSTRACT

The present invention provides a class of chemical compounds useful as efficacious drugs in the treatment of sickle cell disease and diseases characterized by unwanted or abnormal cell proliferation. The active compounds are substituted triaryl methane compounds or analogues thereof where one or more of the aryl groups is replaced with a heteroaryl, cycloalkyl or heterocycloalkyl group and/or the tertiary carbon atom is replaced with a different atom such as Si, Ge, N or P. The compounds inhibit mammalian cell proliferation, inhibit the Gardos channel of erythrocytes, reduce sickle erythrocyte dehydration and/or delay the occurrence of erythrocyte sickling or deformation.

42 Claims, No Drawings

OTHER PUBLICATIONS

Dykes et al., 1992, *Contrib. Oncol. Basel. Karger* 42:1–22.
Eaton and Hofrichter, 1987, *Blood* 70:1245–1266.
Epstein et al., 1987, *Cornea* 6(4):250–257.
Ethridge et al., 1990, *J. Production Agriculture* 3(2):246–252.
Fahim and Pressman, 1981, *Life Sciences* 29:1959–1966.
Fan et al., 1983, *Yiyao Gongye* 9:2–4.
Ferguson et al., 1992, *Acta Crystallogr.* C48:1228–1231.
Fingl and Woodbury, 1975, In: *The Pharmacological Basis of Therapeutics*, Ch. 1 p1.
Fleming et al., 1982, *Tetrahedron Letters* 23:2053–2056.
Gait, 1984, *Oligonucleotide Synthesis: A Pratical Approach*, IRL Press, Oxford, pp. 13 and 76.
Glidewell and Ferguson, 1994, *Acta Crystallogr.* C50:1362–1366.
Goldberg et al., 1990, *N. Engl. J. Med.* 323(6):366–372.
Grinstein and Smith, 1990, *J. Gen. Physiol.* 95:97–120.
Guy et al., 1973, *Am. J. Med. Sci.* 266:267–277.
Illes et al., 1988, *Acta Phytopathologica et Entomologia Hungarica* 23:243–255.
Hoch and Lecocq, 1957, *Academie des Sciences* 245:73–75.
Holt and Newman, 1972, *J. Clin. Path.* 25:1089–1097.
Hoogerheide and Wyka, 1982, *Analytical Profiles of Drug Substances* 11:225–255.
Illes et al., 1988, *Acta Phytopathologica et Entomologia Hungarcia* 23:243–255.
Izquierdo et al., 1992, *Arzheim–Forsch./Drug Res.* 42:859–860.
Lewis et al., 1980, *J. Am. Chem. Soc.* 102:4659–4664.
Li, F. et al., 1996, *Metal–Based Drugs* 3:241–242.
Liu & Paike, 1987, *Tetrahedron Lett.* 28(33):3763–3766.
Matsuura et al., 1991, *Biochemical Pharmacology* 41:1949–1956.
Miller et al., 1985, *Nature* 313:316–318.
Montero et al., 1991, *Biochem. J.* 277–73–79.
O'Donnell, M. et al., 1995, *Boorganic & Medicinal Chemistry* 3:743–750.
Owens et al., 1984, *Arch Intern Med* 144:290–293.
Paike, 1992, *Mater. Sci.* 18:53–57.
Paoletti, E. G. et al., 1969, *Advan. Exp. Med. Biol.* 22:457–471.
Paoletti, E. G. et al., 1971, *J. Neurosurg* 34:454–455.
Paoletti, P et al., 1972, In: *The Exp. Biol. Of Brain Tumors*, 457–479.
Pappas and Franklin, 1993, *Toxicology* 80:27–35.
Park et al., 1991, *Proc. Natl. Acad. Sci. U.S.A.* 88:2046–2050.
Peppelenbosch et al., 1991, *J. Biol. Chem.* 266:19938–19944.
Perrine et al., 1993, *N. Engl. J. Med.* 328(2):81–86.
Petersen, P. M. et al., 1996, *Bioorganic and Medicinal Chemistry* 4:1107–1112.
Ponnuswamy and Trotter, 1984, *Acta Crystallogr.* C40:142–144.
Rafanell et al., 1992, *Arzheim–Forsch./Drug Res.* 42:836–840.
Rideout, D. C. et al., 1989, *Anti–Cancer Drug Design* 4:265–280.
Rideout, D. et al., 1994, *Int. J. Cancer* 57:247–253.
Ritter, 1985, *Am. J. Obstet. Gynecol.* 152:945–947.
Ritter et al., 1982, *Chemotherapy* 28(Suppl. 1):37–42.
Rosa et al., 1980, *M. Eng. J. Med.* 303:1138–1143.
Rubright, W. C. et al., 1967, *Cancer Research* 27:165–171.
Sawyer et al., 1975, *Drugs* 9:424–447.
Simig, G. et al., 1978, *Tetrahedron* 34:2371–2375.
Stuart et al., 1987, *J. Clin. Pathol.* 40:1182–1186.
Stuart et al., 1994, *British J. Haematol.* 86:820–823.
Tomioka et al., 1981, *Chem. Lett.* 11:1621–1624.
Trudel et al., 1991, *EMBO J.* 11:3157–3165.
Vazquez et al., 1989, *J. Biol. Chem.* 264:20902–20909.
Vericat et al., 1992, *Arzheim–Forsch./Drug Res.* 42:841–846.
Villalobos et al., 1992, *FASEB J.* 6:2742–2747.
Weuta, 1974, *Postgraduate Medical Journal* (Jul. Suppl.):45–48.
Wyche, J. H. and William D. Noteboom, 1979, *Endocrinology* 104:1765–1773.
Zhu et al., 1994, *Cardiology* 85:370–377.

TRIARYL METHANE COMPOUNDS AND ANALOGUES THEREOF USEFUL FOR THE TREATMENT OR PREVENTION OF SICKLE CELL DISEASE OR DISEASES CHARACTERIZED BY ABNORMAL CELL PROLIFERATION

1. CROSS-REFERENCE TO RELATED APPLICATIONS

This application is a continuation-in-part of application Ser. No. 08/618,952, filed Mar. 20, 1996, now pending and Ser. No. 08/618,760, filed Mar. 20, 1996, now pending, each of which is a continuation-in-part of application Ser. No. 08/307,874, filed Sep. 16, 1994, now abandoned. Each of these applications is incorporated herein in its entirety by reference.

2. FIELD OF THE INVENTION

The present invention relates to aromatic organic compounds which are specific, potent and safe inhibitors of the $Ca^{2+}$-activated potassium channel (Gardos channel) of erythrocytes and/or of mammalian cell proliferation. The compounds can be used to reduce sickle erythrocyte dehydration and/or delay the occurrence of erythrocyte sickling or deformation in situ as a therapeutic approach towards the treatment or prevention of sickle cell disease. The compounds can also be used to inhibit mammalian cell proliferation in situ as a therapeutic approach towards the treatment or prevention of diseases characterized by abnormal cell proliferation.

3. BACKGROUND OF THE INVENTION

Sickle cell disease has been recognized within West Africa for several centuries. Sickle cell anemia and the existence of sickle hemoglobin (Hb S) was the first genetic disease to be understood at the molecular level. It is recognized today as the morphological and clinical result of a glycine to valine substitution at the No. 6 position of the beta globin chain (Ingram, 1956, *Nature* 178:792–794. The origin of the amino acid change and of the disease state is the consequence of a single nucleotide substitution (Marotta et al., 1977, *J. Biol. Chem.* 252:5040–5053).

The major source of morbidity and mortality of patients suffering from sickle cell disease is vascular occlusion caused by the sickled cells, which causes repeated episodes of pain in both acute and chronic form and also causes ongoing organ damage with the passage of time. It has long been recognized and accepted that the deformation and distortion of sickle cell erythrocytes upon complete deoxygenation is caused by polymerization and intracellular gelation of sickle hemoglobin, hemoglobin S (Hb S). The phenomenon is well reviewed and discussed by Eaton and Hofrichter, 1987, *Blood* 70:1245. The intracellular gelatin and polymerization of Hb S can occur at any time during erythrocyte's journey through the vasculature. Thus, erythrocytes in patients with sickle cell disease containing no polymerized hemoglobin S may pass through the microcirculation and return to the lungs without sickling, may sickle in the veins or may sickle in the capillaries.

The probability of each of these events is determined by the delay time for intracellular gelation relative to the appropriate capillary transit time (Eaton et al., 1976, *Blood* 47:621). In turn, the delay time is dependent upon the oxygenation state of the hemoglobin, with deoxygenation shortening the delay time. Thus, if it is thermodynamically impossible for intracellular gelation to take place, or if the delay time at venous oxygen pressures is longer than about 15 seconds, cell sickling will not occur. Alternatively, if the delay time is between about 1 and 15 seconds, the red cell will likely sickle in the veins. However, if the delay time is less than about 1 second, red cells will sickle within the capillaries.

For red cells that sickle within the capillaries, a number of possible consequent events exist, ranging from no effect on transit time, to transient occlusion of the capillary, to a more permanent blockage that may ultimately result in ischemia or infarction of the surrounding cells, and in destruction of the red cell.

It has long been recognized that the cytoplasm of the normal erythrocyte comprises approximately 70% water. Water crosses a normal erythrocyte membrane in milliseconds; however, the loss of cell water causes an exponential increase in cytoplasmic viscosity as the mean cell hemoglobin concentration (MCHC) rises above about 32 g/dl. Since cytoplasmic viscosity is a major determinate of erythrocyte deformability and sickling, the dehydration of the erythrocyte has substantial rheological and pathological consequences. Thus, the physiological mechanisms that maintain the water content of a normal erythrocytes and the pathological conditions that cause loss of water from erythrocytes in the blood circulation are critically important. Not surprisingly, regulation of erythrocyte dehydration has been recognized as an important therapeutic approach towards the treatment of sickle cell disease. Since cell water will follow any osmotic change in the intracellular concentration of ions, the maintenance of the red cell's potassium concentration is of particular importance (Stuart and Ellory, 1988, *Brit J. Haematol.* 69:1–4).

Many attempts and approaches to therapeutically treating dehydrated sickle cells (and thus decreasing polymerization of hemoglobin S by lowering the osmolality of plasma) have been tried with limited success, including the following approaches: intravenous infusion of distilled water (Gye et al., 1973, *Am. J. Med. Sci.* 266:267–277); administration of the antidiuretic hormone vasopressin together with a high fluid intake and salt restriction (Rosa et al., 1980, *M. Eng. J. Med.* 303:1138–1143; Charache and Walker, 1981, *Blood* 58:892–896); the use of monensin to increase the cation content of the sickle cell (Clark et al., 1982, *J. Clin. Invest.* 70:1074–1080; Fahim and Pressman, 1981, *Life Sciences* 29:1959–1966); intravenous administration of cetiedil citrate (Benjamin et al., 1986, *Blood* 67:1442–1447; Berkowitz and Orringer, 1984, *Am. J. Hematol.* 17:217–223; Stuart et al., 1987, *J. Clin. Pathol.* 40:1182–1186); and the use of oxpentifylline (Stuart et al., 1987, *J. Clin. Pathol.* 40:1182–1186).

Another approach towards therapeutically treating dehydrated sickle cells involves the administration of imidazole, nitroimidazole and triazole antimycotic agents such as Clotrimazole (U.S. Pat. No. 5,273,992 to Brugnara et al.). Clotrimazole, an imidazole-containing antimycotic agent, has been shown to be a specific, potent inhibitor of the Gardos channel of normal and sickle erythrocytes, and prevents $Ca^{2+}$-dependent dehydration of sickle cells both in vitro and in vivo (Brugnara et al., 1993, *J. Clin. Invest.* 92:520–526; De Franceschi et al., 1994, *J. Clin. Invest.* 93:1670–1676). When combined with a compound which stabilizes the oxyconformation of Hb S, Clotrimazole induces an additive reduction in the clogging rate of a micropore filter and may attenuate the formation of irreversibly sickled cells (Stuart et al., 1994, *J. Haematol.* 86:820–823). Other compounds that contain a heteroaryl imidazole-like moiety believed to be useful in reducing sickle erythrocyte dehydration via Gardos channel inhibition include miconazole, econazole, butoconazole, oxiconazole and sulconazole. Each of these compounds is a known antimycotic. Other imidazole-containing compounds have been found to be incapable of inhibiting the Gardos channel and preventing loss of potassium.

As can be seen from the above discussion, reducing sickle erythrocyte dehydration via blockade of the Gardos channel is a powerful therapeutic approach towards the treatment and/or prevention of sickle cell disease. Compounds capable of inhibiting the Gardos channel as a means of reducing sickle cell dehydration are highly desirable, and are therefore an object of the present invention.

Cell proliferation is a normal part of mammalian existence, necessary for life itself. However, cell proliferation is not always desirable, and has recently been shown to be the root of many life-threatening diseases such as cancer, certain skin disorders, inflammatory diseases, fibrotic conditions and arteriosclerotic conditions.

Cell proliferation is critically dependent on the regulated movement of ions across various cellular compartments, and is associated with the synthesis of DNA. Binding of specific polypeptide growth factors to specific receptors in growth-arrested cells triggers an array of early ionic signals that are critical in the cascade of mitogenic events eventually leading to DNA synthesis (Rozengurt, 1986, *Science* 234:161–164). These include (1) a rapid increase in cystolic $Ca^{2+}$, mostly due to rapid release of $Ca^{2+}$ from intracellular stores; (2) capacitative $Ca^{2+}$ influx in response to opening of ligand-bound and hyperpolarization-sensitive $Ca^{2+}$ channels in the plasma membrane that contribute further to increased intracellular $Ca^{2+}$ concentration (Tsien and Tsien, 1990, *Annu. Rev. Cell Biol.* 6:715–760; Peppelenbosch et al., 1991, *J. Biol. Chem.* 266:19938–19944); and (3) activation of $Ca^{2+}$-dependent $K^+$ channels in the plasma membrane with increased $K^+$ conductance and membrane hyperpolarization (Magni et al., 1991, *J. Biol. Chem.* 261:9321–9327). These mitogen-induced early ionic changes, considered critical events in the signal transduction pathways, are powerful therapeutic targets for inhibition of cell proliferation in normal and malignant cells.

One therapeutic approach towards the treatment of diseases characterized by unwanted or abnormal cell proliferation via alteration of the ionic fluxes associated with early mitogenic signals involves the administration of Clotrimazole. As discussed above, Clotrimazole has been shown to inhibit the $Ca^{2+}$-activated potassium channel of erythrocytes. In addition, Clotrimazole inhibits voltage- and ligand-stimulated $Ca^{2+}$ influx mechanisms in nucleated cells (Villalobos et al., 1992, *FASEB J.* 6:2742–2747; Montero et al., 1991, *Biochem. J.* 277:73–79) and inhibits cell proliferation both in vitro and in vivo (Benzaquen et al., 1995, *Nature Medicine* 1:534–540). Recently, Clotrimazole and other imidazole-containing antimycotic agents capable of inhibiting $Ca^{2+}$-activated potassium channels have been shown to be useful in the treatment of arteriosclerosis (U.S. Pat. No. 5,358,959 to Halperin et al.), as well as other disorders characterized by unwanted or abnormal cell proliferation.

As can be seen from the above discussion, inhibiting mammalian cell proliferation via alteration of ionic fluxes associated with early mitogenic signals is a powerful therapeutic approach towards the treatment and/or prevention of diseases characterized by unwanted or abnormal cell proliferation. Compounds capable of inhibiting mammalian cell proliferation are highly desirable, and are therefore also an object of the present invention.

4. SUMMARY OF THE INVENTION

These and other objects are provided by the present invention, which in one aspect provides a class of organic compounds which are potent, selective and safe inhibitors of the $Ca^{2+}$-activated potassium channel (Gardos channel) of erythrocytes, particularly sickle erythrocytes, and/or of mammalian cell proliferation. The compounds are generally substituted triaryl methane compounds, or analogues thereof wherein one or more of the aryl moieties is replaced with a heteroaryl, cycloalkyl or heterocycloalkyl moiety and/or wherein the tertiary carbon is replaced with another atom such as Si, Ge, N, or P.

In one illustrative embodiment, the compounds capable of inhibiting the Gardos channel and/or mammalian cell proliferation according to the invention are compounds having the structural formula:

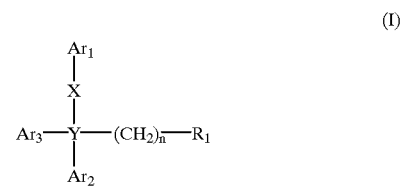

(I)

or pharmaceutically acceptable salts of hydrates thereof, wherein:

n is 0, 1, 2, 3 or 4;

X is absent, $(C_1-C_3)$ alkyl, $(C_1-C_3)$ alkenyl, or $(C_1-C_3)$ alkynyl;

Y is C, N, P, Si or Ge;

$R_1$ is absent, -halo, —R, —OR, —SR, —$NR_2$, —$ONR_2$, —$NO_2$, —CN, —C(O)R, —C(S)R, —C(O)OR, —C(S)OR, —C(O)SR, —C(S)SR, —C(O)$NR_2$, —C(S)$NR_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$ or aryl;

$Ar_1$ is aryl, substituted aryl, heteroaryl other than imidazole, nitroimidazole and triazole, heteroarylium other than imidazolium, nitroimidazolium and triazolium, $(C_5-C_8)$ cycloalkyl or $(C_5-C_8)$ heterocycloalkyl;

$Ar_2$ is aryl or substituted aryl;

$Ar_3$ is aryl, substituted aryl, biaryl or heteroaryl other than imidazole, nitroimidazole and triazole;

each R is independently selected from the group consisting of —H, $(C_1-C_6)$ alkyl, substituted $(C_1-C_6)$ alkyl, $(C_1-C_6)$ alkenyl, substituted $(C_1-C_6)$ alkenyl, $(C_1-C_6)$ alkynyl, substituted $(C_1-C_6)$ alkynyl and $(C_1-C_6)$ alkoxy;

the aryl substituents are each independently selected from the group consisting of -halo, trihalomethyl, —R, —R', —OR', —SR', NR'$_2$, —$NO_2$, —CN, —C(O)R', —C(S)R', —C(O)OR', —C(S)OR', —C(O)SR'and —C(S)SR';

the alkyl, alkenyl and alkynyl substituents are each independently selected from the group consisting of -halo, —R', —OR', —SR', NR'$_2$, —$NO_2$, —CN, —C(O)R', —C(S)R', —C(O)OR', —C(S)OR', —C(O)SR', —C(S)SR', aryl, γ-butyrolactonyl, pyrrolidinyl and succinic anhydridyl; and each R' is independently selected from the group consisting of —H, ($C_1$–$C_6$) alkyl, ($C_1$–$C_6$) alkenyl and ($C_1$–$C_6$) alkynyl.

In another aspect, the present invention provides pharmaceutical compositions comprising one or more compounds according to the invention in admixture with a pharmaceutically acceptable carrier, excipient or diluent. Such a preparation can be administered in the methods of the invention.

In still another aspect, the invention provides a method for reducing sickle erythrocyte dehydration and/or delaying the occurrence of erythrocyte sickling or deformation in situ. The method involves contacting a sickle erythrocyte in situ with an amount of at least one compound according to the invention, or a pharmaceutical composition thereof, effective to reduce sickle erythrocyte dehydration and/or delay the occurrence of erythrocyte sickling or deformation. In a preferred embodiment, the sickle cell dehydration is reduced and erythrocyte deformation is delayed in a sickle erythrocyte that is within the microcirculation vasculature of a subject, thereby preventing or reducing the vaso-occlusion and consequent adverse effects that are commonly caused by sickled cells.

In still another aspect, the invention provides a method for the treatment and/or prevention of sickle cell disease in a subject, such as a human. The method involves administering a prophylactically or therapeutically effective amount of at least one compound according to the invention, or a pharmaceutical composition thereof, to a patient suffering from sickle cell disease. The patient may be suffering from either acute sickle crisis or chronic sickle cell episodes.

In yet another aspect, the invention provides a method for inhibiting mammalian cell proliferation in situ. The method involves contacting a mammalian cell in situ with an amount of at least one compound according to the invention, or a pharmaceutical composition thereof, effective to inhibit cell proliferation. The compound or composition may act either cytostatically, cytotoxically or a by a combination of both mechanisms to inhibit proliferation. Mammalian cells in this manner include vascular smooth muscle cells, fibroblasts, endothelial cells, various types of pre-cancer cells and various types of cancer cells.

In still another aspect, the invention provides a method for treating and/or preventing unwanted or abnormal cell proliferation in a subject, such as a human. In the method, at least one compound according to the invention, or a pharmaceutical composition thereof, is administered to a subject in need of such treatment in an amount effective to inhibit the unwanted or abnormal mammalian cell proliferation. The compound and/or composition may be applied locally to the proliferating cells, or may be administered to the subject systemically. Preferably, the compound and/or composition is administered to a subject that has a disorder characterized by unwanted or abnormal cell proliferation. Such disorders include, but are not limited to, cancer, epithelial precancerous lesions, non-cancerous angiogenic conditions or arteriosclerosis.

In a final aspect, the invention provides a method for the treatment and/or prevention of diseases that are characterized by unwanted and/or abnormal mammalian cell proliferation. The method involves administering a prophylactically or therapeutically effective amount of at least one compound according to the invention, or a pharmaceutical composition thereof, to a subject in need of such treatment. Diseases that are characterized by abnormal mammalian cell proliferation which can be treated or prevented by way of the methods of the invention include, but are not limited to, cancer, blood vessel proliferative disorders, fibrotic disorders and arteriosclerotic conditions.

4.1 Definitions

As used herein, the following terms shall have the following meanings:

"Alkyl:" refers to a saturated branched, straight chain or cyclic hydrocarbon radical. Typical alkyl groups include methyl, ethyl, propyl, isopropyl, cyclopropyl, butyl, isobutyl, t-butyl, cyclobutyl, pentyl, isopentyl, cyclopentyl, hexyl, cyclohexyl and the like.

"Heterocycloalkyl:" refers to a saturated cyclic hydrocarbon radical wherein one or more of the carbon atoms is replaced with another atom such as Si, Ge, N, O, S or P. Typical heterocycloalkyl groups include, but are not limited to, morpholino, thiolino, piperidyl, pyrrolidinyl, piperazyl, pyrazolidyl, imidazolidinyl, and the like.

"Alkenyl:" refers to an unsaturated branched, straight chain or cyclic hydrocarbon radical having at least one carbon-carbon double bond. The radical may be in either the cis or trans conformation about the double bond(s). Typical alkenyl groups include ethenyl, propenyl, isopropenyl, cyclopropenyl, butenyl, isobutenyl, cyclobutenyl, tert-butenyl, pentenyl, hexenyl and the like.

"Alkynyl:" refers to an unsaturated branched, straight chain or cyclic hydrocarbon radical having at least one carbon-carbon triple bond. Typical alkynyl groups include ethynyl, propynyl, butynyl, isobutynyl, pentynyl, hexynyl and the like.

"Alkoxy:" refers to an —OR radical, where R is alkyl, alkenyl or alkynyl, as defined above.

"Aryl:" refers to an unsaturated cyclic hydrocarbon radical having a conjugated $\pi$ electron system. Typical aryl groups include, but are not limited to, penta-2,4-diene, phenyl, naphthyl, anthracyl, azulenyl, indacenyl, and the like.

"Heteroaryl:" refers to an aryl group wherein one or more of the ring carbon atoms is replaced with another atom such as N, O or S. Typical heteroaryl groups include, but are not limited to, furanyl, thienyl, indolyl, pyrrolyl, pyranyl, pyridyl, pyrimidyl, pyrazyl, pyridazyl, and the like.

"Heteroarylium:" refers to a heteroaryl group wherein one or more hydrogens has been added to any position of the neutral parent ring. Typical heteroarylium groups include, but are not limited to, pyridinium, pyrazinium, pyrimidinium, pyridazinium, 1,3,5-triazinium, and the like.

"In Situ:" refers to and includes the terms "in vivo," "ex vivo," and "in vitro" as these terms are commonly recognized and understood by persons ordinarily skilled in the art. Moreover, the phrase "in situ" is employed herein in its broadest connotative and denotative contexts to identify an entity, cell or tissue as found or in place, without regard to its source or origin, its condition or status or its duration or longevity at that location or position.

5. DETAILED DESCRIPTION OF THE INVENTION

As discussed in the Background section, blockade of sickle dehydration via inhibition of the Gardos channel is a powerful therapeutic approach towards the treatment and/or prevention of sickle cell disease. In vitro studies have shown that Clotrimazole, an imidazole-containing antimycotic agent, blocks $Ca^{2+}$-activated $K^+$ transport and cell dehydration in sickle erythrocytes (Brugnara et al., 1993, *J. Clin. Invest.* 92:520–526). Studies in a transgenic mouse model for sickle cell disease (SAD mouse, Trudel et al., 1991, *EMBO J.* 11:3157–3165) show that oral administration of Clotrimazole leads to inhibition of the red cell Gardos channel, increased red cell $K^+$ content, a decreased mean cell hemoglobin concentration (MCHC) and decreased cell density (De Franceschi et al., 1994, *J. Clin. Invest.* 93:1670–1676). Moreover, therapy with oral Clotrimazole induces inhibition of the Gardos channel and reduces erythrocyte dehydration in patients with sickle cell disease (Brugnara et al., 1996, *J. Clin. Invest.* 97:1227–1234). Other antimycotic agents which inhibit the Gardos channel in vitro include miconazole, econazole, butoconazole, oxiconazole and sulconazole (U.S. Pat. No. 5,273,992 to Brugnara et al.). All of these compounds contain an imidazole-like ring, i.e., a heteroaryl ring containing two or more nitrogens.

Also as discussed in the Background section, the modulation of early ionic mitogenic signals and inhibition of cell proliferation are powerful therapeutic approaches towards the treatment and/or prevention of disorders characterized by abnormal cell proliferation. It has been shown that Clotrimazole, in addition to inhibiting the Gardos channel of erythrocytes, also modulates ionic mitogenic signals and inhibits cell proliferation both in vitro and in vivo.

For example, Clotrimazole inhibits the rate of cell proliferation of normal and cancer cell lines in a reversible and dose-dependent manner in vitro (Benzaquen et al., 1995 *Nature Medicine* 1:534–540). Clotrimazole also depletes the intracellular $Ca^{2+}$ stores and prevents the rise in cystolic $Ca^{2+}$ that normally follows mitogenic stimulation. Moreover, in mice with severe combined immunodeficiency disease (SCID) and inoculated with MM-RU human melanoma cells, daily administration of Clotrimazole resulted in a significant reduction in the number of lung metastases observed (Benzaquen et al., supra).

Quite surprisingly, it has now been discovered that the imidazole-like ring moieties of Clotrimazole and the other above-mentioned antimycotic agents, which are well-recognized as the essential functionality underlying their antimycotic and other biological activities, is not the underlying functionality responsible for effecting inhibition of the Gardos channel or inhibition of mitogen-induced mammalian cell proliferation. Thus, based in part on this surprising discovery, in one aspect the present invention provides a new class of organic compounds that are capable of inhibiting the $Ca^{2+}$-activated potassium channel (Gardos channel) of erythrocytes, particularly sickle erythrocytes and/or of inhibiting mammalian cell proliferation, particularly mitogen-induced cell proliferation.

In another aspect, the invention provides a method of reducing sickle cell dehydration and/or delaying the occurrence of erythrocyte sickling in situ as a therapeutic approach towards the treatment of sickle cell disease. In its broadest sense, the method involves only a single step—the administration of at least one pharmacologically active compound of the invention, or a composition thereof, to a sickle erythrocyte in situ in an amount effective to reduce dehydration and/or delay the occurrence of cell sickling or deformation.

While not intending to be bound by any particular theory, it is believed that administration of the active compounds described herein in appropriate amounts to sickle erythrocytes in situ causes nearly complete inhibition of the Gardos channel of sickle cells, thereby reducing the dehydration of sickle cells and/or delaying the occurrence of cell sickling or deformation. In a preferred embodiment, the dehydration of a sickle cell is reduced and/or the occurrence of sickling is delayed in a sickle cell that is within the microcirculation vasculature of the subject, thereby reducing or eliminating the vaso-occlusion that is commonly caused by sickled cells.

Based in part on the surmised importance of the Gardos channel as a therapeutic target in the treatment of sickle cell disease, the invention is also directed to methods of treating or preventing sickle cell disease. In the method, an effective amount of one or more compounds according to the invention, or a pharmaceutical composition thereof, is administered to a patient suffering from sickle cell disease. The methods may be used to treat sickle cell disease prophylactically to decrease intracellular Hb S concentration and/or polymerization, and thus diminish the time and duration of red cell sickling and vaso-occlusion in the blood circulation. The methods may also be used therapeutically in patients with acute sickle cell crisis, and in patients suffering chronic sickle cell episodes to control both the frequency and duration of the crises.

The compounds of the invention are also potent, specific inhibitors of mammalian cell proliferation. Thus, in another aspect, the invention provides methods of inhibiting mammalian cell proliferation as a therapeutic approach towards the treatment or prevention of diseases characterized by unwanted or abnormal cell proliferation. In its broadest sense, the method involves only a single step—the administration of an effective amount of at least one pharmacologically active compound according to the invention to a mammalian cell in situ. The compound may act cytostatically, cytotoxically, or by a combination of both mechanisms to inhibit cell proliferation. Mammalian cells treatable in this manner include vascular smooth muscle cells, fibroblasts, endothelial cells, various pre-cancer cells and various cancer cells. In a preferred embodiment, cell proliferation is inhibited in a subject suffering from a disorder that is characterized by unwanted or abnormal cell proliferation. Such diseases are described more fully below.

Based in part on the surmised role of mammalian cell proliferation in certain diseases, the invention is also directed to methods of treating or preventing diseases characterized by abnormal cell proliferation. In the method, an effective amount of at least one compound according to the invention, or a pharmaceutical composition thereof, is administered to a patient suffering from a disorder that is characterized by abnormal cell proliferation. While not intending to be bound by any particular theory, it is believed that administration of an appropriate amount of a compound according to the invention to a subject inhibits cell proliferation by altering the ionic fluxes associated with early mitogenic signals. Such alteration of ionic fluxes is thought to be due to the ability of the compounds of the invention to inhibit potassium channels of cells, particularly $Ca^{2+}$-activated potassium channels. The method can be used prophylactically to prevent unwanted or abnormal cell proliferation, or may be used therapeutically to reduce or arrest proliferation of abnormally proliferating cells. The compound, or a pharmaceutical formulation thereof, can be applied locally to proliferating cells to arrest or inhibit proliferation at a desired time, or may be administered to a subject systemically to arrest or inhibit cell proliferation.

Diseases which are characterized by abnormal cell proliferation that can be treated or prevented by means of the present invention include blood vessel proliferative disorders, fibrotic disorders, arteriosclerotic disorders and various cancers.

Blood vessel proliferation disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferative disorders include arthritis, where new capillary blood vessels invade the joint and destroy cartilage and ocular diseases such as diabetic retinopathy, where new capillaries in the retina invade the vitreous, bleed and cause blindness and neovascular glaucoma.

Another example of abnormal neovascularization is that associated with solid tumors. It is now established that unrestricted growth of tumors is dependent upon angiogenesis and that induction of angiogenesis by liberation of angiogenic factors can be an important step in carcinogenesis. For example, basic fibroblast growth factor (bFGF) is liberated by several cancer cells and plays a crucial role in cancer angiogenesis. The demonstration that certain animal tumors regress when angiogenesis is inhibited has provided the most compelling evidence for the role of angiogenesis in tumor growth. Other cancers that are associated with neovascularization include hemangioendotheliomas, hemangiomas and Kaposi's sarcoma.

Proliferation of endothelial and vascular smooth muscle cells is the main feature of neovascularization. The invention is useful in inhibiting such proliferation, and therefore in inhibiting or arresting altogether the progression of the angiogenic condition which depends in whole or in part upon such neovascularization. The invention is particularly useful when the condition has an additional element of endothelial or vascular smooth muscle cell proliferation that is not necessarily associated with neovascularization. For example, psoriasis may additionally involve endothelial cell proliferation that is independent of the endothelial cell proliferation associated with neovascularization. Likewise, a solid tumor which requires neovascularization for continued growth may also be a tumor of endothelial or vascular smooth muscle cells. In this case, growth of the tumor cells themselves, as well as the neovascularization, is inhibited by the compounds described herein.

The invention is also useful for the treatment of fibrotic disorders such as fibrosis and other medical complications of fibrosis which result in whole or in part from the proliferation of fibroblasts. Medical conditions involving fibrosis (other than atherosclerosis, discussed below) include undesirable tissue adhesion resulting from surgery or injury.

Other cell proliferative disorders which can be treated by means of the invention include arteriosclerotic conditions. Arteriosclerosis is a term used to describe a thickening and hardening of the arterial wall. An arteriosclerotic condition as used herein means classical atherosclerosis, accelerated atherosclerosis, atherosclerotic lesions and any other arteriosclerotic conditions characterized by undesirable endothelial and/or vascular smooth muscle cell proliferation, including vascular complications of diabetes.

Proliferation of vascular smooth muscle cells is a main pathological feature in classical atherosclerosis. It is believed that liberation of growth factors from endothelial cells stimulates the proliferation of subintimal smooth muscle which, in turn, reduces the caliber and finally obstructs the artery. The invention is useful in inhibiting such proliferation, and therefore in delaying the onset of, inhibiting the progression of, or even halting the progression of such proliferation and the associated atherosclerotic condition.

Proliferation of vascular smooth muscle cells produces accelerated atherosclerosis, which is the main reason for failure of heart transplants that are not rejected. This proliferation is also believed to be mediated by growth factors, and can ultimately result in obstruction of the coronary arteries. The invention is useful in inhibiting such obstruction and reducing the risk of, or even preventing, such failures.

Vascular injury can also result in endothelial and vascular smooth muscle cell proliferation. The injury can be caused by any number of traumatic events or interventions, including vascular surgery and balloon angioplasty. Restenosis is the main complication of successful balloon angioplasty of the coronary arteries. It is believed to be caused by the release of growth factors as a result of mechanical injury to the endothelial cells lining the coronary arteries. Thus, by inhibiting unwanted endothelial and smooth muscle cell proliferation, the compounds described herein can be used to delay, or even avoid, the onset of restenosis.

Other atherosclerotic conditions which can be treated or prevented by means of the present invention include diseases of the arterial walls that involve proliferation of endothelial and/or vascular smooth muscle cells, such as complications of diabetes, diabetic glomerulosclerosis and diabetic retinopathy.

The compounds described herein are also useful in treating or preventing various types of cancers. Cancers which can be treated by means of the present invention include, but are not limited to, biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute and chronic lymphocytic and myelogenous leukemia, multiple myeloma, AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma (teratomas, choriocarcinomas)), stromal tumors and germ cell tumors; thyroid cancer, including thyroid adenocarcinoma and medullar carcinoma; and renal cancer including adenocarcinoma and Wilms tumor.

The compounds of the invention are useful with hormone dependent and also with nonhormone dependent cancers. They also are useful with prostate and nonprostate cancers and with breast and nonbreast cancers. They further are useful with multidrug resistant strains of cancer.

In addition to the particular disorders enumerated above, the invention is also useful in treating or preventing dermatological diseases including keloids, hypertrophic scars, seborrheic dermatosis, papilloma virus infection (e.g., producing verruca vulgaris, verruca plantaris, verruca plan, condylomata, etc.), eczema and epithelial precancerous lesions such as actinic keratosis; other inflammatory diseases including proliferative glomerulonephritis; lupus erythematosus; scleroderma; temporal arthritis; thromboangiitis obliterans; mucocutaneous lymph node syndrome; and other pathologies mediated by growth factors including uterine leiomyomas.

The compounds and methods of the invention provide myriad advantages over agents and methods commonly used to treat sickle cell disease and/or cell proliferative disorders. The compounds and methods of the invention also provide myriad advantages over the treatment of sickle cell disease and/or cell proliferative disorders with Clotrimazole or other antimycotic agents. For example, many of the compounds of the invention are more potent than Clotrimazole in in vitro tests, and therefore may provide consequential therapeutic advantages in clinical settings.

Most significantly, the compounds of the invention have reduced toxicity as compared with these other agents. For Clotrimazole, it is well-known that the imidazole moiety is responsible for inhibiting a wide range of cytochrome P-450 isozyme catalyzed reactions, which constitutes their main toxicological effects (Pappas and Franklin, 1993, *Toxicology* 80:27–35; Matsuura et al., 1991, *Biochemical Pharmacology* 41:1949–1956). Analogues and metabolites of Clotrimazole do not induce cytochrome P-450 (Matsuura et al., 1991, *Biochemical Pharmacology* 41:1949–1956), and therefore do not share Clotrimazole's toxicity.

5.1 The Compounds

The compounds which are capable of inhibiting the Gardos channel and/or mammalian cell proliferation according to the invention are generally triaryl methane compounds or analogues thereof wherein one or more of the aryl moieties is replaced with a heteroaryl, cycloalkyl or heterocycloalkyl moiety and/or wherein the tertiary carbon is replaced with another atom such as Si, Ge, N or P. In one illustrative embodiment, the compounds of the invention are compounds having the formula:

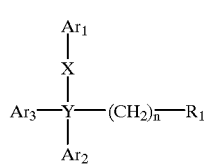
(I)

wherein:
n is 0, 1, 2, 3 or 4;
X is absent, ($C_1$–$C_3$) alkyl, ($C_1$–$C_3$) alkenyl or ($C_1$–$C_3$) alkynyl;
Y is C, N, P, Si or Ge;
$R_1$ is absent, -halo, —R, —OR, —SR, —$NR_2$, —$ONR_2$, —$NO_2$, —CN, —C(O)R, —C(S)R, —C(O)OR, —C(S)OR, —C(O)SR, —C(S)SR, —C(O)$NR_2$, —C(S)$NR_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$ or aryl;
$Ar_1$ is aryl, substituted aryl, heteroaryl other than imidazole, nitroimidazole and triazole, heteroarylium other than imidazolium, nitroimidazolium and triazolium, ($C_5$–$C_8$) cycloalkyl or ($C_5$–$C_8$) heterocycloalkyl;
$Ar_2$ is aryl or substituted aryl;
$Ar_3$ is aryl, substituted aryl, biaryl or heteroaryl other than imidazole, nitroimidazole and triazole;
each R is independently selected from the group consisting of —H, ($C_1$–$C_6$) alkyl, substituted ($C_1$–$C_6$) alkyl, ($C_1$–$C_6$) alkenyl, substituted ($C_1$–$C_6$) alkenyl, ($C_1$–$C_6$) alkynyl, substituted ($C_1$–$C_6$) alkynyl and ($C_1$–$C_6$) alkoxy;
the aryl substituents are each independently selected from the group consisting of -halo, trihalomethyl, —R, —R', —OR', —SR', $NR'_2$, —$NO_2$, —CN, —C(O)R', —C(S)R', —C(O)OR', —C(S)OR', —C(O)SR' and —C(S)SR';

the alkyl, alkenyl and alkynyl substituents are each independently selected from the group consisting of -halo, —R', —OR', —SR', $NR'_2$, —$NO_2$, —CN, —C(O)R', —C(S)R', —C(O)OR', —C(S)OR', —C(O)SR', —C(S)SR', aryl, γ-butyrolactonyl, pyrrolidinyl and succinic anhydridyl; and each R' is independently selected from the group consisting of —H, ($C_1$–$C_6$) alkyl, ($C_1$–$C_6$) alkenyl and ($C_1$–$C_6$) alkynyl.

In another illustrative embodiment, the compounds of the invention are those of formula (I), except that the compound is not 1-(2-chlorophenyl)-1,1-diphenyl methanol, 1-(2-chlorophenyl)-1,1-diphenyl methane or 1-(2-chlorophenyl)-1-(4-hydroxyphenyl)-1-phenyl methane.

In yet another illustrative embodiment, the compounds of the invention are those of formula (I), except that the compound is not any compound encompassed by the formula:

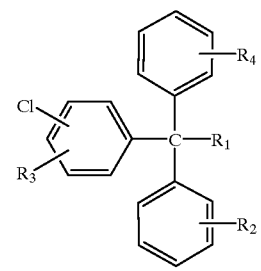

wherein:

$R_1$ is —H, —OH, alkyl or alkoxy;

$R_2$ is —H or —OH;

$R_3$ is —H, —OH or halogen; and $R_4$ is —H, —OH or halogen.

In still another illustrative embodiment, the compounds of the invention are those of formula (I), except that the compound is not any compound encompassed by the formula:

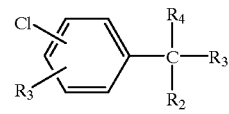

wherein:

$R_1$ is —H, —OH or halogen;

$R_2$ is absent, —H, phenyl or hydroxyl-substituted phenyl;

$R_3$ is —H, —OH, lower alkyl or lower alkoxy;

$R_4$ is —S—$CH_2$—$R_5$, —O—$CH_2$—$R_5$, =N—O—$CH_2$—$R_5$, $CH_2$—CH($CH_3$)-S-substituted phenyl, O-phenyl-CH=$CH_2$, phenyl or substituted phenyl, the phenyl substituent being —OH or halogen;

$R_5$ is vinyl, phenyl, halogen mono-substituted phenyl, halogen di-substituted phenyl, phenyl-S-phenyl, —$CH_2$—O-phenyl, —$CH_2$—O-(halogen-substituted) phenyl or a substituent of the formula:

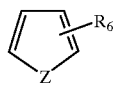

wherein Z is S, O or N; and

R₆ is —H or halogen.

In a preferred embodiment, the substituents of the compounds of formula (I) are as follows:

n is 0, 1, 2, 3 or 4;

X is absent or —C≡C—;

Y is C, N, P, Si or Ge;

$R_1$ is absent, —F, —Cl, —Br, —R, —OR, —SR, —NR₂, —ONR₂, —NO₂, —CN, —C(O)R, —C(O)OR, —C(O)NR₂, —C(O)NR(OR), —CH[C(O)OR]₂ or cyclo-penta-2,4-dien-1-ylidene;

$Ar_1$ is phenyl, substituted phenyl, heteroaryl other than imidazole, nitroimidazole and triazole, cyclohexyl, piperidyl or pyridinium;

$Ar_2$ is phenyl or substituted phenyl;

$Ar_3$ is phenyl, substituted phenyl, biphenyl, naphthyl or pyridyl;

R is —H, (C₁–C₃) alkyl, substituted (C₁–C₃) alkyl, (C₁–C₃) alkenyl, substituted (C₁–C₃) alkenyl (C₁–C₃) alkynyl, substituted (C₁–C₃) alkynyl and (C₁–C₃) alkoxy;

the phenyl substituents are each independently selected from the group consisting of —F, —Cl, —Br, —CF₃, —R, —R', —OR', —SR', NR'₂, —NO₂, —CN, —C(O)R'and —C(O)OR';

the alkyl, alkenyl and alkynyl substituents are each independently selected from the group consisting of —F, —Cl, —Br, —R', —OR', —SR', NR'₂, —NO₂, —CN, —C(O)R', —C(O)OR', naphthyl, γ-butyrolactonyl and pyrrolidinyl; and each R' is independently selected from the group consisting of —H, (C₁–C₃) alkyl, (C₁–C₃) alkenyl and (C₁–C₃) alkynyl.

Exemplary preferred compounds according to formula (I) include those listed in TABLE A, below.

TABLE A

Exemplary Compounds (1)
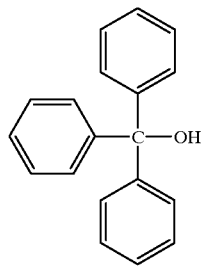

(2)
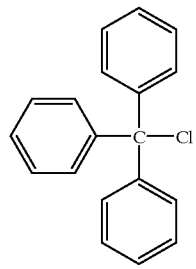

(3)
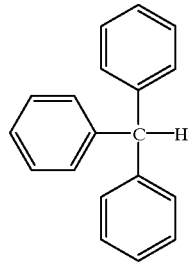

(4)
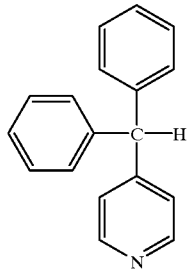

(5)
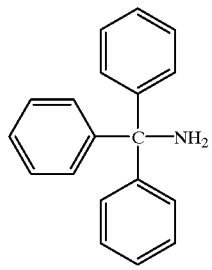

(6)
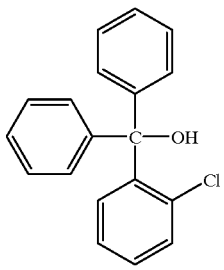

TABLE A-continued
Exemplary Compounds
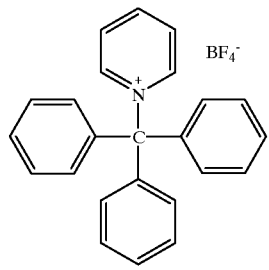 (7)
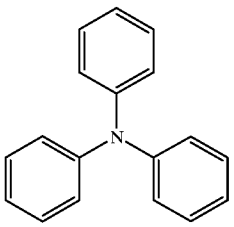 (8)
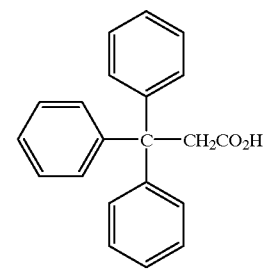 (9)
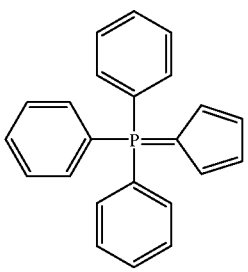 (10)
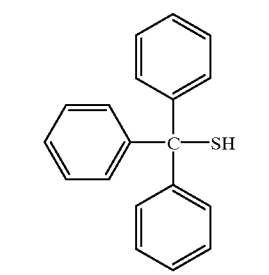 (11)
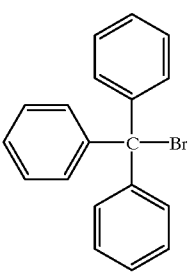 (12)
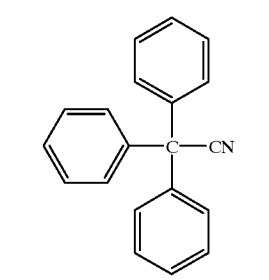 (13)
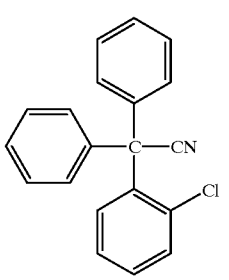 (14)
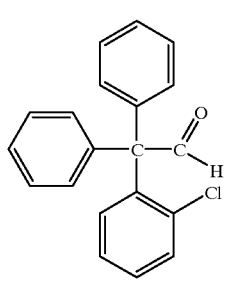 (15)
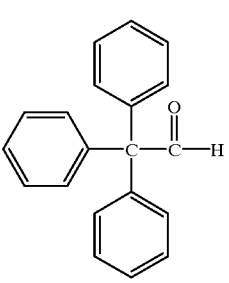 (16)

TABLE A-continued
Exemplary Compounds
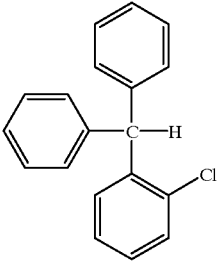(17)
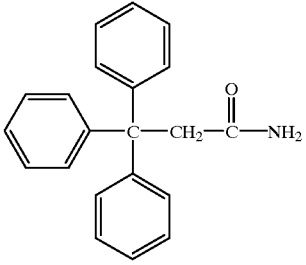(18)
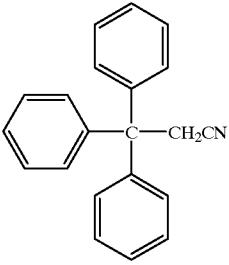(19)
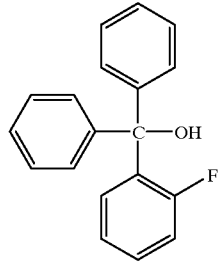(20)
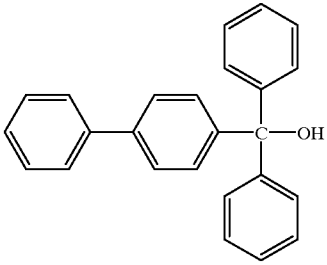(21)
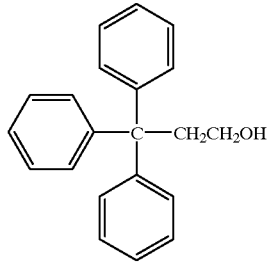(22)
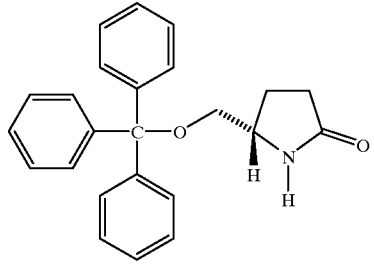(23)
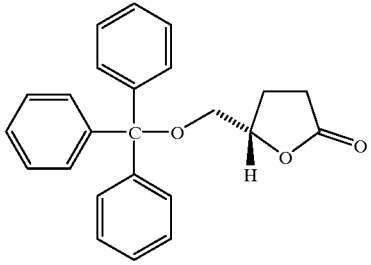(24)
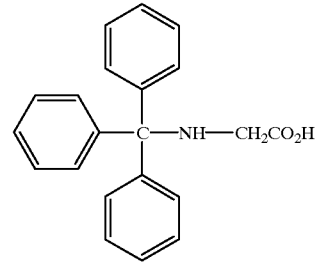(25)
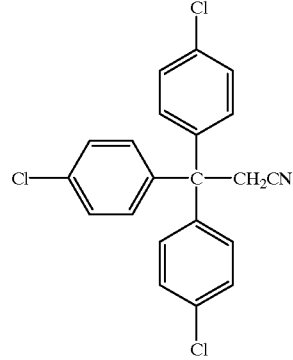(26)

TABLE A-continued
Exemplary Compounds
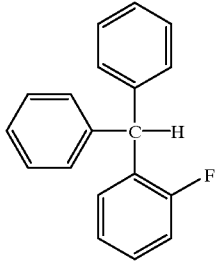
(27)
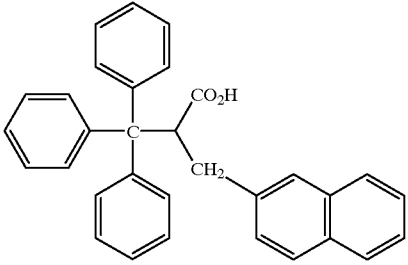
(28)
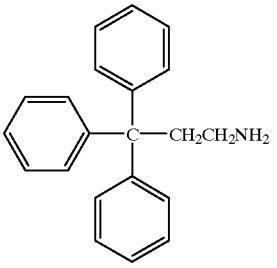
(29)
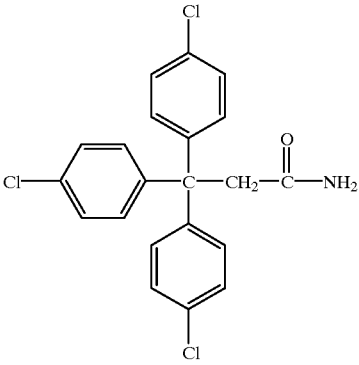
(30)
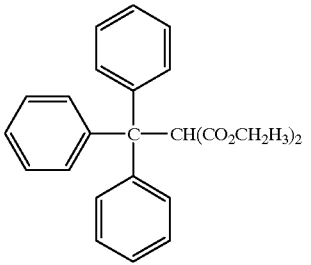
(31)
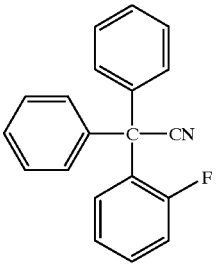
(32)
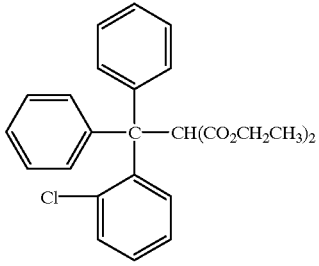
(33)
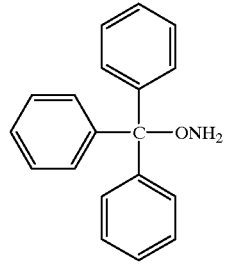
(34)
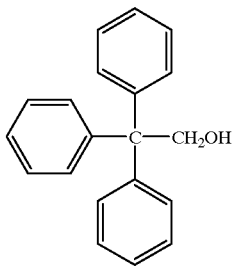
(35)
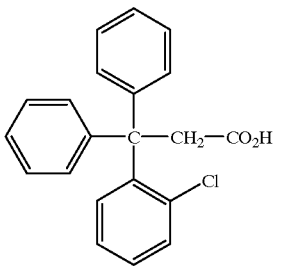
(36)

TABLE A-continued

Exemplary Compounds

(37) Ph₃C-C(=O)-CH₃

(38) Ph₃C-CH₂-C(=O)H

(39) (4-ClC₆H₄)₃C-CH₂CO₂H

(40) (4-ClC₆H₄)₃C-CH₂C(=O)N(CH₃)(OCH₃)

(41) (4-ClC₆H₄)₃C-CH₂CH₂NH₂

(42) Ph₂C(OH)-(2-HOC₆H₄)

(43) (4-ClC₆H₄)(Ph)₂C-OH

(44) Ph₃Si-C≡CH

TABLE A-continued
Exemplary Compounds
(45) 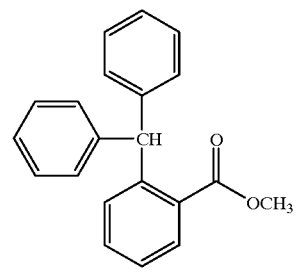
(46) 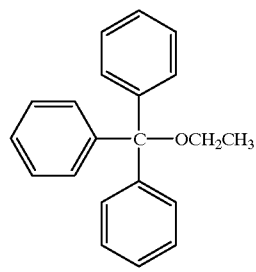
(47) 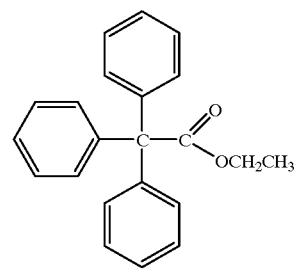
(48) 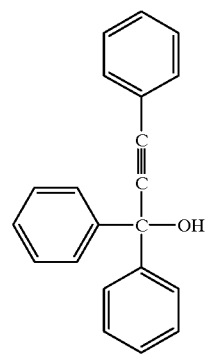
(49) 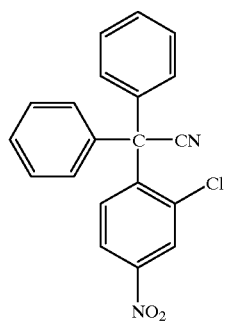
(50) 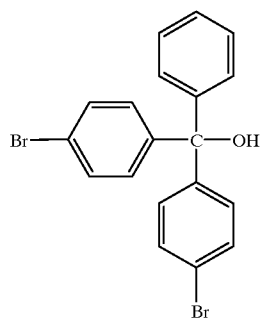
(51) 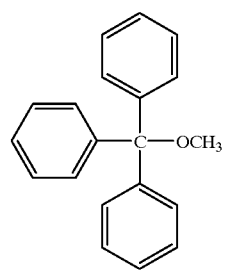
(52) 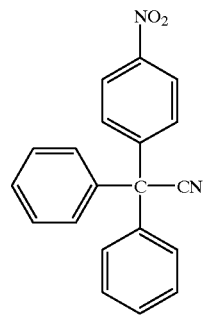

TABLE A-continued
Exemplary Compounds
(53) 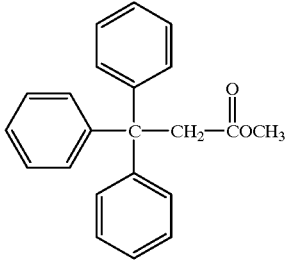
(54) 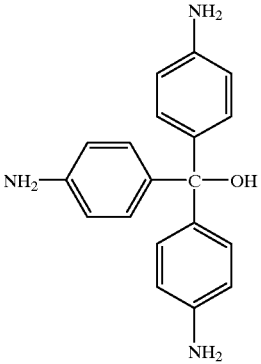
(55) 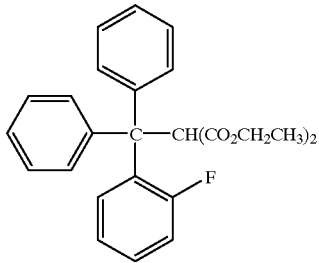
(56) 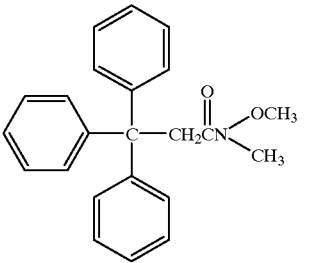
(57) 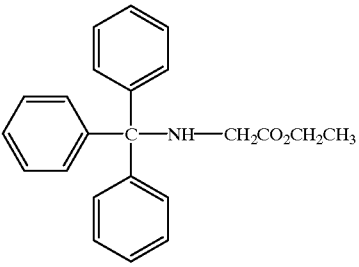
(58) 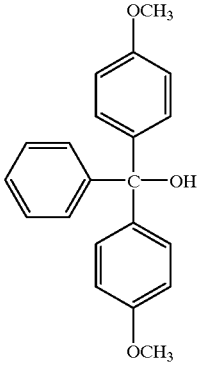
(59) 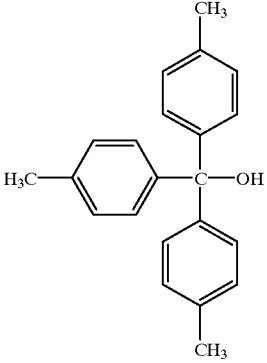
(60) 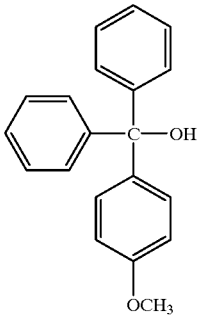

TABLE A-continued
Exemplary Compounds
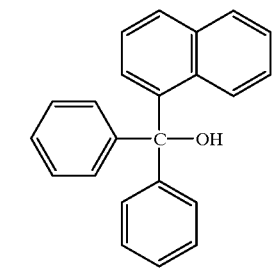 (61)
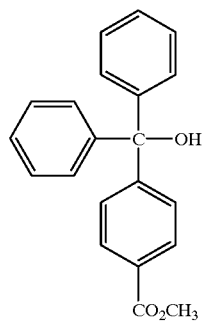 (62)
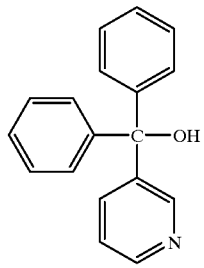 (63)
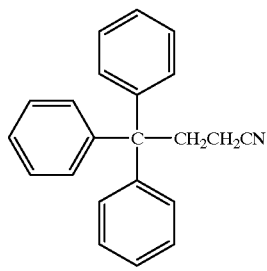 (64)
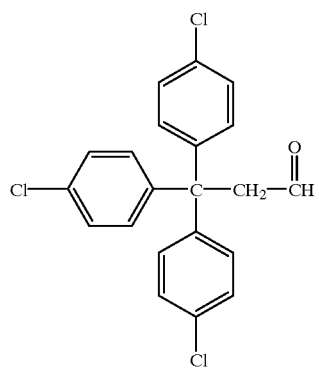 (65)
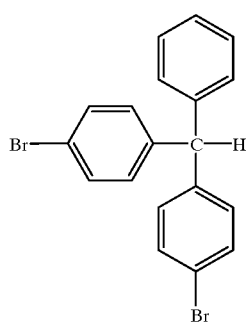 (66)
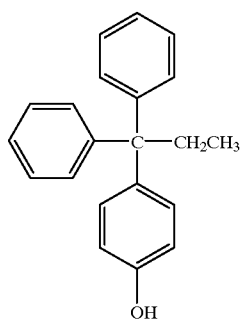 (67)
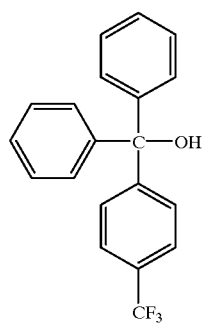 (68)

TABLE A-continued

Exemplary Compounds

(69) Ph₃C-C(=O)-CH₂Br

(70) Ph₂(2-ClC₆H₄)C-CH₂C(=O)N(OCH₃)(CH₃)

(71) Ph₃Si-C₆H₄-CH₂CN

(72) Ph₃Ge-CH₂CH₂CH₂CH₂OH

(73) Ph₃Si-CH₂CH₂CH₂CH₂OH

(74) Ph₃C-CH₂CH₂CO₂H

(75) Ph₂(2-ClC₆H₄)C-C(=O)NH₂

(76) Ph₃Si-(2-thienyl)

(77) Ph₃Ge-OH

(78) Ph₃C-CH₂CH₂C(=O)NH₂

TABLE A-continued
Exemplary Compounds
(79) 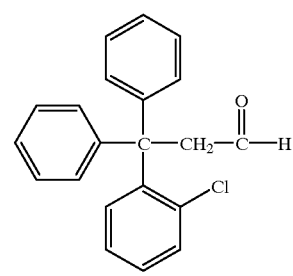
(80) 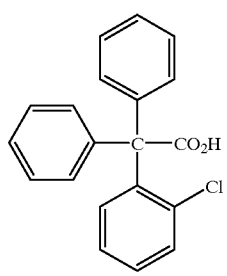
(81) 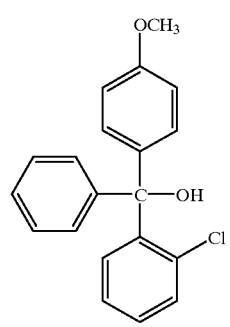
(82) 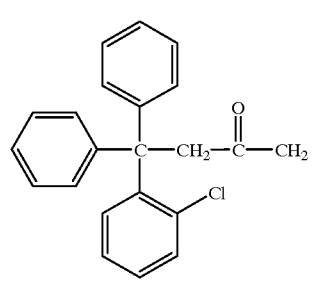
(83) 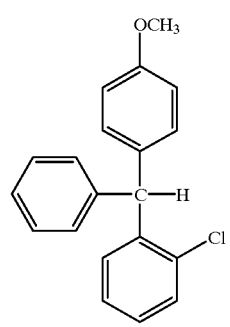
(84) 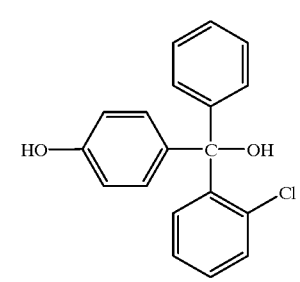
(85) 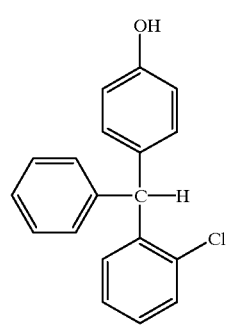
(86) 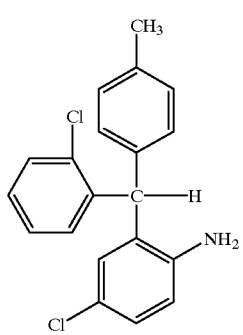
(87) 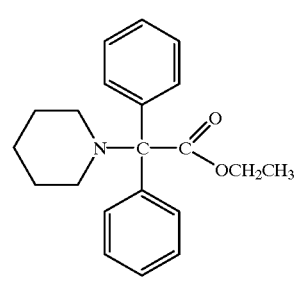
(88) 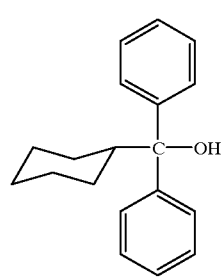

TABLE A-continued

Exemplary Compounds

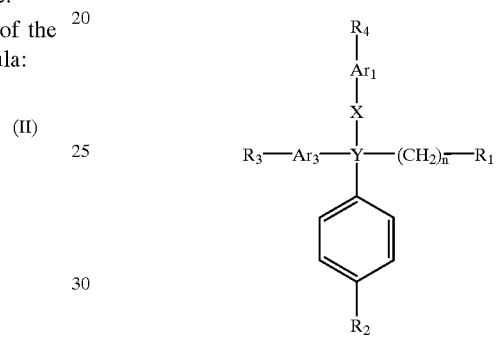

The compounds will be referred to herein by way of compound numbers as presented in TABLE A, above.

In another preferred embodiment, the compounds of the invention are compounds having the structural formula:

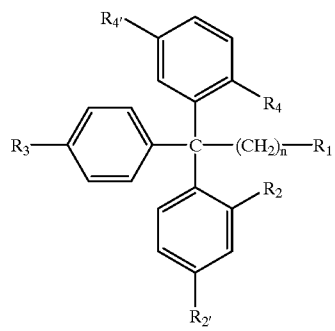

(II)

wherein:

n is 0, 1, 2, 3 or 4;

$R_1$ is —H, —OR, —SR, —CN, —C(O)R, —C(O)OR, —C(O)NR$_2$, —CH[C(O)R]$_2$ or —CH[C(O)OR]$_2$;

$R_2$ is —F, —Cl, —Br, —I, —OR, —SR, —C(O)R or —C(O)NR$_2$;

$R_{2'}$ is —H or —NO$_2$;

$R_3$ is —H, (C$_1$–C$_6$) alkyl, (C$_1$–C$_6$) alkenyl, (C$_1$–C$_6$) alkynyl, —OR or —SR;

$R_4$ is —H or —NR$_2$;

$R_{4'}$ is —H, —F, —Cl, —Br or —I; and each R is independently selected from the group consisting of —H, (C$_1$–C$_6$) alkyl, (C$_1$–C$_6$) alkenyl, (C$_1$–C$_6$) alkynyl or (C$_1$–C$_6$) alkoxy.

Exemplary preferred compounds according to formula (II) include the following: 6, 14, 15, 17, 20, 27, 32, 33, 36, 42, 45, 49, 55, 70, 75, 79, 80, 81, 82, 83, 84, 85 and 86.

Invention are compounds having the he compounds of the invention are compounds having the structural formula:

(III)

$$R_3—Ar_3—\underset{\underset{R_2}{|}}{\overset{\overset{R_4}{|}}{\underset{|}{\overset{Ar_1}{\underset{|}{X}}}}}—(CH_2)_{\overline{n}}—R_1$$

wherein:

X is absent or —C≡C—;

Y is C, P, Si or Ge;

n is 0, 1, 2, 3 or 4;

Ar$_1$ is phenyl, substituted phenyl, cycloalkyl or heteroarylium other than imidazolium, nitroimidazolium or triazolium;

Ar$_3$ is phenyl, naphthyl, piperidyl or cyclohexyl;

$R_1$ is —R, —OR, —SR, —CN, —NR$_2$, —ONR$_2$, —C(O)R, —C(O)OR, —C(O)NR$_2$, —CH[C(O)R]$_2$, —CH[C(O)OR]$_2$, (C$_1$–C$_6$) alkyl, (C$_1$–C$_6$) alkenyl, (C$_1$–C$_6$) alkynyl, cyclopenta-2,4-diene-1-ylidene or phenyl;

each of $R_2$, $R_3$ and $R_4$ is independently selected from the group consisting of —H, —F, —Cl, —Br, —I, —OR, —SR, —NR$_2$, —NO$_2$, —C(O)R, —C(O)OR, —C(O)NR$_2$, trihalomethyl, (C$_1$–C$_6$) alkyl, (C$_1$–C$_6$) alkenyl, (C$_1$–C$_6$) alkynyl and phenyl;

each R is independently selected from the group consisting of —H, halo, (C$_1$–C$_6$) alkyl, substituted (C$_1$–C$_6$) alkyl, (C$_1$–C$_6$) alkenyl, substituted (C$_1$–C$_6$) alkenyl, (C$_1$–C$_6$) alkynyl, substituted (C$_1$–C$_6$) alkynyl and (C$_1$–C$_6$) alkoxy;

the alkyl, alkenyl or alkynyl substituents are each independently selected from the group consisting of aryl, —C(O)OR, pyrrolidinyl, butyrolactonyl, —F, —Cl, —Br, —I and —CN; and the phenyl substituents are each independently —R.

Exemplary preferred compounds according to formula (III) include the following: 7, 10, 12, 13, 16, 18, 19, 21, 22, 23, 24, 26, 28, 29, 30, 31, 34, 35, 37, 38, 40, 41, 43, 44, 46, 47, 48, 50, 51, 52, 53, 54, 56, 58, 59, 60, 61, 62, 64, 65, 67, 68, 69, 71, 72, 73, 78, 87, 88, 89 and 90.

The chemical formulae referred to herein may exhibit the phenomena of tautomerism or conformational isomerism. As the formulae drawings within this specification can represent only one of the possible tautomeric or conformational isomeric forms, it should be understood that the invention encompasses any tautomeric or conformational isomeric forms which exhibit biological or pharmacological activity as described herein.

The compounds of the invention may be in the form of free acids, free bases or pharmaceutically effective salts thereof. Such salts can be readily prepared by treating a compound with an appropriate acid. Such acids include, by way of example and not limitation, inorganic acids such as hydrohalic acids (hydrochloric, hydrobromic, etc.), sulfuric acid, nitric acid, phosphoric acid, etc.; and organic acids such as acetic acid, propanoic acid, 2-hydroxyacetic acid, 2-hydroxypropanoic acid, 2-oxopropanoic acid, propandioic acid, butandioic acid, etc. Conversely, the salt can be converted into the free base form by treatment with alkali.

In addition to the above-described compounds and their pharmaceutically acceptable salts, the invention may employ, where applicable, solvated as well as unsolvated forms of the compounds (e.g. hydrated forms).

The compounds described herein may be prepared by any processes known to be applicable to the preparation of chemical compounds. Suitable processes are well known in the art. Preferred processes are illustrated by the representative examples. Necessary starting materials may be obtained commercially or by standard procedures of organic chemistry. Moreover, many of the compounds are commercially available.

An individual compound's relevant activity and potency as an agent to affect sickle cell dehydration or deformation and/or mammalian cell proliferation may be determined using standard techniques. Preferentially, a compound is subject to a series of screens to determine its pharmacological activity.

In most cases, the active compounds of the invention exhibit two pharmacological activities: inhibition of the Gardos channel of erythrocytes and inhibition of mammalian cell proliferation. However, in some cases, the compounds of the invention may exhibit only one of these pharmacological activities. Any compound encompassed by formula (I) which exhibits at least one of these pharmacological activities is considered to be within the scope of the present invention.

In general, the active compounds of the invention are those which induce at least about 25% inhibition of the Gardos channel of erythrocytes (measured at about 10 $\mu$M) and/or about 25% inhibition of mammalian cell proliferation (measured at about 10 $\mu$M), as measured using in vitro assays that are commonly known in the art (see, e.g., Brugnara et al., 1993, *J. Biol. Chem.* 268(12):8760–8768; Benzaquen et al., 1995, *Nature Medicine* 1:534–540). Alternatively, or in addition, the active compounds of the invention generally will have an $IC_{50}$ (concentration of compound that yields 50% inhibition) for inhibition of the Gardos channel of less than about 10 $\mu$M and/or an $IC_{50}$ for inhibition of cell proliferation of less than about 10 $\mu$M, as measured using in vitro assays that are commonly known in the art (see, e.g., Brugnara et al., 1993, *J. Biol. Chem.* 268(12):8760–8768; Benzaquen et al., 1995, *Nature Medicine* 1:534–540).

Representative active compounds according to the invention are those listed in TABLE A, supra.

In certain embodiments of the invention, compounds which exhibit only one pharmacological activity, or a higher degree of one activity, may be preferred. Thus, when the compound is to be used in methods to treat or prevent sickle cell disease, or in methods to reduce sickle cell dehydration and/or delay the occurrence of erythrocyte sickling or deformation in situ, it is preferred that the compound exhibit at least about 75% Gardos channel inhibition (measured at about 10 $\mu$M) and/or have an $IC_{50}$ of Gardos channel inhibition of less than about 1 $\mu$M, with at least about 90% inhibition and/or an $IC_{50}$ of less than about 0.1 $\mu$M being particularly preferred.

Exemplary preferred compounds for use in methods related to Gardos channel inhibition and sickle cell disease include compound numbers 6, 7, 10, 12, 13, 14, 15, 16, 17, 18, 20, 21, 22, 23, 24, 27, 29, 30, 31, 32, 33, 34, 35, 37, 38, 42, 43, 44, 45, 46, 47, 49, 50, 51, 52, 53, 55, 56, 58, 59, 60, 62, 64, 65, 67, 68, 69, 70, 73, 75, 78, 79, 80, 81, 82, 83, 85, 86, 87, 88 and 90.

Exemplary particularly preferred compounds for use in methods related to Gardos channel inhibition and sickle cell disease include compound numbers 6, 14, 15, 16, 32, 37, 43, 46, 55, 62, 64, 69, 75, 79, 82, 87 and 90.

When the compound is to be used in methods to treat or prevent disorders characterized by abnormal cell proliferation or in methods to inhibit cell proliferation in situ, it is preferable that the compound exhibit at least about 75% inhibition of mitogen-induced cell proliferation (measured at about 10 $\mu$M) and/or have an $IC_{50}$ of cell proliferation of less than about 3 $\mu$M, with at least about 90% inhibition and/or an $IC_{50}$ of less than about 1 $\mu$M being particularly preferred.

Exemplary preferred compounds for use in methods inhibiting mammalian cell proliferation or for the treatment or prevention of diseases characterized by abnormal cell proliferation include compound numbers 13, 14, 15, 16, 17, 18, 19, 21, 26, 27, 28, 30, 31, 36, 38, 40, 41, 42, 43, 45, 46, 47, 48, 49, 50, 52, 54, 59, 61, 65, 67, 68, 70, 71, 72, 73, 79, 82, 83, 84, 85, 86, 89 and 90.

Exemplary particularly preferred compounds for use in methods of inhibiting mammalian cell proliferation or for the treatment or prevention of diseases characterized by abnormal cell proliferation include compound numbers 16, 28, 30, 36, 43, 45, 47, 48, 49, 50, 54 and 84.

Certain compounds of formula (I) are commercially available. For example, compound numbers 1, 2, 3, 4, 5, 6, 7, 8, 9, 10, 11, 12, 19, 20, 21, 23, 24, 25, 26, 28, 34, 37, 38, 39, 42, 43, 44, 45, 46, 47, 48, 49, 50, 51, 52, 54, 57, 59, 60, 61, 62, 66, 67, 69, 71, 72, 73, 76, 77 and 87 are commercially available. However, no biological activity has been reported for these compounds (see, e.g., Hanessian et al., 1976, *Methods Carbohydr. Chem.* 7:63; Paike, 1992, *Mater. Sci.* 18:53–57, Liu & Paike, 1987, *Tetrahedron Lett.* 28(3):3763–3766; Tomioka et al., 1981, *Chem. Lett.* 11:1621–1624; Glidewell et al., 1994, *Acta Crystallogr., Sect C: Cryst. Struct. Commun.* C50:1362–1366; Ponnuswamy et al., 1984, *Acta Crystallogr., Sect C: Cryst. Struct. Commun.* C40(1):142–144; Lewis et al., 1980, *J. Am. Chem. Soc.* 102(14):4659–4664 and CA 083:018922; Illes et al., 1988, *Acta Phytopathologica et Entomologia Hungarica* 23:243–255; and Matsuura et al., 1991, *Biochem. Pharmacol.* 41:1949–1956).

Apart from the inventions disclosed and claimed herein, additional active compounds of formula (I) for which no biological activity has been previously reported include Compound 13 (U.S. Pat. No. 4,006,023); Compound 25 (WO 96/36631); Compound 26 (Fan et al., 1983, *Yiyao Gongye* 9:2–4); Compound 60 (Ethridge et al., 1990, *J. Production Agriculture* 3(2):246–252); Compound 76 (CAS No. 18740-94-8); Compound 77 (Ferguson et al., 1992, *Acta Crystallogr., Sect. C: Cryst. Struct. Commun.* C48(7):1228–1231); and Compound 90 (1957, *Comptes. Rendus.* 245(1):73–75).

Apart from the inventions disclosed and claimed herein, other compounds of formula (I) for which no biological activity has been reported include 1,1-diphenyl-1-(2-hydroxynaphthyl)-methanol (Lewis et al., 1980, *J. Am. Chem. Soc.* 102(14):4659–4664; CA 083:018922); 1,1-diphenyl-1-(pyrid-2-yl)-methanol, 1-(4-chlorophenyl)-1-phenyl-1-(pyrid-2-yl)-methanol, 1-(4-methoxyphenyl)-1-phenyl-1-(pyrid-3-yl)-methanol and 1,1-di-(4-methoxyphenyl)-1-(pyrid-3-yl)-methanol (Illes et al., 1988, *Acta Phytopathologica et Entomologia Hungarica* 23:243–255); 1,1,1-triphenyl-1-aminomethane and 1,1-diphenyl-1-(N-pyridyl)-methane (Matsuura et al., 1991, *Biochem. Pharmacol.* 41:1949–1956); 4,4'-dimethoxytrityl chloride, pixyl chloride, di-o-anisyl-1-naphthyl-methyl chloride and p-anisyl-1-naphthyl-methyl chloride (Gait, 1984, *Oligonucleotide Synthesis: A Practical Approach*, IRL Press, Oxford).

Additionally, Compounds 6, 17 and 85 are known metabolites of Clotrimazole (Duhm et al., 1974, *Postgraduate Medical Journal July Suppl.*:13–16). However, unlike Clotrimazole, no biological or pharmacological activity has been reported for these compounds. For example, unlike Clotrimazole, Compound 6 does not induce hepatic microsomal cytochrome P450 in rats (Matsuura et al., 1991, *Biochem. Pharmacol.* 41:1949–1956).

The pharmaceutical compositions of the invention embrace all of the compounds of formula (I). Certain compounds of formula (I) which are included in the invention apart from any pharmaceutical excipients, carriers or diluents are represented by formulae (A), (B) and (C), below.

In a preferred embodiment, compounds of the invention are compounds having the formula:

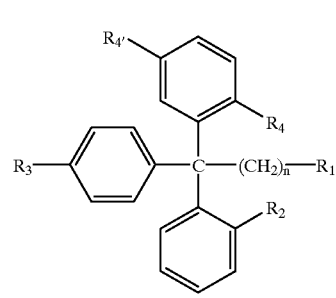

(A)

or pharmaceutically acceptable salts or hydrates thereof, wherein:

n is 0, 1, 2, 3 or 4;

$R_1$ is —H, —OR, —SR, —CN, —C(O)R, —C(S)R, —C(O)OR, —C(S)OR, —C(O)SR, —C(S)SR, —C(O)NR$_2$, —C(S)NR$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$;

$R_2$ is —F, —Cl, —Br or —I;

$R_3$ is —R, —OR or —SR;

$R_{4'}$ is —H or —NR$_2$;

$R_4$ is —H, —F, —Cl, —Br or —I; and each R is independently selected from the group consisting of —H, $(C_1-C_6)$ alkyl, $(C_1-C_6)$ alkenyl, $(C_1-C_6)$ alkynyl and $(C_1-C_6)$ alkoxy.

In another preferred embodiment, the compounds of the invention are those of formula (A), with the provisos that (i) when n is 0 and $R_1$ is —H or —OH, $R_3$ is other than —H; and (ii) when n is 0 and $R_1$ is —H, $R_3$ is other than —OH.

In another preferred embodiment, the compounds of the invention are those of formula (A), with the proviso that when n is 0 and $R_1$ is —C(O)NH$_2$, $R_2$ is other than —F.

Representative compounds according to formula (A) include Compounds 14, 15, 32, 33, 36, 55, 70, 75, 79, 80, 81, 82, 83, 84 and 86.

In another preferred embodiment, the compounds of the invention are compounds having the formula:

(B)

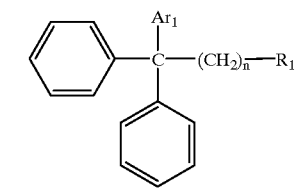

or pharmaceutically acceptable salts or hydrates thereof, wherein:

n is 0, 1, 2, 3 or 4;

$R_1$ is —NR$_2$, —C(O)R, —C(S)R, —C(O)NR'$_2$ or —C(S)NR'$_2$;

$R_2$ is —F, —Cl, —Br or —I;

$R_3$ is —F, —Cl, —Br or —I;

$R_4$ is —F, —Cl, —Br or —I;

each R is independently selected from the group consisting of —H, $(C_1-C_6)$ alkyl, $(C_1-C_6)$ alkenyl, $(C_1-C_6)$ alkynyl and $(C_1-C_6)$ alkoxy; and each R' is independently selected from the group consisting of —H, $(C_1-C_6)$ alkyl, $(C_1-C_6)$ alkenyl, $(C_1-C_6)$ alkynyl and $(C_1-C_6)$ alkoxy.

Representative preferred compounds according to formula (B) include Compounds 30, 40, 41 and 65.

In another preferred embodiment, the compounds of the invention are compounds having the formula:

(C)

or pharmaceutically acceptable salts or hydrates thereof, wherein:

n is 0, 1, 2, 3 or 4;

Ar$_1$ is phenyl or cyclohexyl;

$R_1$ is —NR$_2$, —CH[C(O)OR]$_2$, —CH[C(S)OR]$_2$, —CH[C(O)SR]$_2$, —CH[C(S)SR]$_2$, —C(O)NR$_2$ or —C(S)NR$_2$; and each R is independently selected from the group consisting of —H, ($C_1$–$C_6$) alkyl, ($C_1$–$C_6$) alkenyl, ($C_1$–$C_6$) alkynyl and ($C_1$–$C_6$) alkoxy.

In another preferred embodiment, the compounds of the invention are those of formula (C), with the proviso that when $R_1$ is —$NH_2$ or —C(O)$NH_2$, n is 1, 2 or 3.

Representative preferred compounds according to formula (C) include compounds 18, 29, 31, 56 and 78.

5.2 Formulation and Routes of Administration

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from sickle cell disease, the compounds of the invention can be administered in cocktails containing agents used to treat the pain, infection and other symptoms and side effects commonly associated with sickle cell disease. Such agents include, e.g., analgesics, antibiotics, etc. The compounds can also be administered in cocktails containing other agents that are commonly used to treat sickle cell disease, including butyrate and butyrate derivatives (Perrine et al., 1993, *N. Engl. J. Med.* 328(2):81–86); hydroxyurea (Charache et al., 1995, *N. Engl. J. Med.* 323(20):1317–1322); erythropoietin (Goldberg et al, 1990, *N. Engl. J. Med.* 323(6): 366–372); and dietary salts such as magnesium (De Franceschi et al., 1996, *Blood* 88(648a):2580).

When administered to a patient undergoing cancer treatment, the compounds may be administered in cocktails containing other anti-cancer agents and/or supplementary potentiating agents. The compounds may also be administered in cocktails containing agents that treat the side-effects of radiation therapy, such as anti-emetics, radiation protectants, etc.

Anti-cancer drugs that can be co-administered with the compounds of the invention include, e.g., Aminoglutethimide; Asparaginase; Bleomycin; Busulfan; Carboplatin; Carmustine (BCNU); Chlorambucil; Cisplatin (cis-DDP); Cyclophosphamide; Cytarabine HCl; Dacarbazine; Dactinomycin; Daunorubicin HCl; Doxorubicin HCl; Estramustine phosphate sodium; Etoposide (VP-16); Floxuridine; Fluorouracil (5-FU); Flutamide; Hydroxyurea (hydroxycarbamide); Ifosfamide; Interferon Alfa-2a, Alfa 2b, Lueprolide acetate (LHRH-releasing factor analogue); Lomustine (CCNU); Mechlorethamine HCl (nitrogen mustard); Melphalan; Mercaptopurine; Mesna; Methotrexate (MTX); Mitomycin; Mitotane (o.p'-DDD); Mitoxantrone HCl; Octreotide; Plicamycin; Procarbazine HCl; Streptozocin; Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bis-guanylhydrazone; MGBG); Pentostatin; Semustine (methyl-CCNU); Teniposide (VM-26); paclitaxel and other taxanes; and Vindesine sulfate.

Supplementary potentiating agents that can be co-administered with the compounds of the invention include, e.g., Tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{++}$ antagonists (e.g., verapamil, nifedipine, nitrendipine and caroverine); Amphotericin (e.g., Tween 80 and perhexiline maleate); Triparanol analogues (e.g., tamoxifen); antiarrhythmic drugs (e.g., quinidine); antihypertensive drugs (e.g., reserpine); Thiol depleters (e.g., buthionine and sulfoximine); and calcium leucovorin.

The active compound(s) may be administered per se or in the form of a pharmaceutical composition wherein the active compound(s) is in admixture with one or more pharmaceutically acceptable carriers, excipients or diluents. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

5.3 Effective Dosages

Pharmaceutical compositions suitable for use with the present invention include compositions wherein the active ingredient is contained in a therapeutically effective amount, i.e., in an amount effective to achieve its intended purpose. Of course, the actual amount effective for a particular application will depend, inter alia, on the condition being treated. For example, when administered in methods to reduce sickle cell dehydration and/or delay the occurrence of erythrocyte sickling or distortion in situ, such compositions will contain an amount of active ingredient effective to achieve this result. When administered in methods to inhibit cell proliferation, such compositions will contain an amount of active ingredient effective to achieve this result. When administered to patients suffering from sickle cell disease or disorders characterized by abnormal cell proliferation, such compositions will contain an amount of active ingredient effective to, inter alia, prevent the development of or alleviate the existing symptoms of, or prolong the survival of, the patient being treated. For use in the treatment of cancer, a therapeutically effective amount further includes that amount of compound which arrests or regresses the growth of a tumor. Determination of an effective amount is well within the capabilities of those skilled in the art, especially in light of the detailed disclosure herein.

For any compound described herein the therapeutically effective amount can be initially determined from cell culture arrays. Target plasma concentrations will be those concentrations of active compound(s) that are capable of inducing at least about 25% inhibition of the Gardos channel and/or at least about 25% inhibition of cell proliferation in cell culture assays, depending, of course, on the particular desired application. Target plasma concentrations of active compound(s) that are capable of inducing at least about 50%, 75%, or even 90% or higher inhibition of the Gardos channel and/or cell proliferation in cell culture assays are preferred. The percentage of inhibition of the Gardos channel and/or cell proliferation in the patient can be monitored to assess the appropriateness of the plasma drug concentration achieved, and the dosage can be adjusted upwards or downwards to achieve the desired percentage of inhibition.

Therapeutically effective amounts for use in humans can also be determined from animal models. For example, a dose for humans can be formulated to achieve a circulating concentration that has been found to be effective in animals. A particularly useful animal model for sickle cell disease is the SAD mouse model (Trudel et al., 1991, *EMBO J.* 11:3157–3165). Useful animal models for diseases characterized by abnormal cell proliferation are well-known in the art. In particular, the following references provide suitable animal models for cancer xenografts (Corbett et al., 1996, *J. Exp. Ther. Oncol.* 1:95–108; Dykes et al., 1992, *Contrib. Oncol. Basel. Karger* 42:1–22), restenosis (Carter et al., 1994, *J. Am. Coll. Cardiol.* 24(5):1398–1405), atherosclerosis (Zhu et al., 1994, *Cardiology* 85(6):370–377) and neovascularization (Epstein et al., 1987, Cornea 6(4):250–257). The dosage in humans can be adjusted by monitoring Gardos channel inhibition and/or inhibition of cell proliferation and adjusting the dosage upwards or downwards, as described above.

A therapeutically effective dose can also be determined from human data for compounds which are known to exhibit similar pharmacological activities, such as Clotrimazole and other antimycotic agents (see, e.g., Brugnara et al., 1995, *JPET* 273:266–272; Benzaquen et al., 1995, *Nature Medicine* 1:534–540; Brugnara et al., 1996, *J. Clin. Invest.* 97(5):1227–1234). The applied dose can be adjusted based on the relative bioavailability and potency of the administered compound as compared with Clotrimazole.

Adjusting the dose to achieve maximal efficacy in humans based on the methods described above and other methods as are well-known in the art is well within the capabilities of the ordinarily skilled artisan.

Of course, in the case of local administration, the systemic circulating concentration of administered compound will not be of particular importance. In such instances, the compound is administered so as to achieve a concentration at the local area effective to achieve the intended result.

For use in the prophylaxis and/or treatment of sickle cell disease, including both chronic sickle cell episodes and acute sickle cell crisis, a circulating concentration of administered compound of about 0.001 μM to 20 μM is considered to be effective, with about 0.1 μM to 5 μM being preferred.

Patient doses for oral administration of the compounds described herein, which is the preferred mode of administration for prophylaxis and for treatment of chronic sickle cell episodes, typically range from about 80 mg/day to 16,000 mg/day, more typically from about 800 mg/day to 8000 mg/day, and most typically from about 800 mg/day to 4000 mg/day. Stated in terms of patient body weight, typical dosages range from about 1 to 200 mg/kg/day, more typically from about 10 to 100 mg/kg/day, and most typically from about 10 to 50 mg/kg/day. Stated in terms of patient body surface areas, typical dosages range from about 40 to 8000 mg/m$^2$/day, more typically from about 400 to 4000 mg/m$^2$/day, and most typically from about 400 to 2000 mg/m$^2$/day.

For use in the treatment of disorders characterized by abnormal cell proliferation, including cancer, arteriosclerosis and angiogenic conditions such as restenosis, a circulating concentration of administered compound of about 0.001 μM to 20 μM is considered to be effective, with about 0.1 μM to 5 μM being preferred.

Patient doses for oral administration of the compounds described herein for the treatment or prevention of cell proliferative disorders typically range from about 80 mg/day to 16,000 mg/day, more typically from about 800 mg/day to 8000 mg/day, and most typically from about 800 mg/day to 4000 mg/day. Stated in terms of patient body weight, typical dosages range from about 1 to 200 mg/kg/day, more typically from about 10 to 100 mg/kg/day, and most typically from about 10 to 50 mg/kg/day. Stated in terms of patient body surface areas, typical dosages range from about 40 to 8000 mg/m$^2$/day, more typically from about 400 to 4000 mg/m$^2$/day, and most typically from about 400 to 2000 mg/m$^2$/day.

For other modes of administration, dosage amount and interval can be adjusted individually to provide plasma levels of the administered compound effective for the particular clinical indication being treated. For example, if acute sickle crises are the most dominant clinical manifestation, a compound according to the invention can be administered in relatively high concentrations multiple times per day. Alternatively, if the patient exhibits only periodic sickle cell crises on an infrequent or periodic or irregular basis, it may be more desirable to administer a compound of the invention at minimal effective concentrations and to use a less frequent regimen of administration. This will provide a therapeutic regimen that is commensurate with the severity of the sickle cell disease state.

For use in the treatment of tumorigenic cancers, the compounds can be administered before, during or after surgical removal of the tumor. For example, the compounds can be administered to the tumor via injection into the tumor mass prior to surgery in a single or several doses. The tumor, or as much as possible of the tumor, may then be removed surgically. Further dosages of the drug at the tumor site can be applied post removal. Alternatively, surgical removal of as much as possible of the tumor can precede administration of the compounds at the tumor site.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the clinical symptoms demonstrated by the particular patient. Of course, many factors are important in determining a therapeutic regimen suitable for a particular indication or patient. Severe indications such as cancer may warrant administration of higher dosages as compared with less severe indications such as sickle cell disease.

5.4 Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds which exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, In: *The Pharmacological Basis of Therapeutics*, Ch. 1 p1).

The invention having been described, the following examples are intended to illustrate, not limit, the invention.

6. EXAMPLE

Compound Syntheses

This Example demonstrates general methods of synthesis for many of the preferred compounds of the invention, as well as preferred methods of synthesis for certain exemplary compounds of the invention.

6.1 Synthesis of Triphenylmethanols

A general method of synthesis of triphenylmethanol derivatives is as follows: A mixture of substituted benzoyl chloride (1 equivalent), substituted benzene (1 equivalent), and aluminum chloride (1.1 equivalent), in methylene chloride was stirred at room temperature for 1 hour. The reaction mixture was cooled in an ice bath and water was added. The layers were separated and the aqueous layer extracted with methylene chloride. The combined methylene chloride extracts were washed with water and saturated aqueous sodium bicarbonate and then dried over sodium sulfate. Evaporation of the solvent gave the substituted benzophenone in 80–95% yield. The substituted benzophenone (1 equivalent) and substituted phenylmagnesium bromide (1.1 equivalent) in tetrahydrofuran was refluxed for 5 hours, cooled in an ice bath and water added. The reaction mixture was extracted with methylene chloride and the combined extracts were dried over sodium sulfate. Evaporation of the solvent followed by column chromatography gave the substituted triphenylmethanol in 45–90% yield.

6.2 Synthesis of Triphenylpropionic Acids 6.2.1 Method A

One method of synthesis of triphenylpropionic acid derivatives is as follows: A mixture of substituted triphenylmethanol (1 equivalent) and malonic acid (2–3 equivalents) was stirred without solvent at 170° C. for 3 hour. After cooling, aqueous 1.0 M sodium hydroxide was added to the reaction mixture. This mixture was stirred at 90° C. for 4 hours and then filtered hot. Acidification of the cooled filtrate with 1.0 M hydrochloric acid caused precipitation of a white product which was collected by suction filtration in 20–40% yield.

6.2.2 Method B

A second method of synthesis of triphenylpropionic acid derivatives is as follows: A mixture of magnesium (1.1 equivalent) and diethyl malonate (1.1 equivalent) in anhydrous ethanol was heated at reflux until all the magnesium was consumed (approximately 2 hours). Evaporation of the solvent gave a clear oil to which substituted triphenylmethane (obtained by reduction of the substituted triphenylmethanol by the method of Ando & Ikeno, 1979, *Tetrahedron. Lett.* 51:4941) (1 equivalent) and benzene was added. The mixture was refluxed for 5 minutes and then stirred at ambient temperature for 3 hours. Hydrochloric acid (0.1 M) was added and the mixture stirred at room temperature overnight. The organic layer was separated, washed with water and dried over sodium sulfate. Evaporation gave the intermediate diethyl-substituted-diphenyl-benzylmalonate in 50–90% yield. In the final step, this intermediate (1 equivalent) and potassium hydroxide (6 equivalents) in ethanol was refluxed for 9 hours. The solvent was removed in vacuo, water added, and the solution stirred at 65° C. for 1 hour. The cooled solution was acidified with 1.0 M hydrochloric acid causing precipitation of a white solid. The solid was collected by suction filtration to give the desired substituted triphenylpropionic acid in 60–90% yield.

6.3 Synthesis of 2-Chlorophenyl-diphenylmethanol

A preferred method of synthesis of 2-chlorophenyl-diphenylmethanol (Compound 6) is as follows: A mixture of 25 g (0.073 mole) of Clotrimazole in 100 mL of 1.0M HCl was refluxed for 2.5 hours. After cooling to room temperature the mixture was extracted wit- ethyl acetate and the combined organics dried over sodium sulfate. The solvent was removed in vacuo and the residue crystallized from hexane to give 19.5 g (91% yield) of a yellow crystalline product having a melting point of 92–93.5° C.

The product gave the following analytical data: NMR (CDCl$_3$): δ 4.48 ppm (1H, s, OH); δ 6.70 ppm (1H, d, J=7 Hz, aryl); δ 7.13 ppm (1H, t, J=8 Hz, aryl); δ 7.28 ppm (5H, m, aryl); δ 7.34 ppm (6H, m, aryl); δ 7.52 ppm (1H, d, J=9 Hz, aryl).

Anal. C$_{19}$H$_{15}$ClO (CH calculated: 77.42, 5.13; found: 77.33, 5.17).

6.4 Synthesis of (2-Chlorophenyl)-diphenylacetonitrile

A preferred method of synthesis of (2-chlorophenyl)-diphenylacetonitrile (Compound 14) is as follows: A mixture of 1 g (0.003 mole) of chloro-(2-chlorophenyl)-diphenylmethane and 0.3 g (0.004 mole) of copper cyanide was heated for 2 hours at 150° C. without solvent. The mixture was allowed to cool slightly, 10 mL of toluene added, the mixture filtered, and the solvent removed in vacuo. The resulting brown solid was crystallized from 2-propanol to give 0.64 g (66% yield) of a light brown crystalline product having a melting point of 145–147° C.

The product gave the following analytical data: NMR (CDCl$_3$): δ 6.58 ppm (1H, d, J=8 Hz, aryl); δ 7.16 ppm (1H, t, J=10 Hz, aryl); δ 7.24 ppm (4H, m, aryl); δ 7.32 ppm (1H, d, J=7 Hz, aryl); δ 7.37 ppm (6H, m, aryl); δ 7.48 ppm (1H, d, J=8 Hz, aryl).

Anal. C$_{20}$H$_{14}$ClN (CHNCl calculated: 79.07, 4.65, 4.61, 11.67; found: 79.08. 4.72, 4.58, 11.58).

6.5 Synthesis of 2-Chlorophenyl-diphenylacetaldehyde

A preferred method of synthesis of 2-chlorophenyl-diphenylacetaldehyde (Compound 15) is as follows: A mixture of 7.5 g (0.025 mole) of 2-chlorophenyl-diphenylacetonitrile, and 56 mL (0.056 mole) of DIBAL-H in 100 mL of toluene was stirred for 1 hour at −78° C. Ethyl acetate (7 mL), silica gel (65 g), and water (5 mL) was added and the mixture stirred at −78° C. for 2 hours. The mixture was then allowed to warm to room temperature and stirred at room temperature for 4 hours. Ethyl acetate (200 mL) was added and the mixture filtered. The organic layer was dried over sodium sulfate and the solvent removed in vacuo. The resulting solid was crystallized from 2-propanol to give 6.0 g (77% yield) of a white crystalline product having a melting point of 126–129° C.

The product gave the following analytical data: NMR (CDCl$_3$): δ 6.69 ppm (1H, d, J=9 Hz, aryl); δ 7.13 ppm (2H, d, J=9 Hz, aryl); δ 7.19 ppm (1H, d, J=6 Hz, aryl); δ 7.26 ppm (1H, s, aryl); δ 7.28 ppm (1H, d, J=8 Hz, aryl); δ 7.36 ppm (7H, m, aryl); δ 7.46 ppm (1H, d, J=9 Hz, aryl); δ 10.49 ppm (1H, s, CHO).

Anal. C$_{20}$H$_{15}$ClO (CHCl calculated: 78.30, 4.93, 11.56; found: 77.90. 5.28, 11.39).

6.6 Synthesis of Triphenylacetaldehyde

A preferred method of synthesis of triphenylacetaldehyde (Compound 16) is as follows: A mixture of 1 g (0.003 mole) of 2-chlorophenyl-diphenylacetonitrile, and 8 mL (0.008 mole) of DIBAL-H in 15 mL of toluene was stirred for 1 hour at −78° C. Ethyl acetate (4 mL), silica gel (10 g), and water (0.5 mL) was added and the mixture stirred at −78° C. for 30 min. The mixture was then allowed to warm to room temperature and stirred at room temperature for 4 hours. Ethyl acetate (100 mL) was added and the mixture filtered. The organic layer was dried over sodium sulfate. Evaporation gave 0.9 g (95% yield) of a white powder having a melting point of 91–96° C.

The product gave the following analytical data: NMR (CDCl$_3$): δ 7.05 ppm (6H, d, J=9 Hz, aryl); δ 7.44 ppm (9H, m, aryl); δ 10.28 ppm (1H, s, CHO).

Anal. C$_{20}$H$_{15}$O (CH calculated: 88.20, 5.92; found: 88.06, 5.99).

6.7 Synthesis of 2-Chlorophenyl-diphenylmethane

A preferred method of synthesis of 2-chlorophenyl-diphenylmethane (Compound 17) is as follows: A mixture of 5 g (0.017 mole) of 2-chlorophenyl-diphenylmethanol (Compound 6), 15 g (0.1 mole) of sodium iodide, 12.7 mL (0.1 mole) of chlorotrimethylsilane and 5 mL (0.1 mole) acetonitrile in 30 mL of dichloromethane was stirred at room temperature for 2 days. The reaction mixture was diluted with 50 mL of water and extracted with ethyl acetate. The combined organics were dried over sodium sulfate and the solvent removed in vacuo. The resultant oil was passed through a silica gel column using ethyl acetate:hexane (1:5) as eluent. The first fraction collected contained the product which was obtained as a solid after removal of the solvent in vacuo. This solid was crystallized from ethanol/water to give 3.67 g (78% yield) of a white crystalline product having a melting point of 74–76° C.

The product gave the following analytical data: NMR (DMSO-d$_6$) δ 5.91 ppm (1H, s, CH); δ 6.92 ppm (1H, d, J=9 Hz, aryl); δ 7.06 ppm (4H, d, J=8 Hz, aryl); δ 7.24 ppm (8H, m, aryl); δ 7.48 ppm (1H, d, J=9 Hz, aryl).

Anal. C$_{19}$H$_{15}$Cl (CH calculated: 81.86, 5.42; found: 81.69, 5.51).

6.8 Synthesis of Tris(4-chlorophenyl)propionamide

A preferred method of synthesis of tris(4-chlorophenyl) propionamide (Compound 30) is as follows: A mixture of 5.2 g (0.012 mole) of tris(4-chlorophenyl)propionic acid chloride in 25 mL of tetrahydrofuran was cooled to 0–5° C. and 25 mL of ammonium hydroxide (0.4 mole NH$_3$) was added. The solution was stirred at 0–5° C. for 15 minutes and then extracted with ethyl acetate (5×25 mL). The combined organics were dried over magnesium sulfate. Evaporation gave 4.5 g (91% yield) of an off-white powder which was crystallized from hexane to give 3.7 g (74% yield) of a white powder having a melting point of 158–160° C.

The product gave the following analytical data: NMR (CDCl$_3$): δ 3.50 ppm (2H, s, CH$_2$); δ 4.91 ppm (1H, s, NH$_2$); δ 5.29 ppm (1H, s, NH$_2$); δ 7.15 ppm (6H, d, J=8 Hz, aryl); δ 7.26 ppm (6H, d, J=8 Hz, aryl).

Anal. C$_{21}$H$_{16}$Cl$_3$NO (CHNCl calculated: 62.53, 4.00, 3.47, 26.03; found: 62.31, 4.03, 3.45, 26.20).

6.9 Synthesis of (2-Fluorophenyl)-diphenylacetonitrile

A preferred method of synthesis of (2-fluorophenyl)-diphenylacetonitrile (Compound 32) is as follows: A mixture of 0.5 g (0.002 mole) of chloro-(2-fluorophenyl)-diphenylmethane and 0.15 g (0.002 mole) of copper cyanide was heated for 2 hours at 150° C. without solvent. The mixture was allowed to cool slightly, 10 mL of toluene added, the mixture filtered, and the solvent removed in vacuo. The resulting off-white solid was crystallized from 2-propanol to give 0.31 g (64% yield) of a clear crystalline product having a melting point of 144–145° C.

The product gave the following analytical data: NMR (CDCl$_3$): δ 6.67 ppm (1H, t, J=9 Hz, aryl); δ 7.03–7.17 ppm (4H, m, aryl); δ 7.24 ppm (3H, m, aryl); δ 7.48 ppm (6H, m, aryl).

Anal. C$_{20}$H$_{14}$FN (CHN calculated: 83.60, 4.91, 4.87; found: 83.41. 4.97, 4.84).

6.10 Synthesis of 3-(2-Chlorophenyl)-3,3-diphenylpropionic Acid

A preferred method of synthesis of 3-(2-chlorophenyl)-3,3-diphenylpropionic acid (Compound 36) is as follows: A mixture of 1.7 g (0.07 mole) of magnesium and 11.2 g (0.07 mole) of diethyl malonate in 25 mL anhydrous ethanol was heated at reflux until all the magnesium was consumed (approximately 2 hours). Evaporation of the solvent gave a clear oil to which 20 g (0.064) of chloro-(2-chlorophenyl)-diphenylmethane and 100 mL benzene was added. The mixture was refluxed for 5 minutes and then stirred at ambient temperature for 3 hours. Water (90 mL) and 10 mL of 1.0 M hydrochloric acid was added and the mixture stirred at room temperature for 14 hours. The organic layer was separated, washed with water and dried over sodium sulfate. Evaporation gave 14.6 g (51% yield) of pale yellow solid. In the final step, 12.5 g (0.028 mole) of this solid and 9.5 g (0.17 mole) potassium hydroxide in 100 mL of ethanol refluxed for 9 hours. The solvent was removed in vacuo, 400 mL of water added and the solution stirred at 65° C. for 1 hour. The cooled solution was acidified with 1.0 M hydrochloric acid causing precipitation of a white solid. The solid was collected by filtration, boiled in hexane and filtered hot. The resulting white solid weighed 8.5 g (90% yield) and had a melting point of 180–182°0 C.

The product gave the following analytical data: NMR (DMSO-d$_6$): δ 4.01 ppm (2H, s, CH$_2$); δ 6.98 ppm (1H, d, J=9 Hz, aryl); δ 7.19 ppm (6H, m, aryl); δ 7.28 ppm (6H, m, aryl); δ 7.36 ppm (1H, d, J=9 Hz, aryl); δ 11.92 ppm (1H, br, COOH).

Anal. C$_{21}$H$_{17}$ClO$_2$. 0.1 H$_2$O (CH calculated: 74.49, 5.12; found: 74.37, 5.27).

6.11 Synthesis of Diethyl-(α,α-diphenyl)-2-fluorobenzyl) malonate

A preferred method of synthesis of diethyl-(α,α-diphenyl)-2-fluorobenzyl)malonate (Compound 55) is as follows: A mixture of 0.1 g (0.0035 mole) of magnesium, 0.64 g (0.004 mole) of diethyl malonate, a catalytic amount of iodine, and 1 drop of carbon tetrachloride in 10 mL anhydrous ethanol was heated at reflux until all the magnesium was consumed (2 hours). Evaporation of the solvent gave a clear oil to which 1 g (0.0034 mole) of chloro-(2-fluorophenyl)-diphenylmethane and 40 mL benzene was added. The mixture was refluxed for 5 minutes and then stirred at ambient temperature for 4 hours. Water (10 mL) and 1 mL of 1.0 M hydrochloric acid was added and the mixture stirred at room temperature for 14 hours. The organic layer was separated, washed with water, dried over sodium sulfate and the solvent removed in vacuo. The resulting red solid was crystallized from ethanol to give a pale yellow solid which weighed 1.0 g (67% yield) and had a melting point of 133.5–135° C.

The product gave the following analytical data: NMR (CDCl$_3$): δ 1.03 ppm (6H, t, J=8 Hz, CH$_3$); δ 3.92 ppm (4H, m, CH$_2$); δ 5.50 ppm (1H, s, CH); δ 6.87 ppm (1H, dd, J=9, 11 Hz, aryl); δ 7.06 ppm (1H, m, aryl); δ 7.26 ppm (8H, m, aryl); δ 7.42 ppm (4H, d, J=9 Hz, aryl).

Anal. C$_{26}$H$_{25}$FO$_4$. 0.25 H$_2$O (CH calculated: 73.48, 6.05; found: 73.44, 5.96).

6.12 Synthesis of 4.4.4-Triphenylbutronitrile

A preferred method of synthesis of 4,4,4-triphenylbutronitrile (Compound 64) is as follows: A mixture of 5.0 g (0.017 mole) of 3,3,3-triphenylpropanol, 2.2 g (0.019 mole) of methanesulfonyl chloride, and 3.6 mL (0.026 mole) of triethylamine in 100 mL of methylene chloride was stirred at −15° C. for 30 minutes. The reaction mixture was then washed sequentially with 50 mL water, 100 mL 1.0 M hydrochloric acid, 100 mL saturated aqueous sodium carbonate, and 100 mL brine. Evaporation of the solvent gave 6.4 g (80% yield) of a white solid (3,3,3-triphenylpropyl mesylate). A mixture of 5.3 g (0.0145 mole) of this mesylate and 0.85 g (0.017 mole) of sodium cyanide was refluxed in 100 mL of methyl sulfoxide for 2.5 hours. To the cooled reaction mixture was added 500 mL of water and 500 mL of ethyl acetate, the layers separated and the aqueous layer extracted three times with 100 mL of ethyl acetate each time. The combined organics were washed with 200 mL of water and dried over magnesium sulfate. The solvent was removed in vacuo and the resultant white solid crystallized from 2-propanol to give 2.3 g (45% yield) of white crystals having a melting point of 130–133° C.

The product gave the following analytical data: NMR (DMSO-d$_6$): δ 2.06 ppm (2H, t, J=8.5 Hz, CH$_2$); δ 3.00 ppm (2H, t, J=8.5 Hz, CH$_2$); δ 7.20–7.36 ppm (15H, m, aryl).

Infrared (KBr) 3018 cm$^{-1}$; 2246 cm$^{-1}$; 1592 cm$^{-1}$; 1489 cm$^{-1}$.

Anal. C$_{22}$H$_{19}$N . 0.1 H$_2$O (CHN calculated: 88.32, 6.46, 4.68; found: 88.24, 6.45, 4.35).

6.13 Synthesis of (2-Chlorophenyl)-diphenylacetamide

A preferred method of synthesis of (2-chlorophenyl)-diphenylacetamide (Compound 75) is as follows: (2-chlorophenyl)-diphenylacetonitrile (Compound 14), 2.0 g (0.007 mole), was dissolved in 15 mL of sulfuric acid and 15 mL of acetic acid and heated for 12 hours at 100° C. The cooled reaction mixture was neutralized with ammonium hydroxide and extracted with methylene chloride. The organic layer was dried over sodium sulfate and the solvent removed in vacuo. The resulting brown solid was crystallized from acetone to give 0.9 g (42% yield) of a light brown solid having a melting point of 197–198.5° C.

The product gave the following analytical data: NMR (CDCl$_3$): δ 5.90 ppm (1H, s, NH$_2$); δ 6.07 ppm (1H, s, NH$_2$); δ 6.93 ppm (1H, d, J=7 Hz, aryl); δ 7.20 ppm (1H, t, J=8 Hz, aryl); δ 7.31 ppm (11H, m, aryl); δ 7.49 ppm (1H, d, J=7 Hz, aryl).

Infrared (KBr) 1690 cm$^{-1}$; 1240 cm$^{-1}$; 1020 cm$^{-1}$.

Anal. $C_{20}H_{16}ClN \cdot 0.3 H_2O$ (CHN calculated: 73.41, 5.11, 4.28; found: 73.13, 5.12, 4.24).

6.14 Synthesis of 3-(2'-Chlorophenyl)-3,3-diphenylpropanal

A preferred method of synthesis of 3-(2'-chlorophenyl)-3,3-diphenylpropanal (Compound 79) is as follows: A mixture of 1.8 g (0.0053 mole) of 3-(2-chlorophenyl)-3,3-diphenylpropionic acid (Compound 36), 0.68 g (0.007 mole) of N-methyl-N-methoxyhydroxylamine hydrochloride, 0.91 g (0.0059 mole) of 1-(3-dimethylaminopropyl)-3-ethylcarbodiimide hydrochloride and 0.97 mL (0.007 mole) of triethylamine in 25 mL of dimethylformamide was stirred at 0–5° C. for 2 hours followed by stirring at room temperature for 15 hours. Water (15 mL) was added and the mixture stirred at room temperature for 1.5 hours before an additional 30 mL of water was added and the mixture extracted with ethyl acetate (3×50 mL) which was then dried over sodium sulfate. Evaporation of the solvent gave an orange oil (0.99 g, 0.0026 mole, 49% yield of N-methyl-N-methoxy-3-(2'-chlorophenyl)-3,3-diphenylpropyl amide). This amide was dissolved in 25 mL of tetrahydrofuran and cooled to 0–5° C. with stirring. A slurry of 0.20 g (0.0053 mole) of lithium aluminum hydride in 5 mL of tetrahydrofuran was added dropwise to this cold, stirring solution. The mixture was stirred at 0–5° C. for 1 hour and quenched with a solution of 9.9 g (0.073 mole) of potassium hydrogen sulfate in 70 mL of water. Ethyl acetate (50 mL) was added and the layers separated. The aqueous layer was extracted with 30 mL of ethyl acetate and the combined organic fractions were dried over sodium sulfate. The solvent was removed in vacuo and the yellow residue crystallized from ethyl acetate to give 0.29 g (91% yield) of a white crystalline product having a melting point of 92–93° C.

The product gave the following analytical data: NMR (CDCl$_3$): δ 3.99 ppm (2H, d, J=3 Hz, CH$_2$); δ 6.94 ppm (1H, d, J=9 Hz, aryl); δ 7.10 ppm (4H, d, J=8 Hz, aryl); δ 7.18 ppm (1H, d, J=9 Hz, aryl); δ 7.29 ppm (8H, m, aryl); δ 7.40 ppm (1H, d, J=8 Hz, aryl); δ 9.48 ppm (1H, t, J=3 Hz, CHO).

Anal. $C_{21}H_{17}ClO$ (CH calculated: 78.62, 5.34; found: 78.46, 5.53).

6.15 Synthesis of 4-(2-Chlorophenyl)-4,4-diphenyl-2-butanone

A preferred method of synthesis of 4-(2-chlorophenyl)-4,4-diphenyl-2-butanone (Compound 82) is as follows: A solution of 1.05 g (0.0027 mole) of N-methyl-N-methoxy 3-(2-chlorophenyl) 3,3-diphenylpropionamide, in 20 mL of tetrahydrofuran was cooled to 0° C. and 1.01 mL of methyl magnesium bromide (3.0 M solution in tetrahydrofuran, 0.00303 mole) was added to the cooled solution. The mixture was stirred at room temperature overnight. The reaction was quenched with cold aqueous hydrochloric acid solution (25 mL, 1.0 M) and then extracted with dichloromethane (2×20 mL). The organic solution was washed with 20 mL of saturated aqueous sodium bicarbonate and 15 mL of brine. The organic layer was dried over sodium sulfate. Evaporation gave 0.89 g of the crude product as a yellow solid. Purification of the crude product by flash column chromatography (silica gel, 1:5 ethyl acetate:hexane) gave 0.385 g (41% yield) of a white solid having a melting point of 120–123° C.

The product gave the following analytical data: NMR (CDCl$_3$): δ 2.20 ppm (3H, s, CH$_3$); δ 4.28 ppm (2H, s, CH$_2$); δ 6.85 ppm (1H, m, aryl); δ 7.04–7.32 ppm (13H, m, aryl).

Anal. $C_{22}H_{19}ClO$ (CH calculated: 78.91, 5.72; found: 78.52, 5.65)

6.16 Synthesis of α-(2-Chlorophenyl)-α-(4-hydroxyphenyl) benzyl alcohol

A preferred method of synthesis of α-(2-chlorophenyl)-α-(4-hydroxyphenyl)benzyl alcohol (Compound 84) is as follows: A solution of 0.5 g (0.0015 mole) of α-(2-chlorophenyl)-α-(4-methoxyphenyl)benzyl alcohol, in 10 mL of dichloromethane, was cooled to −15° C. and 4.5 mL of boron tribromide (1.0 M solution in dichloromethane, 0.0045 mole) was added to the cooled solution. The mixture was stirred at room temperature overnight and then refluxed for 8 hours. The reaction mixture was quenched with water and neutralized by adding aqueous sodium bicarbonate. The mixture was extracted with dichloromethane (3×20 mL). The organic layer was dried over magnesium sulfate. Evaporation gave 0.47 g of the crude product as a thick red oil. Purification of the crude product by flash column chromatography (silica gel, 1:5 ethyl acetate:hexane) gave 0.182 g (39% yield) of a yellow solid having a melting point of 56.5–60° C.

The product gave the following analytical data: NMR (CDCl$_3$): δ 5.76 ppm (1H, bs, OH); δ 6.45 ppm (2H, dd, aryl); δ 6.78 ppm (2H, m, aryl); δ 7.12 ppm (4, m, aryl); δ 7.24–762 ppm (5H, m, aryl).

6.17 Synthesis of Cyclohexyl-diphenylmethanol

A preferred method of synthesis of cyclohexyl-diphenylmethanol (Compound 88) is as follows: A solution of 3.0 g (0.0021 mole) of methylcyclohexyl carboxylate in 20 mL of tetrahydrofuran (THF) was added dropwise, with stirring, to 46 mL (0.0046 mole) of phenylmagnesium bromide (1.0 M in THF) at room temperature. The solution was refluxed for 6 hours and then allowed to cool. Water (15 mL) was added causing a white precipitate to form. The mixture was extracted with ethyl acetate (3×25 mL) and the combined organics dried over sodium sulfate. Evaporation of the solvent gave a clear oil which crystallized from ethanol. The white crystals were collected by filtration to give 4.0 g (75% yield) of a product having a melting point of 76–78° C.

The product gave the following analytical data: NMR (CDCl$_3$): δ 1.00–1.40 ppm (5H, m, aliphatic); δ 1.58 ppm (2H, d, J=12 Hz, aliphatic); δ 1.64–1.82 ppm (3H, m, aliphatic); δ 1.58 ppm (1H, s, OH); δ 2.45 ppm (1H, t, J=13 Hz, CH); δ 7.16 ppm (2H, t, J=9 Hz, aryl); δ 7.30 ppm (4H, m, aryl); δ 7.48 ppm (4H, d, J=9 Hz), aryl).

Anal. $C_{19}H_{22}O \cdot 0.75$ ethanol (CH calculated: 82.83, 8.44; found: 82.07, 8.62).

6.18 Synthesis of Cyclohexyl-diphenylacetonitrile

A preferred method of synthesis of cyclohexyl-diphenylacetonitrile (Compound 89) is as follows: A mixture of 0.94 g (0.024 mole) of sodium amide and 3.85 g (0.02 mole) if diphenylacetonitrile in 25 mL of toluene was stirred at reflux for 3 hours. To this refluxing mixture was added 2.6 mL (0.022 mole) of cyclohexyl chloride. The mixture was stirred at reflux an additional 3 hours and then allowed to cool. To the cool solution was added 50 mL of a 1.0 M HCl solution. The layers were separated and the organic layer was washed with brine and then dried over sodium sulfate. The toluene was removed in vacuo to give a yellow solid (4.9 g). This solid was crystallized from ethanol to give 3.6 g of a white crystalline product having a melting point of 117.5–119° C.

The product gave the following analytical data: NMR (CDCl$_3$): δ 1.29 ppm (5H, m, aliphatic); δ 1.73 ppm (5H, m, aliphatic); δ 2.50 ppm (1H, t, J=12 Hz, CH); δ 7.26 ppm (2H, d, J=9 Hz, aryl); δ 7.32 ppm (4H, t, J=9 Hz, aryl); δ 7.50 ppm (4H, d, J=9 Hz, aryl).

Anal. $C_{20}H_{21}N$ (CHN calculated: 87.23, 7.69, 5.09; found: 87.28, 7.68, 5.05).

6.19 Synthesis of Cyclohexyl-diphenylacetamide

A preferred method of synthesis of Cyclohexyl-diphenylacetamide (Compound 90) is as follows: Cyclohexyl-diphenylacetonitrile (Compound 89), 0.155 g (0.0056 mole), was stirred in 1 mL of sulfuric acid and 1 mL of acetic acid and heated for 9 hours at 110° C. The cooled reaction mixture was diluted with an equal volume of water and extracted with methylene chloride. Separation of the product from the unreacted starting material was accomplished by flash chromatography (7:3 hexane:ethyl acetate on silica gel). Evaporation of the fractions in vacuo gave 0.044 g (27% yield) of a white solid.

The product gave the following analytical data: NMR (CDCl$_3$): δ 0.60 ppm (2H, q, J=9 Hz, CH$_2$); δ 0.93 ppm (1H, q, J=9 Hz, CH$_2$); δ 1.42 ppm (2H, q, J=12 Hz, CH$_2$); δ 1.67 ppm (3H, m, CH$_2$); δ 1.83 ppm (2H, d, J=10 Hz, CH$_2$); δ 2.89 ppm (1H, t, J=12 Hz, CH$_2$); δ 5.58 ppm (1H, br s, NH); δ 6.00 ppm (1H, br s, NH); δ 7.23–7.48 ppm (10H, m, aryl).

6.20 Other Compounds

Other compounds of the invention can be synthesized by routine modification of the above-described syntheses, or by other methods that are well known in the art. Compounds 1, 3, 4, 5, 7, 8, 9, 10, 11, 12, 19, 20, 21, 23, 24, 25, 26, 28, 34, 37, 38, 39, 42, 43, 44, 45, 46, 47, 48, 50, 51, 54, 57, 59, 60, 61, 62, 66, 67, 69, 71, 72, 73, 76, 77 and 87 are available from Aldrich Chemical Co.

Compounds 49 and 52 are available from Maybridge Chemical Co.

7. EXAMPLE

In Vitro Activity

This Example demonstrates the ability of several exemplary compounds of formula (I) to inhibit the Gardos channel of erythrocytes and/or mitogen-induced cell proliferation in vitro. The assays are generally applicable for demonstrating the in vitro activity of other compounds of formula (I).

7.1 Experimental Protocol

The percent inhibition of the Gardos channel (10 μM compound) and the IC$_{50}$ were determined as described in Brugnara et al., 1993, *J. Biol. Chem.* 268(12):8760–8768. The percent inhibition of mitogen-induced cell proliferation (10 μM compound) and the IC$_{50}$ were determined or described in Benzaquen et al. (1995, *Nature Medicine* 1:534–540) with NIH 3T3 mouse fibroblast cells (ATCC No. CRL 1658). Clotrimazole is reported for purposes of comparison. Other cell lines, e.g., cancer cells, endothelial cells and fibroblasts, as well as many others, may be used in the cell proliferation assay. Selection of a particular cell line will depend in part on the desired application, and is well within the capabilities of an ordinarily skilled artisan.

7.2 Results

The results of the in vitro assays are provided in TABLE 1, below. All of the compounds tested exhibited significant activity in at least one of the assays. Most of the compounds tested exhibited significant activity in both of the assays.

TABLE 1

Pharmacological Activities of Various Compounds
(Inhibition measured at 10 μM)

| Compound No. | Mitogen-induced cell proliferaiton IC$_{50}$ (μM) | % Inhibition | Gardos Channel IC$_{50}$ (μM) | % Inhibition |
|---|---|---|---|---|
| Clotrimazole | 0.626 | 93.0 | 0.046 | 99.3 |
| (1) | — | — | 0.755 | 97.0 |
| (2) | — | 64.8 | 0.459 | 99.4 |

TABLE 1-continued

Pharmacological Activities of Various Compounds
(Inhibition measured at 10 μM)

| Compound No. | Mitogen-induced cell proliferaiton IC$_{50}$ (μM) | % Inhibition | Gardos Channel IC$_{50}$ (μM) | % Inhibition |
|---|---|---|---|---|
| (3) | — | 53.0 | 1.205 | 86.6 |
| (4) | — | 37.7 | 2.86 | 91.0 |
| (5) | 1.28 | 66.0 | 1.653 | 86.0 |
| (6) | 2.10 | 31.0 | 0.961 | 98.0 |
| (7) | — | 6.6 | 0.410 | 98.2 |
| (8) | — | 28.3 | 2.851 | 95.6 |
| (9) | — | 32.7 | 21.803 | 77.2 |
| (10) | 4.80 | 25.5 | 0.957 | 89.7 |
| (11) | 2.31 | 52.0 | 2.16 | 99.2 |
| (12) | 1.70 | 72.8 | 0.252 | 99.0 |
| (13) | 0.92 | 87.0 | 0.133 | 72.4 |
| (14) | 2.20 | 95.8 | 0.048 | 98.8 |
| (15) | 2.60 | 88.63 | 0.0968 | 100.0 |
| (16) | 0.40–2.0 | 99.4 | 0.087 | 98.0 |
| (17) | 3.90 | 91.8 | 0.860 | 100.0 |
| (18) | 10.0 | 76.09 | 0.431 | 98.0 |
| (19) | 5.8 | 80.0 | 1.129 | 97.0 |
| (20) | — | 39.0 | 0.795 | 98.1 |
| (21) | 2.8 | 99.0 | 0.725 | 97.3 |
| (22) | 6.8 | 85.0 | 0.302 | 82.0 |
| (23) | 3.8 | 77.0 | 0.216 | 97.9 |
| (24) | — | 29.0 | 0.135 | 97.9 |
| (25) | — | 70.0 | — | 34.4 |
| (26) | 1.30 | 99.0 | — | 10.0 |
| (27) | 3.00 | 99.0 | 0.449 | 100.0 |
| (28) | 0.70 | 99.0 | 5.22 | 98.0 |
| (29) | 3.10 | 99.0 | 0.649 | 100.0 |
| (30) | 0.90 | 99.0 | 0.272 | 97.0 |
| (31) | 2.60 | 89.0 | 0.445 | 99.0 |
| (32) | — | 54.0 | 0.068 | 95.7 |
| (33) | — | 45.0 | 0.125 | 100.0 |
| (34) | — | 68.0 | 0.939 | 96.3 |
| (35) | — | 38.0 | 0.430 | 95.8 |
| (36) | 0.60 | 92.0 | 3.11 | 78.6 |
| (37) | — | 31.0 | 0.057 | 100.0 |
| (38) | 0.80–2.30 | 99.0 | 0.22 | 92.0 |
| (39) | 3.30 | 99.0 | 1.682 | 97.0 |
| (40) | 1.0–1.20 | 99.0 | — | (16.9) |
| (41) | 1.40 | 99.0 | 2.071 | 97.0 |
| (42) | 3.30 | 99.0 | 0.615 | 99.0 |
| (43) | 0.80 | 99.0 | 0.061 | 99.0 |
| (44) | — | 82.0 | 0.388 | 79.4 |
| (45) | 0.80 | 99.0 | 0.320 | 98.0 |
| (46) | 2.20 | 99.0 | 0.076 | 99.5 |
| (47) | 0.80 | 99.0 | 0.193 | 100.0 |
| (48) | 0.40 | 98.0 | 1.29 | 100.0 |
| (49) | 0.30 | 94.0 | 0.336 | 88.0 |
| (50) | 0.50 | 99.0 | 0.288 | 100.0 |
| (51) | — | 37.0 | 0.551 | 100.0 |
| (52) | 1.70 | 93.0 | 0.255 | 94.0 |
| (53) | — | 74.0 | 0.101 | 98.0 |
| (54) | 0.20 | 99.0 | — | 17.4 |
| (55) | — | 5.0 | 0.058 | 98.0 |
| (56) | 3.20 | 99.0 | 0.275 | 91.0 |
| (57) | — | 21.0 | 1.506 | 89.0 |
| (58) | — | 99.0 | 0.247 | 99.6 |
| (59) | 3.00 | 98.0 | 0.489 | 100.0 |
| (60) | — | 31.0 | 0.304 | 98.0 |
| (61) | 1.6 | 99.0 | 2.372 | 85.0 |
| (62) | — | 31.0 | 0.098 | 98.0 |
| (63) | — | 37.0 | 1.017 | 69.0 |
| (64) | 5.80 | 63.0 | 0.088 | 100.0 |
| (65) | 1.60 | 99.0 | 0.435 | 98.0 |
| (66) | — | 73.0 | 0.384 | 67.2 |
| (67) | 1.40 | 98.0 | 0.43 | 96.1 |
| (68) | 3.1 | 98.0 | 0.236 | 97.5 |
| (69) | — | 99.0 | 0.025 | 100.0 |
| (70) | 1.20 | 92.0 | 0.459 | 99.6 |

TABLE 1-continued

Pharmacological Activities of Various Compounds
(Inhibition measured at 10 μM)

| Compound No. | Mitogen-induced cell proliferaiton | | Gardos Channel | |
|---|---|---|---|---|
| | IC$_{50}$ (μM) | % Inhibition | IC$_{50}$ (μM) | % Inhibition |
| (71) | 1.10 | 97.0 | — | 0.4 |
| (72) | 2.40 | 99.0 | 1.075 | 72.6 |
| (73) | 2.50 | 99.0 | 0.371 | 98.9 |
| (74) | — | 70.0 | 1.405 | 97.5 |
| (75) | — | 90.0 | 0.006 | 98.0 |
| (76) | — | 84.0 | — | (30.4) |
| (77) | — | 83.0 | — | 16.4 |
| (78) | — | 72.0 | 0.22 | 95.0 |
| (79) | 2.70 | 99.0 | 0.083 | 96.0 |
| (80) | — | 62.0 | 0.206 | 97.0 |
| (81) | — | 53.0 | 0.187 | 100.0 |
| (82) | 5.0 | 98.0 | 0.027 | 99.5 |
| (83) | 6.4 | 80.0 | 0.918 | 96.7 |
| (84) | 1.0 | 99.0 | 1.274 | 95.3 |
| (85) | 7.0 | 91.0 | 0.739 | 98.0 |
| (86) | 2.4 | 99.0 | 0.237–0.455 | 93.9 |
| (87) | 2.2 | 96.0 | 0.068 | 99.0 |
| (88) | 9.5 | 94.0 | 0.862 | 99.0 |
| (89) | 0.90 | 98.0 | 6.128 | 70.2 |
| (90) | 3.0 | 86.0 | 0.072 | 98.3 |

8. EXAMPLE

Clotrimazole Metabolite B (Compound 6) Displaces Bound $^{125}$I-ChTX

Charybdotoxin (ChTX), a peptide of 37 amino acids in length, is a potent inhibitor of many Ca$^{2+}$-activated and voltage-gated K$^+$ channels, including the Gardos channel (Miller et al., 1985, *Nature* 313:316–318; Bontems et al., 1992, *Biochemistry* 31:7756–7764; Park et al., 1991, *Proc. Natl. Acad. Sci. U.S.A.* 88:2046–2050; Vazquez et al., 1989, *J. Biol. Chem.* 264:20902–20909; Grinstein and Smith, 1990, *J. Gen. Physiol.* 95:97–120; Brugnara et al., 1993, *J. Biol. Chem.* 268:8760–8768). Because bound ChTX inhibitor may be competitively displaced by other Gardos channel inhibitors, ChTX is an important tool for understanding Gardos channel function and activation. This example demonstrates displacement of ChTX by CLT metabolite B (Compound 6). The method described herein is generally applicable for demonstrating the ability of other compounds of formula (I) to competitively displace ChTX.

8.1 $^{125}$ChTX binding to red cells

White cells were removed by passing 0.8 mL of packed red cells through a 5 mL syringe containing a mixture of equal parts of alpha-cellulose and microcrystalline cellulose as originally described by Beutler and West, 1976, *J. Lab. Clin. Med.* 88:328–333. Red cells were washed three times in binding medium containing 18 mM NaCl, 2 mM KCl, 10 mM tris-Cl, pH 8.0, 230 mM sucrose and 0.25% bovine serum albumin. A suspension was then made in the same medium at 15% Hematocrit (HCt). Cells were added to 3.5 ml of binding medium containing $^{125}$IChTX to a final concentration of 1×10$^7$ cells/mL, in the absence or presence of the specified drugs. Tubes containing cell suspension were gently rotated for 90 min. at room temperature. At the end of the incubation, aliquots of 1 ml were pelleted by microfuge and washed 3 times at 4° C. with a solution containing 200 mM NaCl, 10 mM tris-Cl, pH 8.0. The washed red cell pellet was then lysed in 1 ml of 0.01% Acationox (American Scientific Products), and counted in a gamma counter. Aliquots of binding medium were counted prior to addition of cells at the end of the binding assay.

8.2 Displacement by Metabolite B (Compound 6)

Metabolite B (Compound 6) was added to the red cells from a stock solution in acetonitrile. A similar amount of acetonitrile was added to each control tube. Specific binding was estimated on the basis of displacement of $^{125}$I-ChTX by 50 nM unlabeled ChTX. Various concentrations of metabolite B (Compound 6) or unlabeled ChTX were added to the cell suspension (1×10$^7$ cells/mL) prior to the addition of $^{125}$I-ChTX.

8.3 Results

The results of the assay are depicted in TABLE 2. Metabolite B (Compound 6) specifically displaces $^{125}$IChTX binding.

TABLE 2

Displacement of $^{125}$I-ChTX Binding by Metabolite B (Compound 6)

| | $^{125}$I-ChTX | | Displacement | |
|---|---|---|---|---|
| | Binding | σ | (%) | σ (%) |
| control | 1.279 | 0.030 | 0.0 | 2.3 |
| 50 nM ChTX | 0.608 | 0.002 | 100.0 | 0.3 |
| 10 μM CLT | 1.000 | 0.06 | 41.6 | 6.0 |
| 1 nM B | 1.403 | 0.13 | (18.5) | 9.3 |
| 10 nM B | 1.399 | 0.15 | (17.9) | 10.7 |
| 100 nM B | 1.239 | 0.35 | 6.0 | 28.1 |
| 500 nM B | 1.134 | 0.07 | 21.6 | 6.1 |
| 1 μM B | 1.327 | 0.05 | (7.2) | 4.1 |
| 5 μM B | 1.016 | 0.07 | 39.2 | 7.0 |
| 10 μM B | 0.790 | 0.04 | 72.9 | 5.1 |

σ is standard deviation
B is CLT Metabolite B (Compound 6)

9. EXAMPLE

Clotrimazole and Its Metabolites Inhibit Ca$^{2+}$-Activated Potassium Transport In Vivo in Humans This Example demonstrates the ability of Clotrimazole (CLT) and CLT metabolites A and B (Compounds 17 and 6, respectively) to inhibit the Gardos channel of erythrocytes in vivo in humans. The methods described herein are generally applicable for demonstrating the in vivo activity of other compounds of formula (I) when administered to humans.

9.1 Experimental Protocol

Two subjects, one male (A, 72 Kg) and one female (D, 56 Kg), ingested one 500 mg CLT tablet every twelve hours for six days, corresponding to a daily CLT dose of 14 and 18 mg/kg, respectively. Blood was collected six hours after the AM dose of CLT on days 3 and 6 for measurement of inhibition of red cell calcium-activated potassium transport.

9.2 Results

TABLE 3 depicts the results of the measurement of the red cell calcium-activated potassium transport in the two normal subjects. As shown in TABLE 3, there was significant inhibition of calcium-activated potassium transport during CLT administration, which persisted for at least 7 days after the drugs were discontinued. At day 6, plasma CLT concentration was 0.2 μM with combined metabolite levels of 2.9 μM (subject A) and 3.85 μM (subject D). There was no evidence of CLT or CLT-metabolites in plasma two days after CLT administration was stopped.

TABLE 3

Effect of 6-Day Course of Oral Clotrimazole Blood Levels and Red Cells Ca$^{2+}$-Activated K$^+$ Transport in Two Subjects

|  | CLT Levels | | | Blood Cells | | Ca$^{2+}$-activated |
|---|---|---|---|---|---|---|
|  | | Plasma | | CLT | | $^{86}$Rb influx |
|  | CLT µM | Met-B µM | Met-A µM | µmol/L cells | Met A + B µM | inhibition % |
| Subject A | | | | | | |
| Baseline | 0 | 0 | 0 | 0 | 0 | 0 ± 4 |
| CLT day 3 | 0.2 | 1.1 | 0.7 | 0.45 | 0.45 | 74 ± 5 |
| CLT day 6 | 0.2 | 1.1 | 1.8 | 0.8 | 4.15 | 73 ± 4 |
| Wash-out day 6 | 0 | <0.1 | <0.1 | 0.4 | 0 | 71 ± 7 |
| Wash-out day 10 | 0 | <0.1 | <0.1 | ND | 0 | 75 ± 11 |
| Wash-out day 13 | 0 | 0 | 0 | 0.85 | 0 | 58 ± 9 |
| Wash-out day 20 | 0 | 0 | 0 | 0 | 0 | 0 ± 10 |
| Subject B | | | | | | |
| Baseline | 0 | 0 | 0 | 0 | 0 | 0 ± 10 |
| CLT day 3 | 0.25 | 0.8 | 1.65 | 0.2 | 4.2 | 80 ± 28 |
| CLT day 6 | 0.2 | 1.35 | 2.5 | 1.1 | 7.3 | 83 ± 7 |
| Wash-out day 8 | 0 | <0.1 | <0.1 | 0.6 | 0 | 79 ± 21 |
| Wash-out day 10 | 0 | <0.1 | <0.1 | 0.65 | 0 | 82 ± 4 |
| Wash-out day 13 | 0 | 0 | 0 | 0.7 | 0 | 37 ± 30 |
| Wash-out day 20 | 0 | 0 | 0 | 0.25 | 0 | 0 ± 13 |

Measurements of whole blood CLT levels allowed estimation of "blood cell-associated" CLT levels. As shown in TABLE 3, significant levels of "blood cell-associated CLT were detected up to 7 days (subject A) and 14 days (subject D) following CLT withdrawal. There were no metabolites detectable in blood cells 2 days after CLT was discontinued. These data suggest that red cells and possibly other blood elements bind or contain a significant amount of CLT for an extended period of time, even in the absence of measurable plasma levels. CLT metabolites show a different behavior, disappearing at the same time from both plasma and cells.

There was a significant correlation between summed levels of CLT and its metabolites in cells and the percent inhibition of the Gardos channel measured in whole blood [% inhibition=31.7 log (CLT+Met A+Met B, µM)+56.4; r$^2$=0.439, t=3.06, p<0.02, n=14].

Metabolite B (Compound 6) specifically inhibits potassium transport via the red cell Gardos channel. CLT and metabolite B (Compound 6) were incubated with a red cell suspension at 20% Hct. Comparison of the inhibitory effect on the red cell Gardos channel of CLT and metabolite B (Compound 6) shows IC$_{50}$ values of 310±63 nM for CLT and 720±190 nM for metabolite B (Compound 6). The value for the inhibition of K$^+$ transport by metabolite B (Compound 6) is two to three fold lower than the IC$_{50}$ for displacement of $^{125}$I-ChTx by metabolite B (Compound 6). It has previously been shown, (Brugnara, 1993, supra) for ChTX that there is a two to three fold increase in the IC$_{50}$ value for displacement of $^{125}$I-ChTX by ChTX compared with the inhibition of K$^+$ transport by ChTX.

Inhibition of K$^+$ transport was measured by varying concentrations of metabolite B (Compound 6) and CLT, and the results are depicted in TABLE 4. The percent inhibition of K$^+$ transport was greater than 50% when the cells were treated with 500 nM CLT or 1 µM metabolite B (Compound 6) and reached maximal levels at 5 µM CLT and 10 µM metabolite B (Compound 6).

Oral administration of CLT was not associated with significant side effects in any of the subject studied. In particular no nausea, vomiting or diarrhea were observed. No changes were observed in liver function tests, plasma creatine or blood urea nitrogen (BUN).

TABLE 4

| [drug] | flux | % control | % inhibition |
|---|---|---|---|
| Control | 1.152 | 100.0% | 0.0% |
| CLT: | | | |
| 1 nM | 1.155 | 100.3% | −0.3% |
| 10 nM | 1.124 | 97.6% | 2.4% |
| 100 nM | 0.892 | 77.4% | 22.6% |
| 500 nM | 0.518 | 45.0% | 55.0% |
| 1 µM | 0.248 | 21.5% | 78.5% |
| 5 µM | 0.038 | 3.3% | 96.7% |
| 10 µM | 0.043 | 3.7% | 96.3% |
| 2-chlorophenyl-bis-phenyl-methanol (Compound 6): | | | |
| 1 nM | 1.444 | 125.3% | −25.3% |
| 10 nM | 1.115 | 96.8% | 3.2% |
| 100 nM | 0.952 | 82.6% | 17.4% |
| 500 nM | 0.717 | 62.2% | 37.8% |
| 1 µM | 0.437 | 37.9% | 62.1% |
| 5 µM | 0.25 | 21.7% | 78.3% |
| 10 µM | 0.113 | 9.8% | 90.2% |

10. EXAMPLE
Metabolite B (Compound 6) Inhibits Mitogen-Induced Cell Proliferation In Vitro in Various Cell Lines This Example demonstrates the ability of Clotrimazole (CLT) metabolite B (Compound 6) to inhibit mitogen-induced cell proliferation in various cell lines, including cancer cells. Such assays are generally applicable for demonstrating the activities of other compounds of formula (I) in various cell lines.

10.1 Experimental Protocol

Human melanoma cells (MM-RU) and colon adenocarcinoma cells (HT29) were cultured in the presence and absence of 10 $\mu$M CLT metabolite B (Compound 6) as described in Benzaquen et al., 1995, *Nature Medicine* 1:534–540 and the level of DNA synthesis determined by measuring [$^3$H]thymidine uptake.

10.2 Results

CLT metabolite B (Compound 6) was a potent inhibitor of proliferation of these cell lines in vitro. Specifically, CLT metabolite B (Compound 6) inhibited [$^3$H]thymidine uptake by about 60% versus controls in MM-RU cells and by about 50% versus controls in HT29 cells.

11. EXAMPLE
CLT Inhibits Cell Proliferation In Vivo

This Example demonstrates the ability of Clotrimazole (CLT) to inhibit cell proliferation in an in vivo animal model of human melanoma. Such an animal model is contemplated to be applicable for demonstrating the in vivo activity of compounds of formula (I) which inhibit MM-RU cells in vitro.

11.1 Experimental Protocol

Mice with severe combined immunodeficiency disease (SCID) were inoculated via the lateral tail vein with approximately 2.5×10$^6$ MM-RU human melanoma cells, a cell line that produces metastases only in the lungs (Byers et al., 1993, *Melanoma Res.* 3:247–253). Starting on the day of inoculation, subcutaneous injections of either vehicle (control group, n=9) or CLT (120 mg/Kg; treatment group, n=10) was administered daily for a period of 10 weeks. At the end of the 10 week treatment period, the mice were sacrificed and examined for metastases.

11.2 Results

Ten weeks after inoculation of MM-RU cells, all animals in the control group had developed pleural macroscopic and microscopic lung metastases. In stark contrast, half of the CLT-treated animals were free of macroscopic metastases, and two did not even exhibit evidence of microscopic metastases.

Despite the variability in the number of metastases observed within each group, animals in the CLT-treated group exhibited significantly fewer pleural (14±4 in control vs. 2±1 in treated animals; P<0.05) and microscopic (27±9 in control vs. 7±2 in treated animals; P<0.05) metastases than those in the control group. A greater number of metastases were counted in the microscopic sections than on the pleural surface, as is typical of the SCID-mice/MM-RU-cells model. There was an excellent correlation between both methods of counting (r=0.90). Consistent with the high organ specificity for lung tissue of the MM-RU melanoma cells, other organs did not show any histological evidence of metastatic lesions.

Animals in the control and treatment groups did not show any evidence of systemic metastatic disease or toxicity; both control and CLT-treated animals gained weight in comparable amounts.

In vivo efficacy in this mouse melanoma model can be demonstrated with other compounds of formula (I) which inhibit MM-RU cells in vitro as well.

12. EXAMPLE
Formulations

The following examples provide exemplary, not limiting, formulations for administering the compounds of the invention to mammalian, especially human, patients. Any of the compounds described herein, or pharmaceutical salts or hydrates thereof, may be formulated as provided in the following examples.

12.1 Tablet Formulation

Tablets each containing 60 mg of active ingredient are made up as follows:

| | |
|---|---|
| Active Compound | 60 mg |
| Starch | 45 mg |
| Microcrystalline Cellulose | 45 mg |
| Sodium carboxymethyl starch | 4.5 mg |
| Talc | 1 mg |
| Polyvinylpyrrolidone (10% in water) | 4 mg |
| Magnesium Stearate | 0.5 mg |
| | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules are dried at 50°–60° C. and passed through a No. 18 mesh U.S. sieve. The sodium carboxymethyl starch, magnesium stearate and talc, previously passed through a No. 60 mesh U.S. sieve, are then added to the granules, which, after mixing are compressed by a tablet machine to yield tablets each weighing 150 mg.

Tablets can be prepared from the ingredients listed by wet granulation followed by compression.

12.2 Gelatin Capsules

Hard gelatin capsules are prepared using the following ingredients:

| | |
|---|---|
| Active Compound | 250 mg/capsule |
| Starch dried | 200 mg/capsule |
| Magnesium Stearate | 10 mg/capsule |

The above ingredients are mixed and filled into hard gelatin capsules in 460 mg quantities.

12.3 Aerosol Solution

An aerosol solution is prepared containing the following components:

| | |
|---|---|
| Active Compound | 0.25% (w/w) |
| Ethanol | 29.75% (w/w) |
| Propellant 22 (Chlorodifluoromethane) | 77.00% (w/w) |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

12.4 Suppositories

Suppositories each containing 225 mg of active ingredient are made as follows:

| | |
|---|---|
| Active Compound | 225 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

12.5 Suspensions

Suspensions each containing 50 mg of medicament per 5 mL dose are made as follows:

| | |
|---|---|
| Active Compound | 50 mg |
| Sodium carboxymethylcellulose | 50 mg |
| Syrup | 1.25 mL |
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor and some color are diluted with some of the water and added, with stirring. Sufficient water is then added to produce the required volume.

The foregoing written specification is considered to be sufficient to enable one skilled in the art to practice the invention. Various modifications of the above-described modes for carrying out the invention which are obvious to those skilled in the pharmaceutical arts or related fields are intended to be within the scope of the following claims.

All cited references are hereby incorporated in their entireties by reference herein.

What is claimed is:

1. A compound selected from the group consisting of: a compound having the formula:

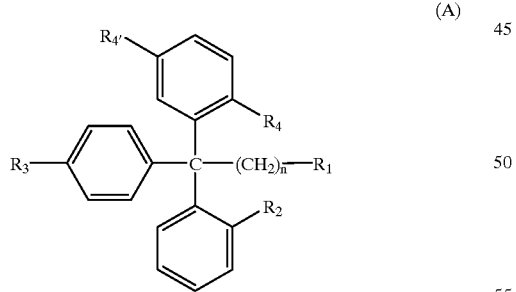

(A)

or a pharmaceutically acceptable salt or hydrate thereof, wherein:

n is 0, 1, 2, 3 or 4;

$R_1$ is —H, —OR, —SR, —CN, —C(O)R, —C(S)R, —C(O)OR, —C(S)OR, —C(O)SR, —C(S)SR, —C(O)NR$_2$, —C(S)NR$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$;

$R_2$ is —F, —Cl, —Br or —I;

$R_3$ is —R, —OR or —SR;

$R_4$ is —H or —NR$_2$;

$R_5$ is —H, —F, —Cl, —Br or —I; and each R is independently selected from the group consisting of —H, ($C_1$–$C_6$) alkyl, ($C_1$–$C_6$) alkenyl, ($C_1$–$C_6$) alkynyl and ($C_1$–$C_6$) alkoxy, with the provisos that (i) when n is 0 and $R_1$ is —H or —OH, $R_3$ is other than —H; and (ii) when n is 0 and $R_1$ is —H, $R_3$ is other than —OH;

a compound having the formula:

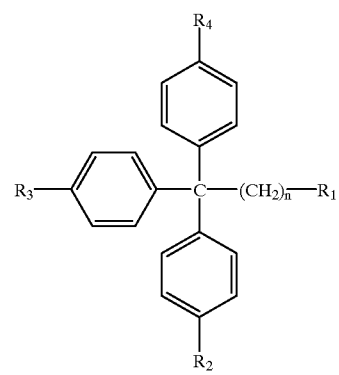

(B)

or a pharmaceutically acceptable salt or hydrate thereof, wherein:

n is 0, 1, 2, 3 or 4;

$R_1$ is —NR$_2$, —C(O)R, —C(S)R, —C(O)NR'$_2$ or —C(S)NR'$_2$;

$R_2$ is —F, —Cl, —Br or —I;

$R_3$ is —F, —Cl, —Br or —I;

$R_4$ is —F, —Cl, —Br or —I;

each R is independently selected from the group consisting of —H, ($C_1$–$C_6$) alkyl, ($C_1$–$C_6$) alkenyl, ($C_1$–$C_6$) alkynyl and ($C_1$–$C_6$) alkoxy; and each R' is independently selected from the group consisting of —H, ($C_1$–$C_6$) alkyl, ($C_1$–$C_6$) alkenyl, ($C_1$–$C_6$) alkynyl and ($C_1$–$C_6$) alkoxy; and a compound having the formula:

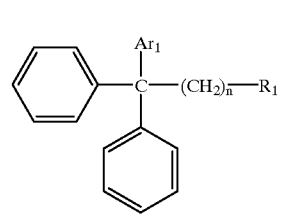

(C)

or a pharmaceutically acceptable salt or hydrate thereof wherein:

n is 0, 1, 2, 3, or 4;

Ar$_1$ is phenyl or cyclohexyl;

$R_1$ is —NR$_2$, —CH[C(O)OR]$_2$, —CH[C(S)OR]$_2$, —CH[C(O)SR]$_2$, —CH[C(S)SR]$_2$, —C(O)NR$_2$ or —C(S)NR$_2$; and each R is independently selected from the group consisting of —H, ($C_1$$C_6$) alkyl, ($C_1$–$C_6$) alkenyl, ($C_1$–$C_6$) alkynyl and ($C_1$–$C_6$) alkoxy, with the proviso that when $R_1$ is —NH$_2$ or —C(O)NH$_2$, is 1, 2 or 3.

2. A compound according to claim 1, wherein said compound has the formula:

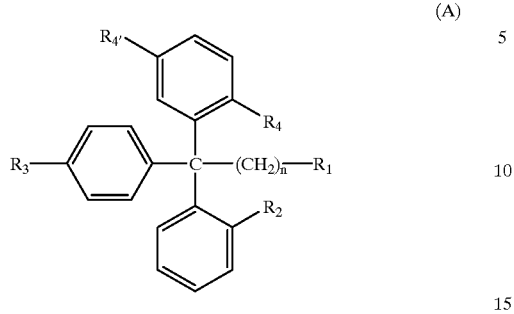

(A)

or a pharmaceutically acceptable salt or hydrate thereof, wherein:

n is 0, 1, 2, 3 or 4;

$R_1$ is —H, —OR, —SR, —CN, —C(O)R, —C(S)R, —C(O)OR, —C(S)OR, —C(O)SR, —C(S)SR, —C(O)NR_2, —C(S)NR_2, —CH[C(O)R]_2, —CH[C(S)R]_2, —CH[C(O)OR]_2, —CH[C(S)OR]_2, —CH[C(O)SR]_2, —CH[C9S)SR]_2;

$R_2$ is —F, —Cl, —Br or —I;

$R_3$ is —R, —OR or —SR;

$R_4$ is —H or —NR_2;

$R_{4'}$ is —H, —F, —Cl, —Br or —I; and each R is independently selected from the group consisting of —H, ($C_1$–$C_6$) alkyl, ($C_1$–$C_6$) alkenyl, ($C_1$–$C_6$) alkynyl and ($C_1$–$C_6$) alkoxy, with the provisos that (i) when n is 0 and $R_1$ is —H or —OH, $R_3$ is other than —H; and (ii) when n is 0 and $R_1$ is —H, $R_3$ is other than —OH.

3. The compound according to claim 2, wherein said compound is selected from the group consisting of compounds

14

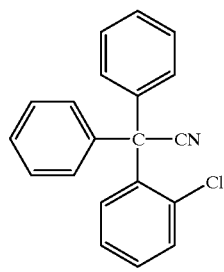

15

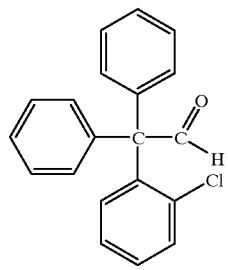

32

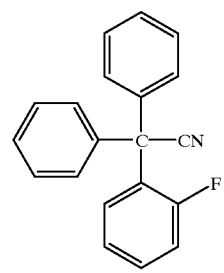

33

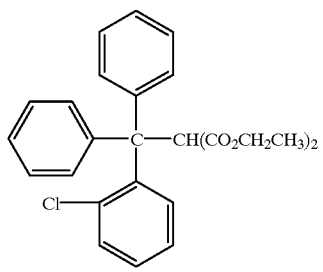

36

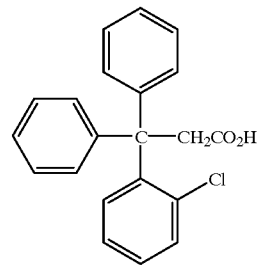

55

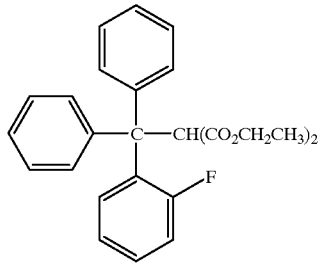

70

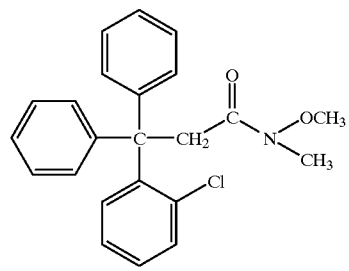

75 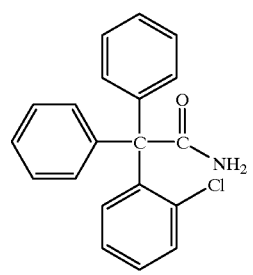
79 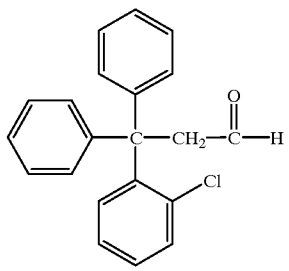
80 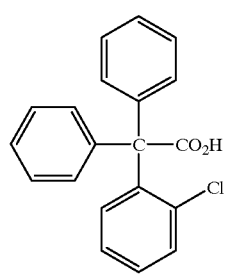
81 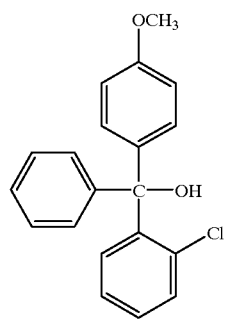
82 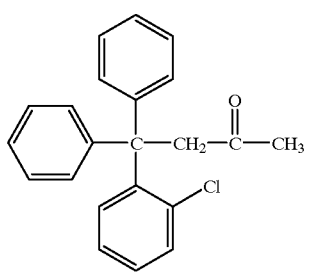
83 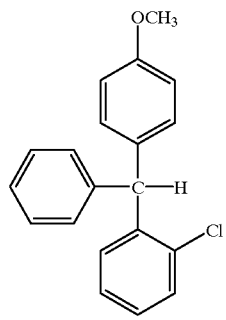
84 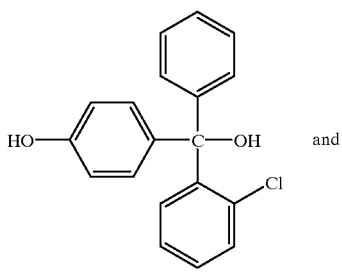 and
86 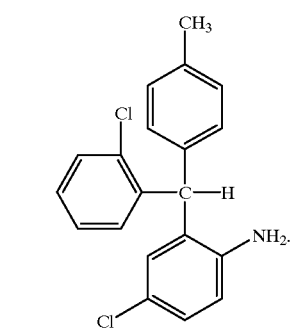
4. The compound according to claim 1, wherein said compound has the formula:
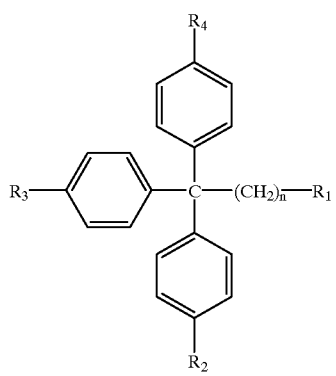
(B)
or a pharmaceutically acceptable salt or hydrate thereof, wherein:
n is 0, 1, 2, 3 or 4;

$R_1$ is —$NR_2$, —C(O)R, —C(S)R, C(O)$NR'_2$ or —C(S)$NR'_2$;

$R_2$ is —F, —Cl, —Br or —I;

$R_3$ is —F, —Cl, —Br or —I;

$R_4$ is —F, —Cl, —Br or —I;

each R is independently selected from the group consisting of —H, ($C_1$–$C_6$) alkyl, ($C_1$–$C_6$) alkenyl, ($C_1$–$C_6$) alkynyl and ($C_1$–$C_6$) alkoxy; and each R' is independently selected from the group consisting of —H, ($C_1$–$C_6$) alkyl, ($C_1$–$C_6$) alkenyl, ($C_1$–$C_6$) alkynyl and ($C_1$–$C_6$) alkoxy.

5. The compound according to claim 4, wherein said compound is selected from the group consisting of compounds

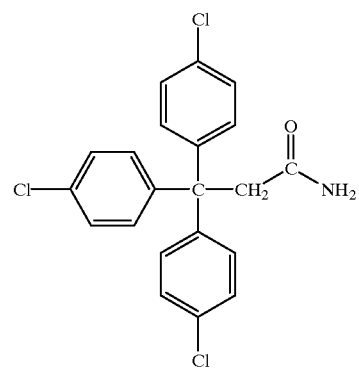

30

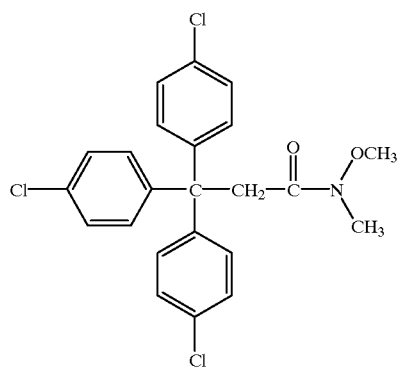

40

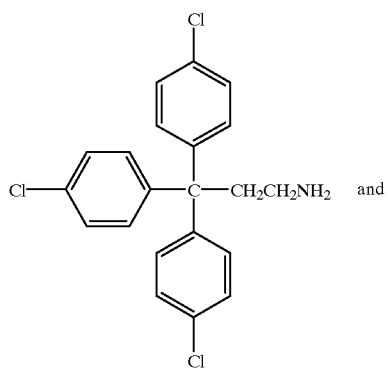

41

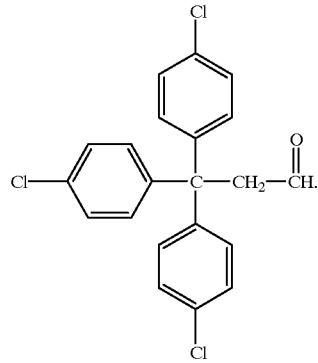

65

6. The compound according to claim 1, wherein said compound has the formula:

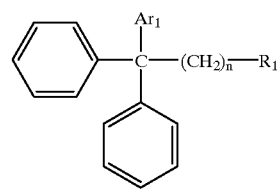

(C)

or a pharmaceutically acceptable salt or hydrate thereof, wherein:

n is 0, 1, 2, 3 or 4;

$Ar_1$ is phenyl or cyclohexyl;

$R_1$ is —$NR_2$, —CH[C(O)OR]$_2$, —CH[C(S)OR]$_2$, —CH[C(O)SR]$_2$, —CH[C(S)SR]$_2$, —C(O)$NR_2$ or —C(S)$NR_2$; and each R is independently selected from the group consisting of —H, ($C_1$–$C_6$) alkyl, ($C_1$–$C_6$) alkenyl, ($C_1$–$C_6$) alkynyl and ($C_1$–$C_6$) alkoxy, with the proviso that when $R_1$ is —$NH_2$ or —C(O)$NH_2$, n is 1, 2 or 3.

7. The compound according to claim 1, wherein said compound is selected from the group consisting of compounds

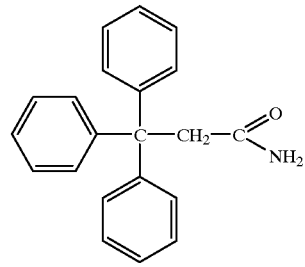

18

-continued

29
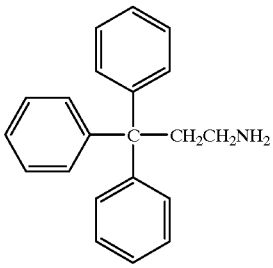

31
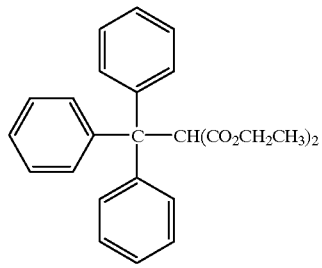

56
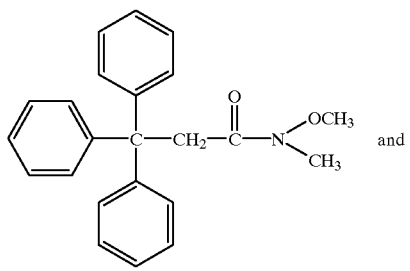

78
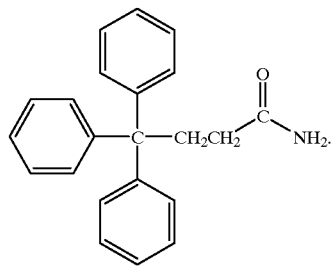

8. A pharmaceutical composition comprising a compound in admixture a pharmaceutically acceptable excipient, carrier or diluent, said compound having the formula:

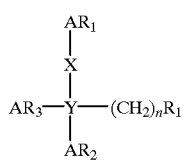
(I)

or a pharmaceutically acceptable salt or hydrate thereof, wherein:

n is 0, 1, 2, 3 or 4;

X is absent, $(C_1-C_3)$ alkyl, $(C_1-C_3)$ alkenyl, or $(C_1-C_3)$ alkynyl;

Y is C, N, P, Si or Ge;

$R_1$ is absent, -halo, —R, —OR, —SR, —NR$_2$, —ONR$_2$, —NO$_2$, —CN, —C(O)R, —C(S)R, —C(O)OR, —C(S)OR, —C(O)SR, —C(S)SR, —C(O)NR$_2$, —C(S)NR$_2$, —C(O)NR(OR), —C(S)NR(OR), C(O)NR(SR), C(S)NR(SR), —CH(CN)$_2$, —CH[C(O)R]$_2$, —CH[C(S)R]$_2$, —CH[C(O)OR]$_2$, CH[C(S)OR]$_2$, —CH[C(O)SR]$_2$, —CH[C(S)SR]$_2$ or aryl;

Ar$_1$ is aryl, substituted aryl, heteroaryl other than imidazole, nitroimidazole and triazole, heteroarylium other than imidazolium, nitroimidazolium and triazolium, $(C_5-C_8)$ cycloalkyl or $(C_5-C_8)$ heterocycloalkyl;

Ar$_2$ is aryl or substituted aryl;

Ar$_3$ is aryl, substituted aryl, biaryl or heteroaryl other than imidazole, nitroimidazole and triazole;

each R is independently selected from the group consisting of —H, $(C_1-C_6)$ alkyl, substituted $(C_1-C_6)$ alkyl, $(C_1-C_6)$ alkenyl, substituted $(C_1-C_6)$ alkenyl, $(C_1-C_6)$ alkynyl, substituted $(C_1-C_6)$ alkynyl and $(C_1-C_6)$ alkoxy;

the aryl substituents are each independently selected from the group consisting of -halo, trihalomethyl, —R, —R', —OR', —SR', NR'$_2$, —NO$_2$, —CN, —C(O)R', —C(S)R', —C(O)OR', —C(S)OR', —C(O)SR' and —C(S)SR';

the alkyl, alkenyl and alkynyl substituents are each independently selected from the group consisting of -halo, —R', —OR', —SR', NR'$_2$, —NO$_2$, —CN—C(O)R', —C(S)R', —C(O)OR', —C(S)OR', —C(O)SR', —C(S)SR', aryl, γ-butyrolactonyl, pyrrolidinyl and succinic anhydridyl; and each R' is independently selected from the group consisting of —H, $(C_1-C_6)$ alkyl, $(C_1-C_6)$ alkenyl and $(C_1-C_6)$ alkynyl.

9. The pharmaceutical composition of claim 8, wherein the substituents are as follows:

n is 0, 1, 2, 3 or 4;

X is absent or —C≡C—;

Y is C, N, P, Si or Ge;

$R_1$ is absent, —F, —Cl, —Br, —R, —OR, —SR, —NR$_2$, —ONR$_2$, —NO$_2$, —CN, —C(O)R, —C(O)OR, —C(O)NR$_2$, —C(O)NR(OR), —CH[C(O)OR]$_2$ or cyclo-penta-2,4-dien-1-ylidene, Ar$_1$ is phenyl, substituted phenyl, heteroaryl other than imidazole, nitroimidazole and triazole, cyclohexyl, piperidyl or pyridinium;

Ar$_2$ is phenyl or substituted phenyl;

Ar$_3$ is phenyl, substituted phenyl, biphenyl, naphthyl or pyridyl;

R is —H, $(C_1-C_3)$ alkyl, substituted $(C_1-C_3)$ alkyl, $(C_1-C_3)$ alkenyl, substituted $(C_1-C_3)$ alkenyl $(C_1-C_3)$ alkynyl, substituted $(C_1-C_3)$ alkynyl and $(C_1-C_3)$ alkoxy;

the phenyl substituents are each independently selected from the group consisting of —F, —Cl, —Br, —CF$_3$, —R, —R', —OR', —SR', NR'$_2$, —NO$_2$, —CN, —C(O)R' and —C(O)OR';

the alkyl, alkenyl and alkynyl substituents are each independently selected from the group consisting of —F, —Cl, —Br, —R', —OR', —SR', NR'$_2$, —NO$_2$, —CN, —C(O)R', —C(O)OR', naphthyl, γ-butyrolactonyl and pyrrolidinyl; and each $R_1$ is independently selected from the group consisting of —H, $(C_1-C_3)$ alkyl, $(C_1-C_3)$ alkenyl and $(C_1-C_3)$ alkynyl.

10. The pharmaceutical composition of claim 9, wherein said compound is selected from the group consisting of compounds
1
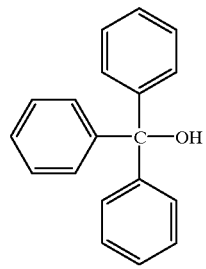
2
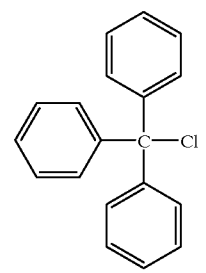
3
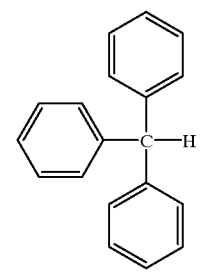
4
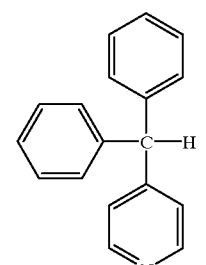
5
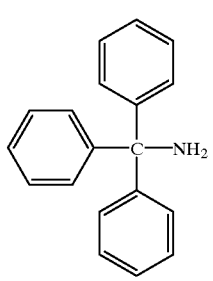
-continued
6
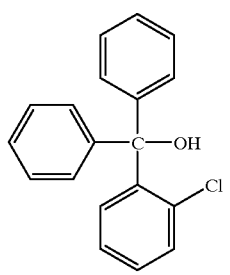
7
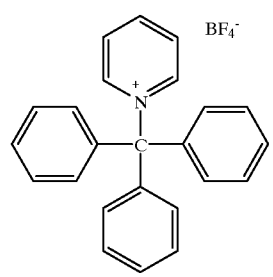
8
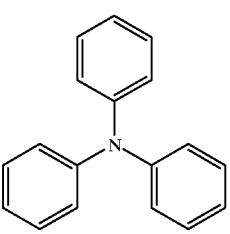
9
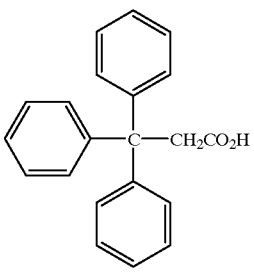
10
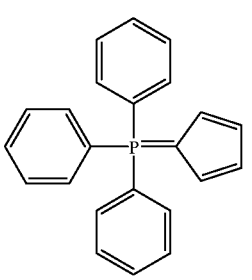

-continued
11
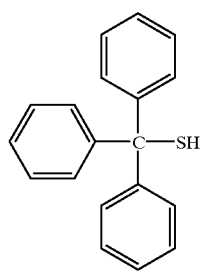
12
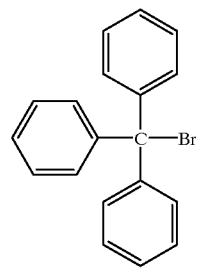
13
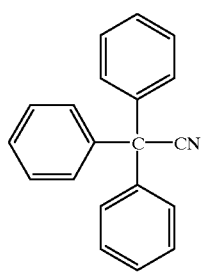
14
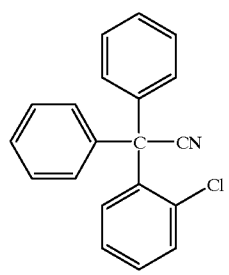
15
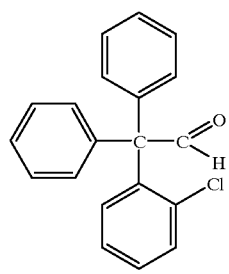
-continued
16
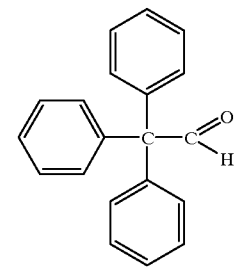
17
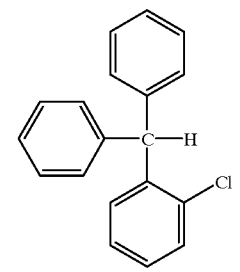
18
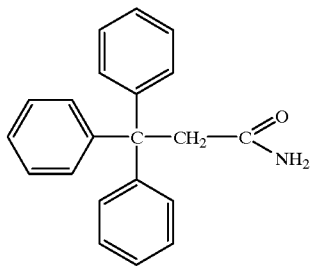
19
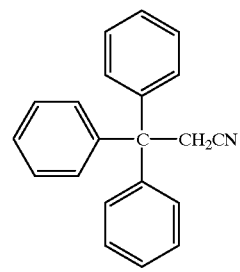
20
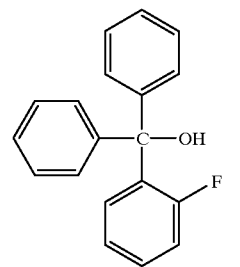

21
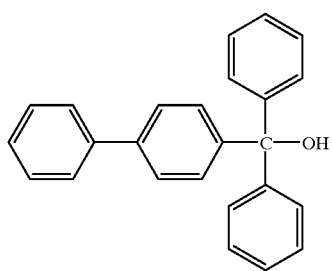
22
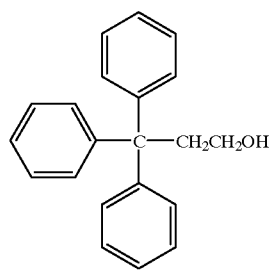
23
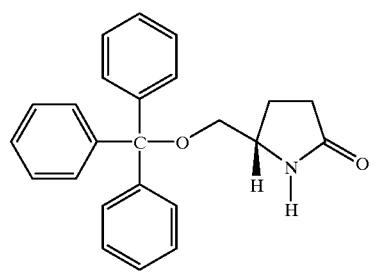
24
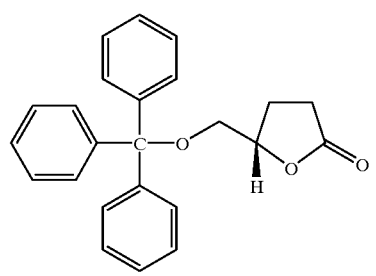
25
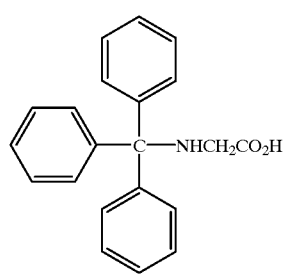
26
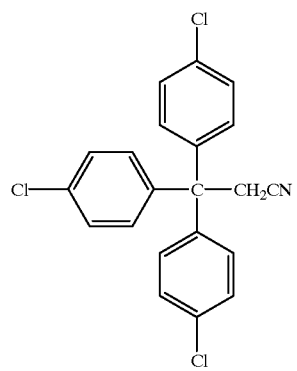
27
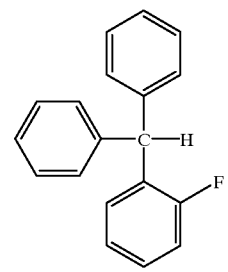
28
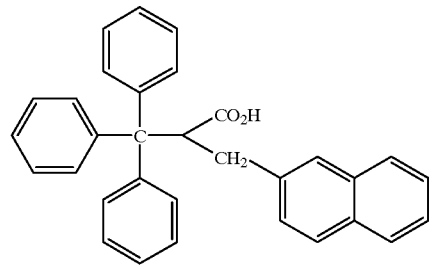
29
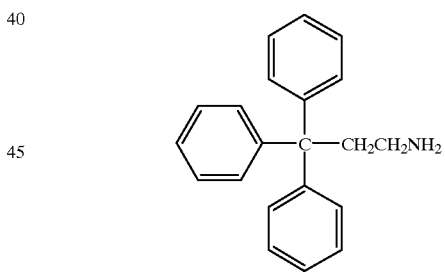
30
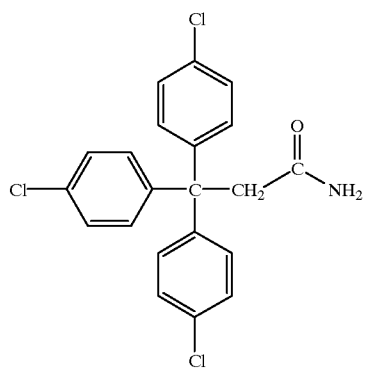

31
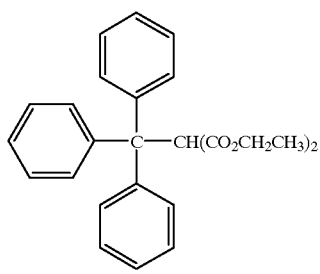
32
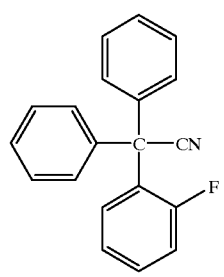
33
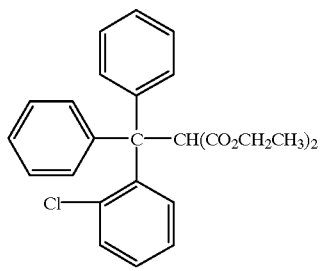
34
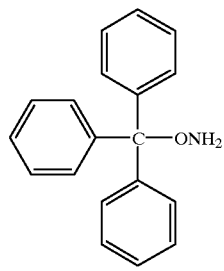
35
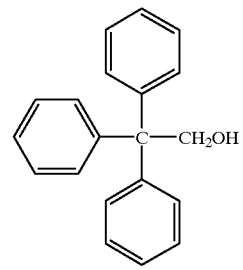
36
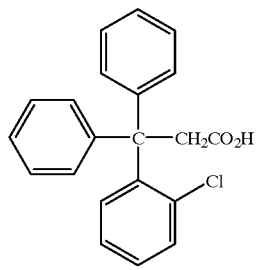
37
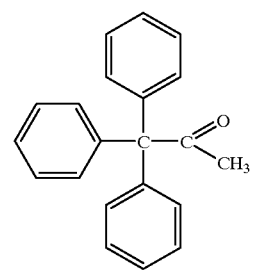
38
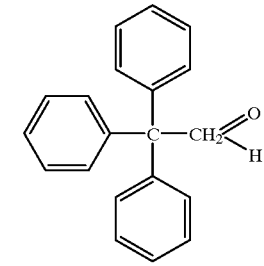
39
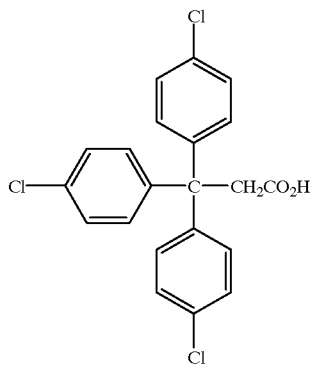
40
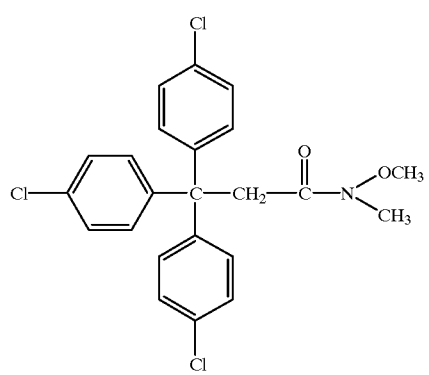

41
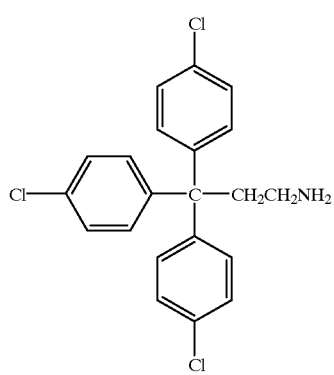
42
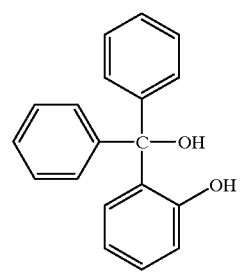
43
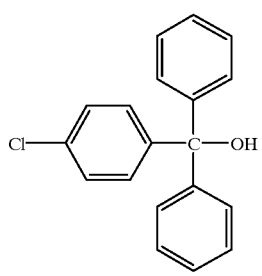
44
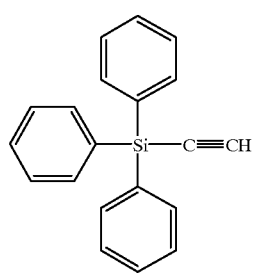
45
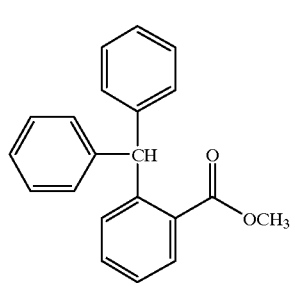
46
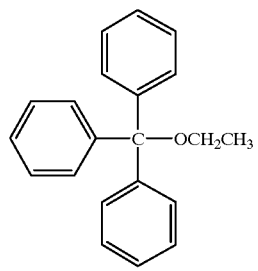
47
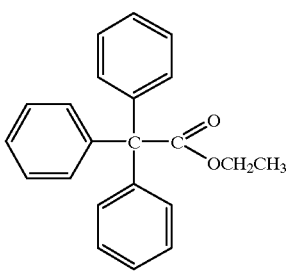
48
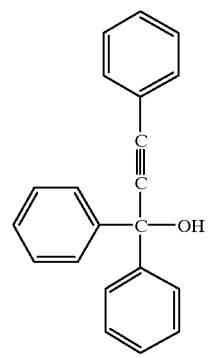
49
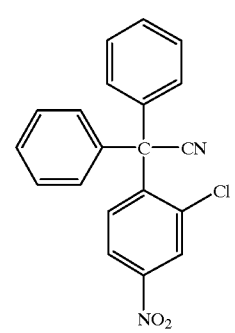
50
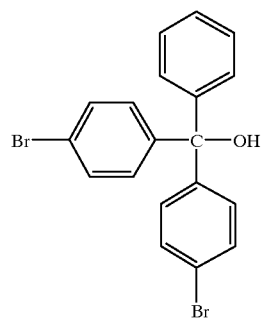

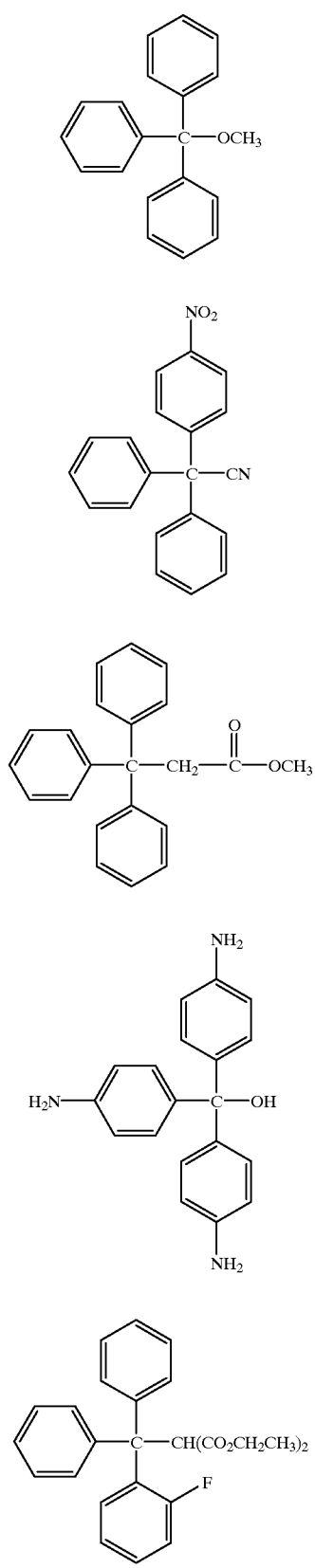
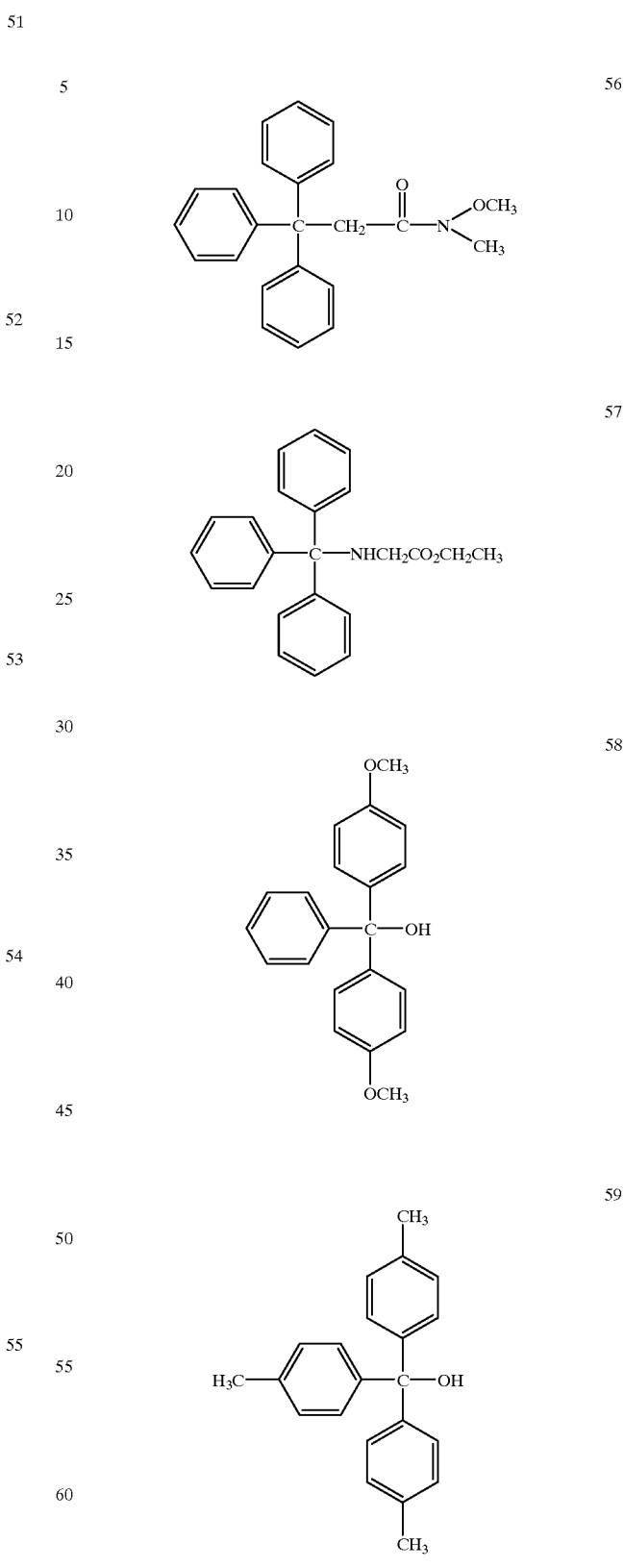

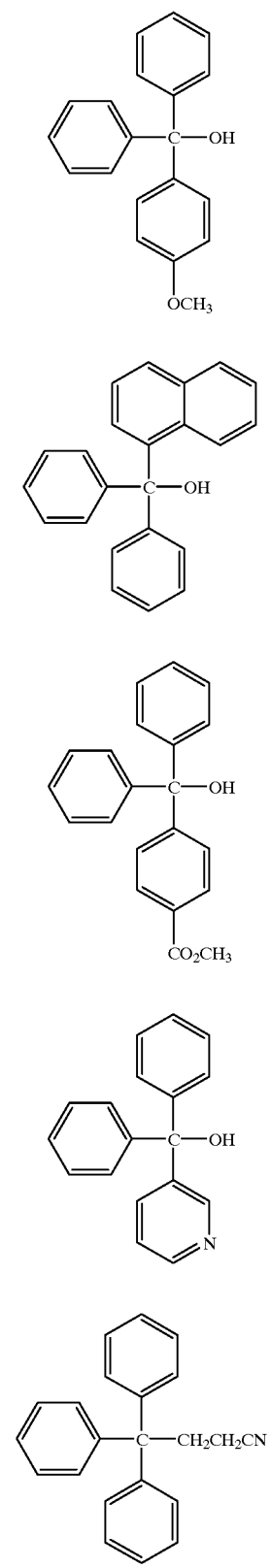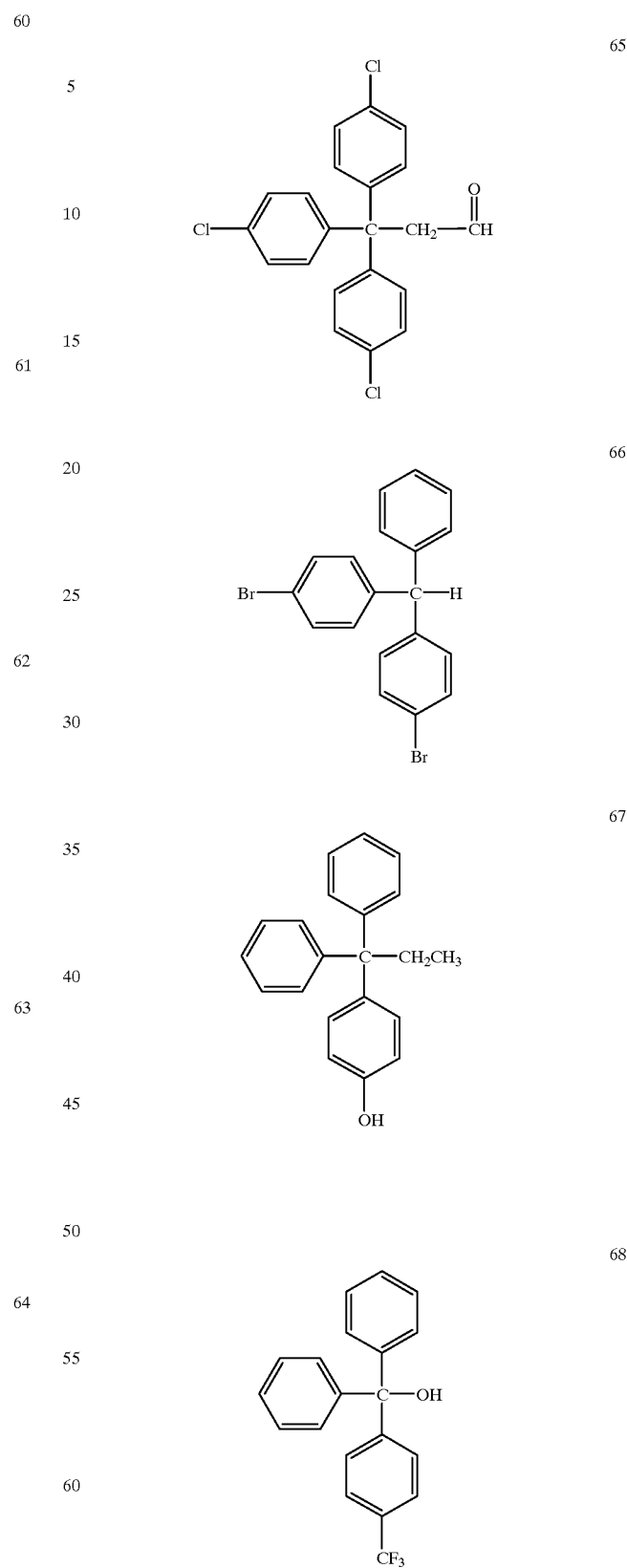

69
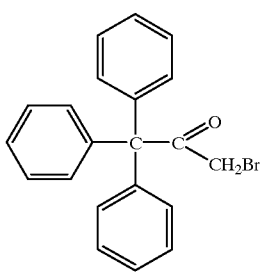
70
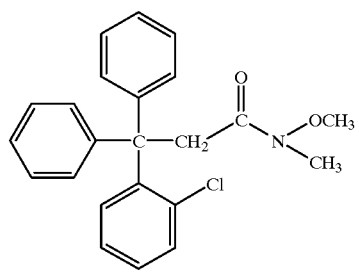
71
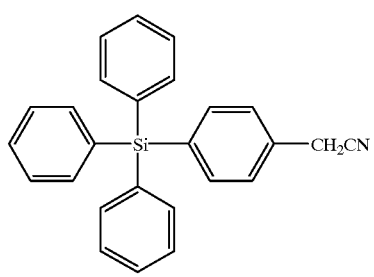
72
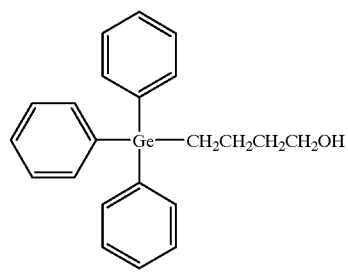
73
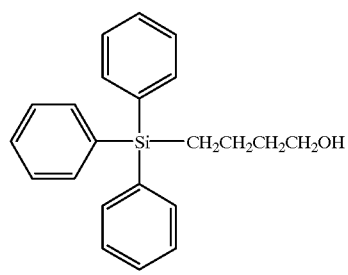
74
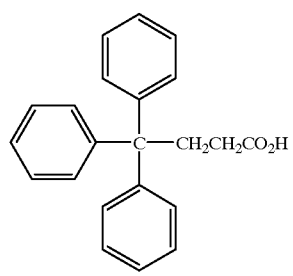
75
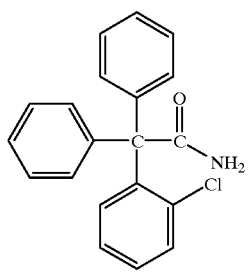
76
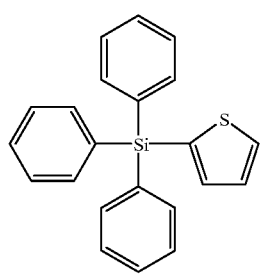
77
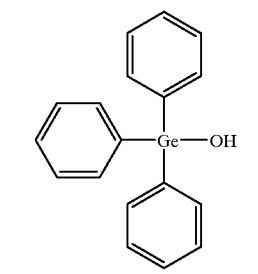
78
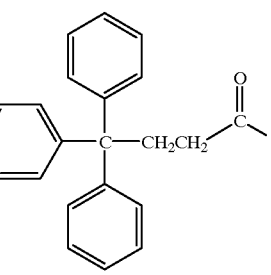

79 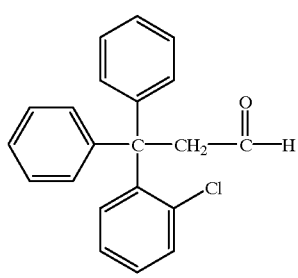
80 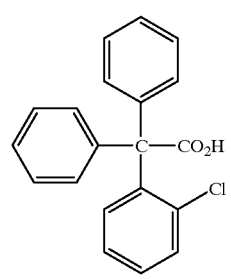
81 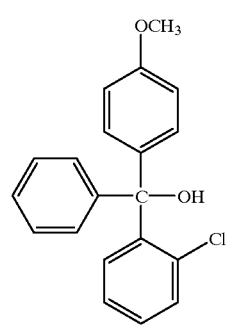
82 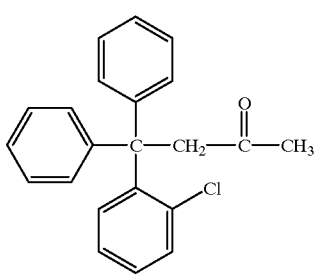
83 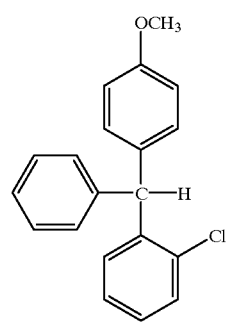
84 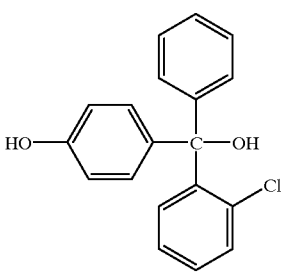
85 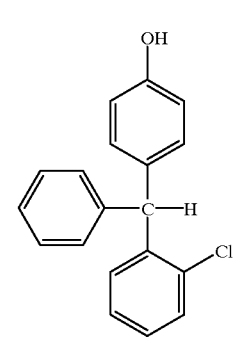
86 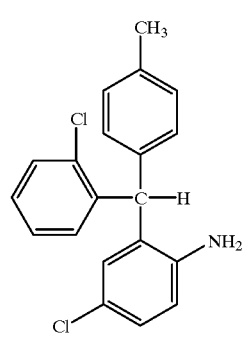
87 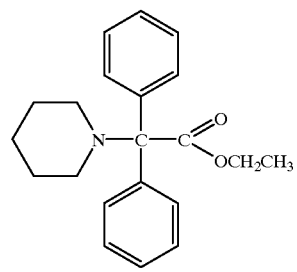
88 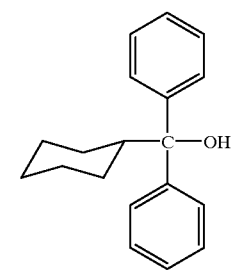

-continued
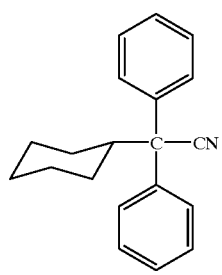
89
and
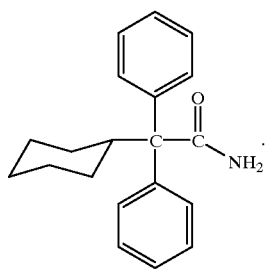
90
11. The pharmaceutical composition of claim 10, wherein said compound is selected from the group consisting of
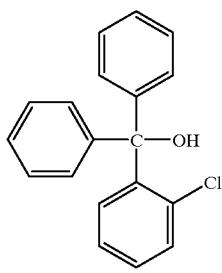
6
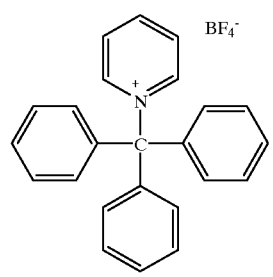
7
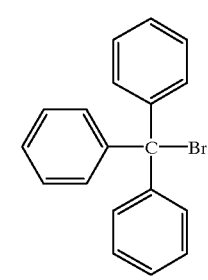
12
-continued
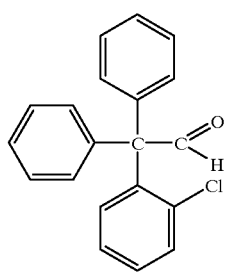
13
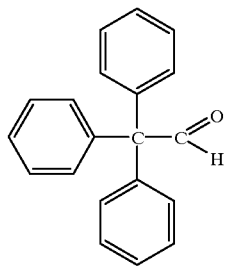
14
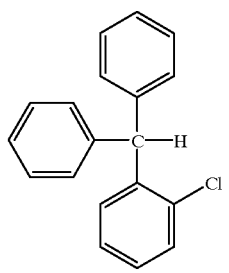
15
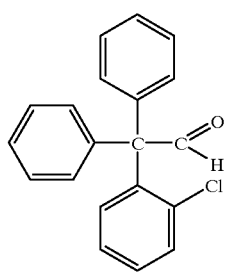
16
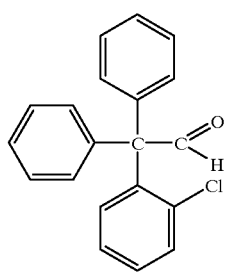
17

18
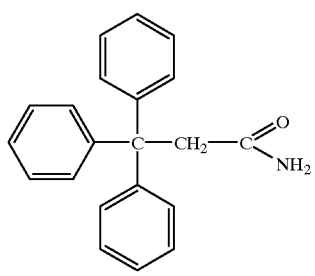
19
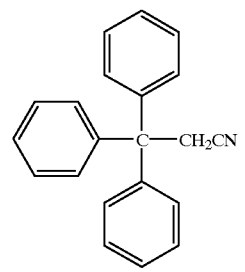
20
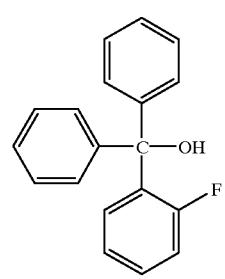
21
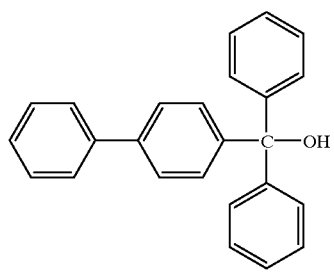
22
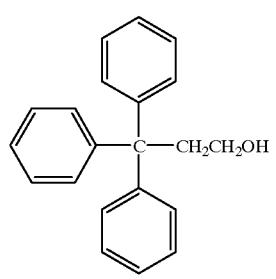
23
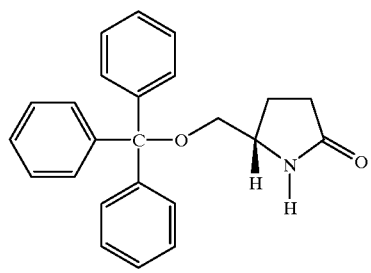
24
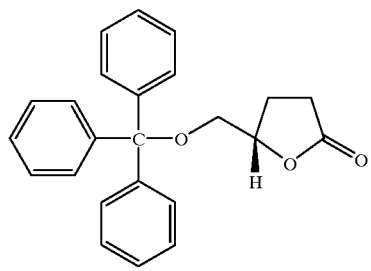
25
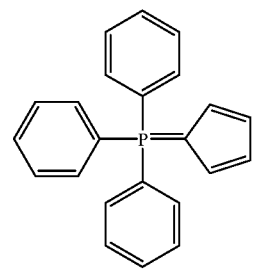
26
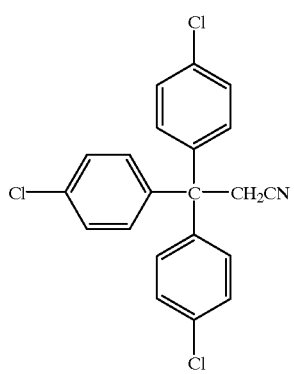
27
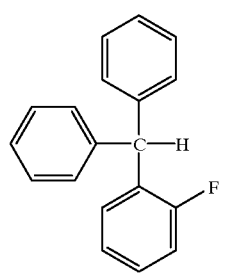

28
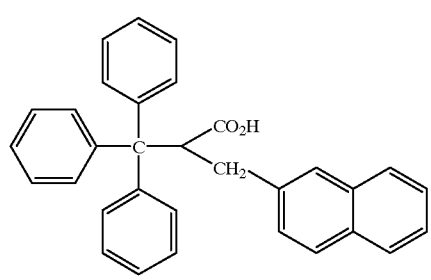
29
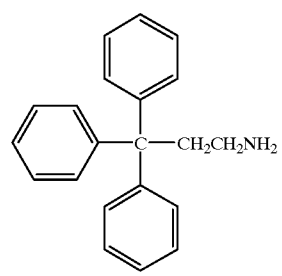
30
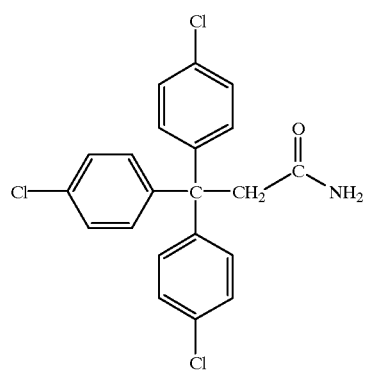
31
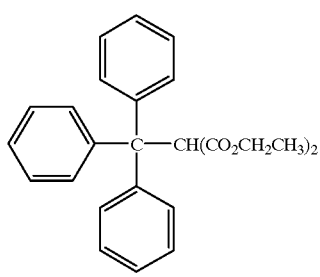
32
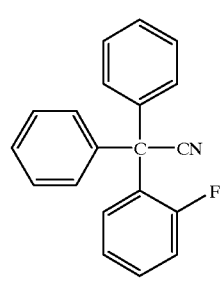
33
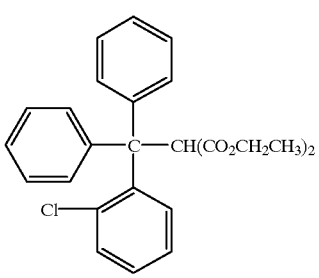
34
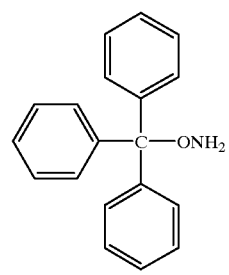
35
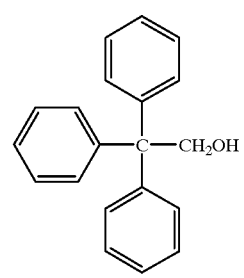
36
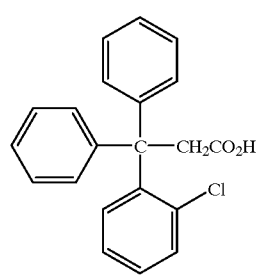
37
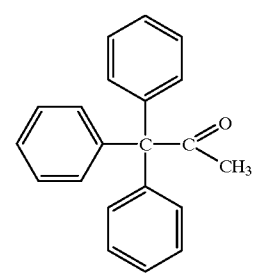

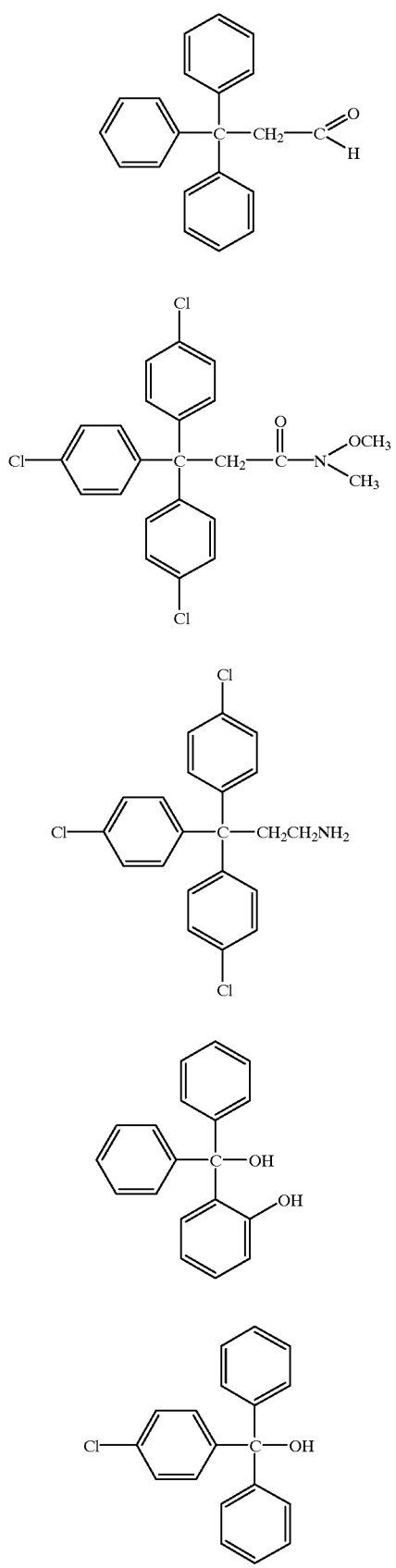
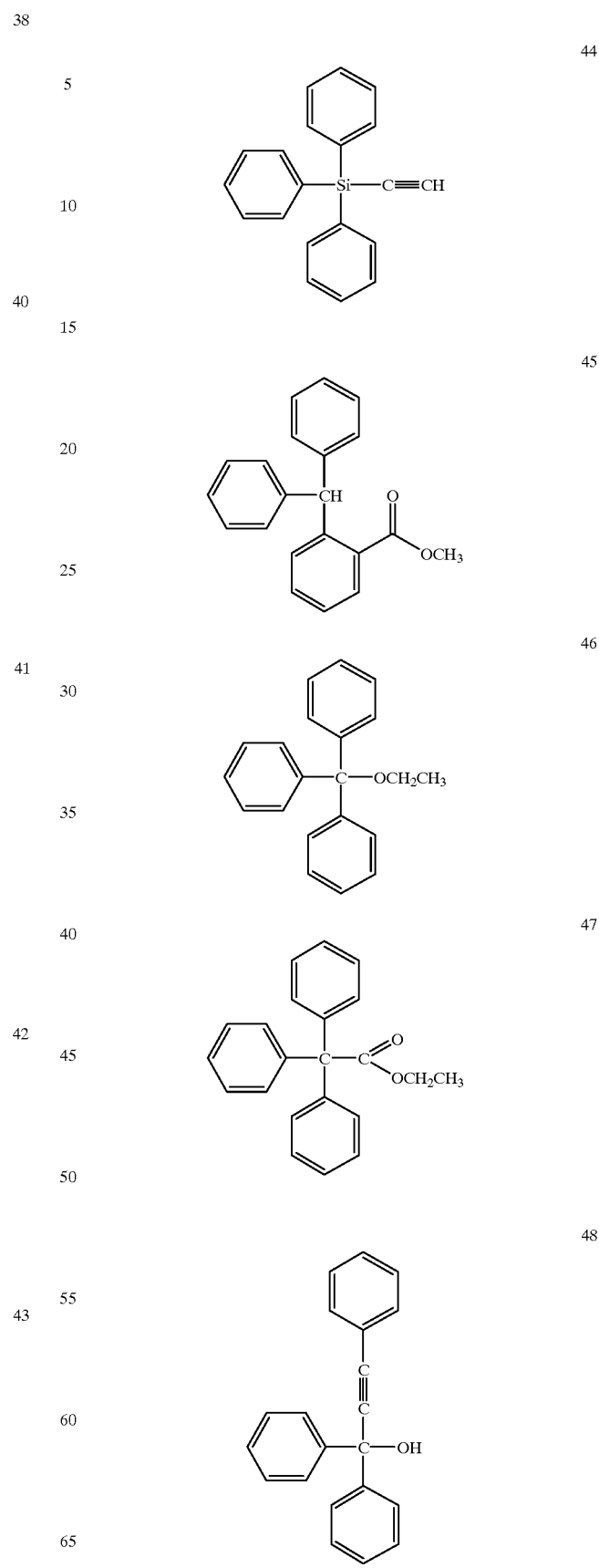

49
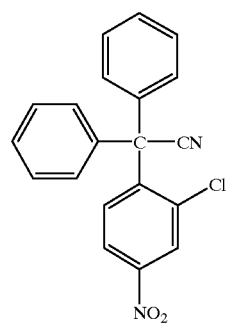
50
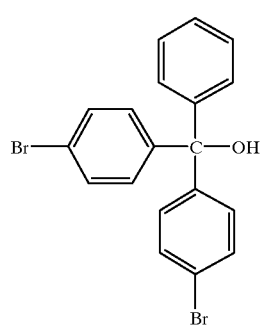
51
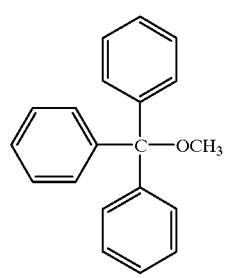
52
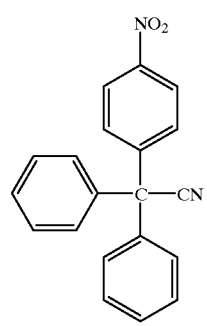
53
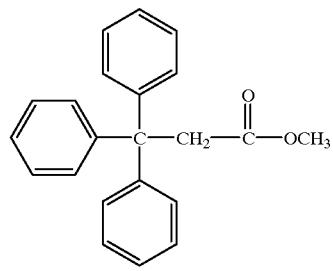
54
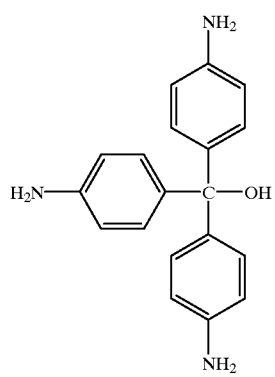
55
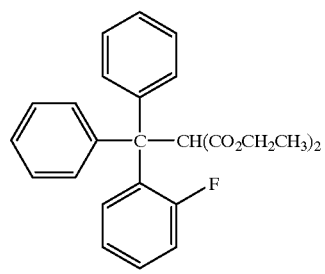
56
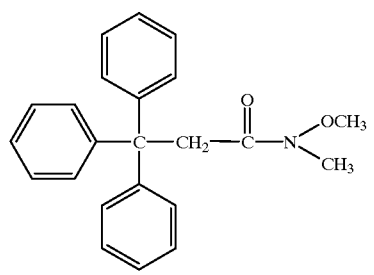
58
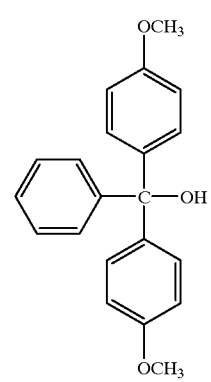

59
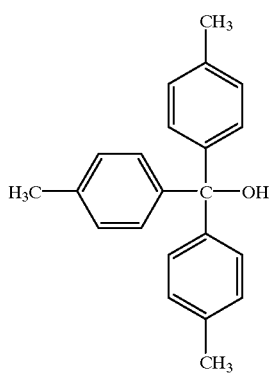
60
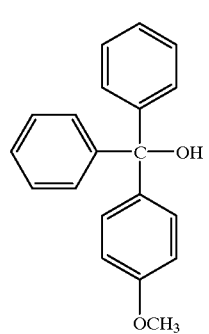
61
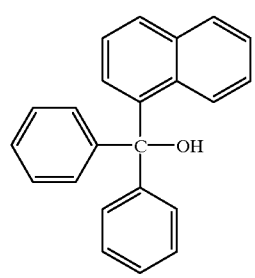
62
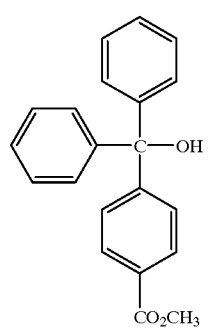
64
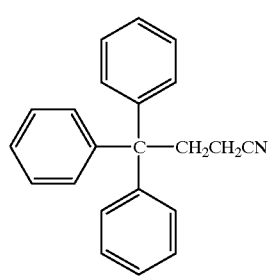
65
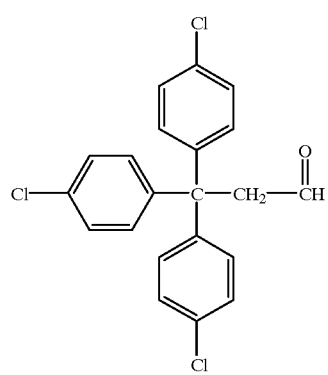
67
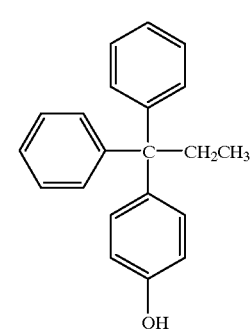
68
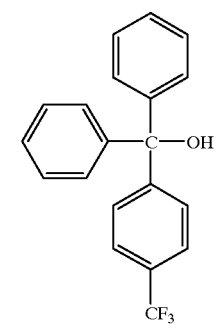
69
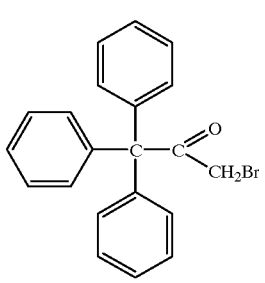
70
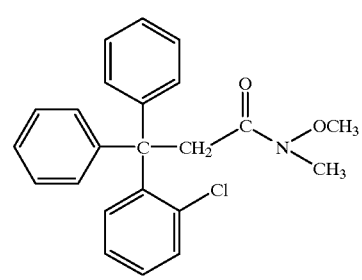

71
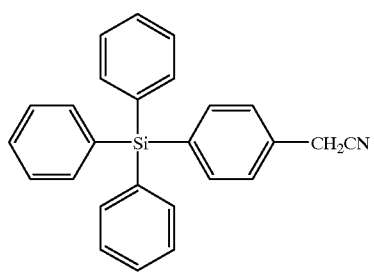
72
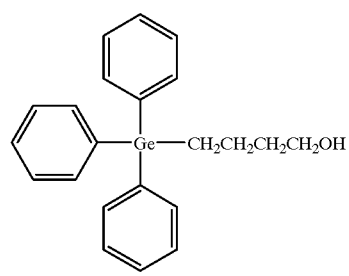
73
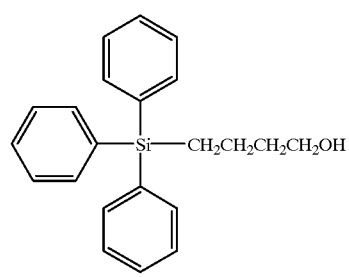
75
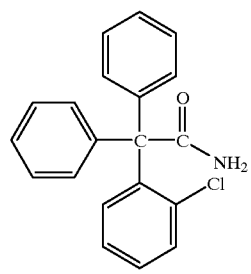
78
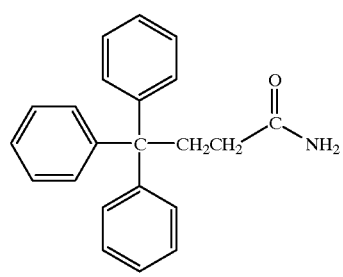
79
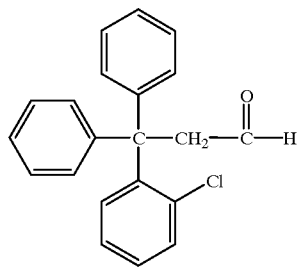
80
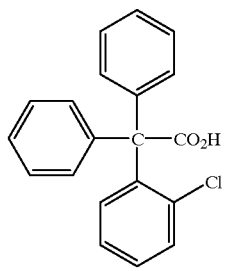
81
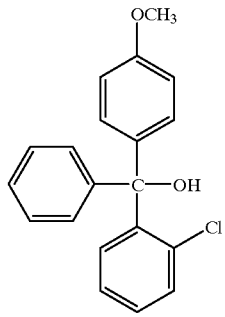
82
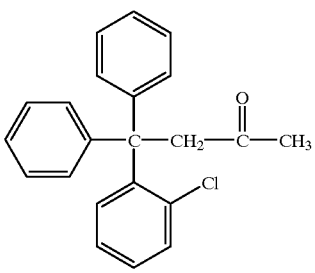
83
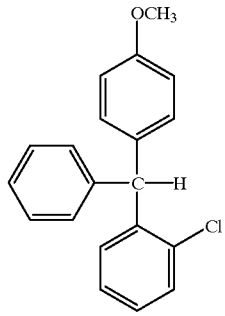

-continued

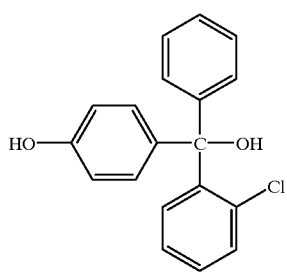
84

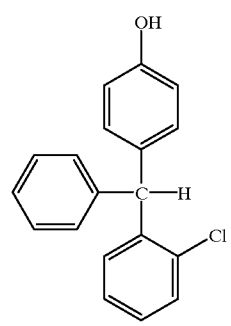
85

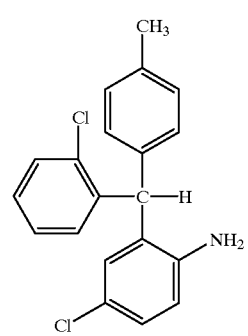
86

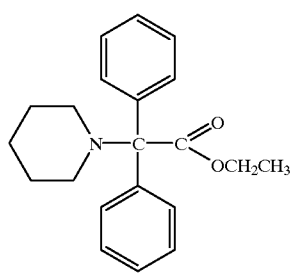
87

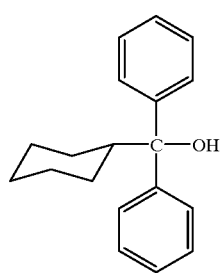
88

-continued

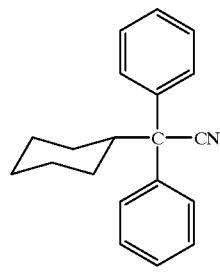
89 and

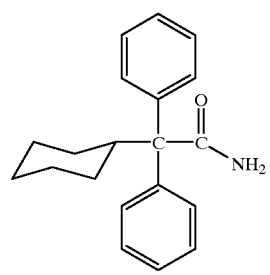
90

12. The pharmaceutical composition of claim 8, wherein said compound is selected from the group consisting of:

a compound having the formula:

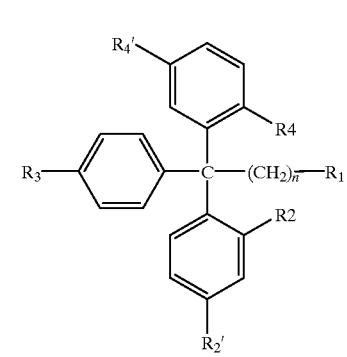

(II)

or a pharmaceutically acceptable salt or hydrate thereof, wherein:

n is 0, 1, 2, 3 or 4;

$R_1$ is —H, —OR, —SR, —CN, —C(O)R, —C(O)OR, —C(O)NR$_2$, —CH[C(O)R]$_2$ or —CH[C(O)OR]$_2$;

$R_2$ is —F, —Cl, —Br, —I, —OR, SR, —C(O)R or —C(O)NR$_2$;

$R_{2'}$ is —H or —NO$_2$;

$R_3$ is —H, (C$_1$–C$_6$) alkyl, (C$_1$–C$_6$) alkenyl, (C$_1$–C$_6$) alkynyl, —OR or —SR;

$R_4$ is —H or —NR$_2$;

$R_{4'}$ is —H, —F, —Cl, —Br or —I; and each R is independently selected from the group consisting of —H, (C$_1$–C$_6$) alkyl, (C$_1$–C$_6$) alkenyl, (C$_1$–C$_6$) alkynyl or (C$_1$–C$_6$) alkoxy; and a compound having the formula:

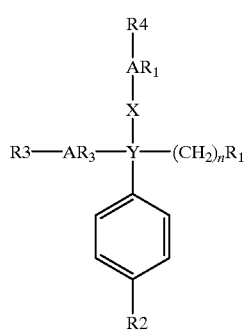

(III)

or a pharmaceutically acceptable salt or hydrate thereof, wherein:

X is absent or —C≡C—;

Y is C, P, Si or Ge;

n is 0, 1, 2, 3 or 4;

Ar₁ is phenyl, substituted phenyl, cycloalkyl or heteroarylium other than imidazolium, nitroimidazolium or triazolium;

Ar₃ is phenyl, naphthyl, piperidyl or cyclohexyl;

R₁ is —R, —OR, —SR, —CN, —NR₂, —ONR₂, —C(O)R, —C(O)OR, —C(O)NR₂, —CH[C(O)R]₂, —CH[C(O)OR]₂, (C₁–C₆) alkyl, (C₁–C₆) alkenyl, (C₁–C₆) alkynyl, cyclopenta-2,4-diene-1-ylidene or phenyl;

each of R₂, R₃ and R₄ is independently selected from the group consisting of —H, —F, —Cl, —Br, —I, —OR, —SR, —NR₂, —NO₂, —C(O)R, —C(O)OR, —C(O)NR₂, trihalomethyl, (C₁–C₆) alkyl, (C₁–C₆) alkenyl, (C₁–C₆) alkynyl and phenyl;

each R is independently selected from the group consisting of —H, halo, (C₁–C₆) alkyl, substituted (C₁–C₆) alkyl, (C₁–C₆) alkenyl, substituted (C₁–C₆) alkenyl, (C₁–C₆) alkynyl, substituted (C₁–C₆) alkynyl and (C₁–C₆) alkoxy;

the alkyl, alkenyl or alkynyl substituents are each independently selected from the group consisting of aryl, —C(O)OR, pyrrolidinyl, butyrolactonyl, —F, —Cl, —Br, —I and —CN; and the phenyl substituents are each independently —R.

13. The pharmaceutical composition of claim 12, wherein said compound has structural the formula:

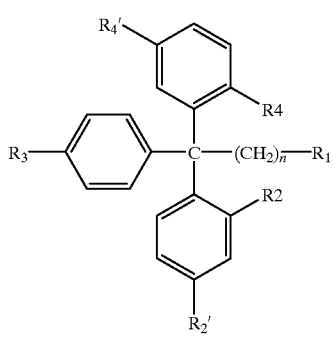

(II)

or a pharmaceutically acceptable salt or hydrate thereof, wherein:

n is 0, 1, 2, 3, or 4;

R₁ is —H, —OR, —SR, —CN, —C(O)R, —C(O)OR, —C(O)NR₂, —CH[C(O)R]₂ or —CH[C(O)OR]₂;

R₂ is —F, —Cl, —Br, —I, —OR, —SR, —C(O)R or —C(O)NR₂;

R₂ is —H or NO₂;

R₃ is —H, (C₁–C₆) alkyl, (C₁–C₆) alkenyl, (C₁–C₆) alkynyl, —OR or —SR;

R₄ is —H, or —NR₂;

R₄ is —H, —F, —Cl, —Br or —I; and each R is independently selected from the group consisting of —H, (C₁–C₆) alkyl, (C₁–C₆) alkenyl, (C₁–C₆) alkynyl or (C₁4 C₆) alkoxy.

14. The pharmaceutical composition of claim 13, wherein said compound is selected from the group consisting of compounds

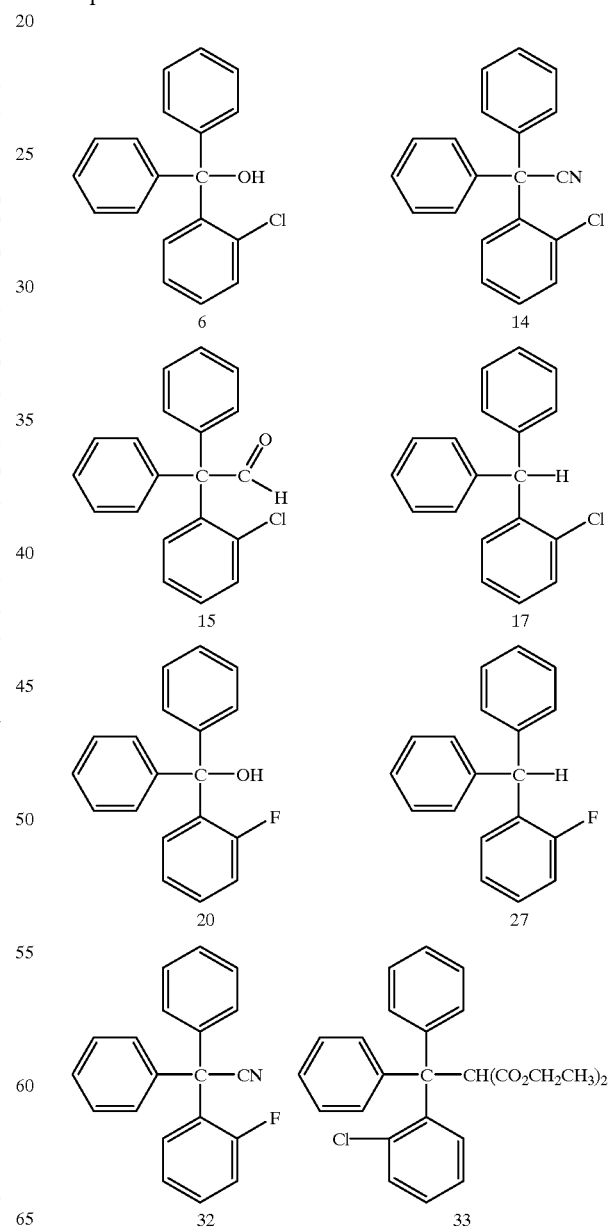

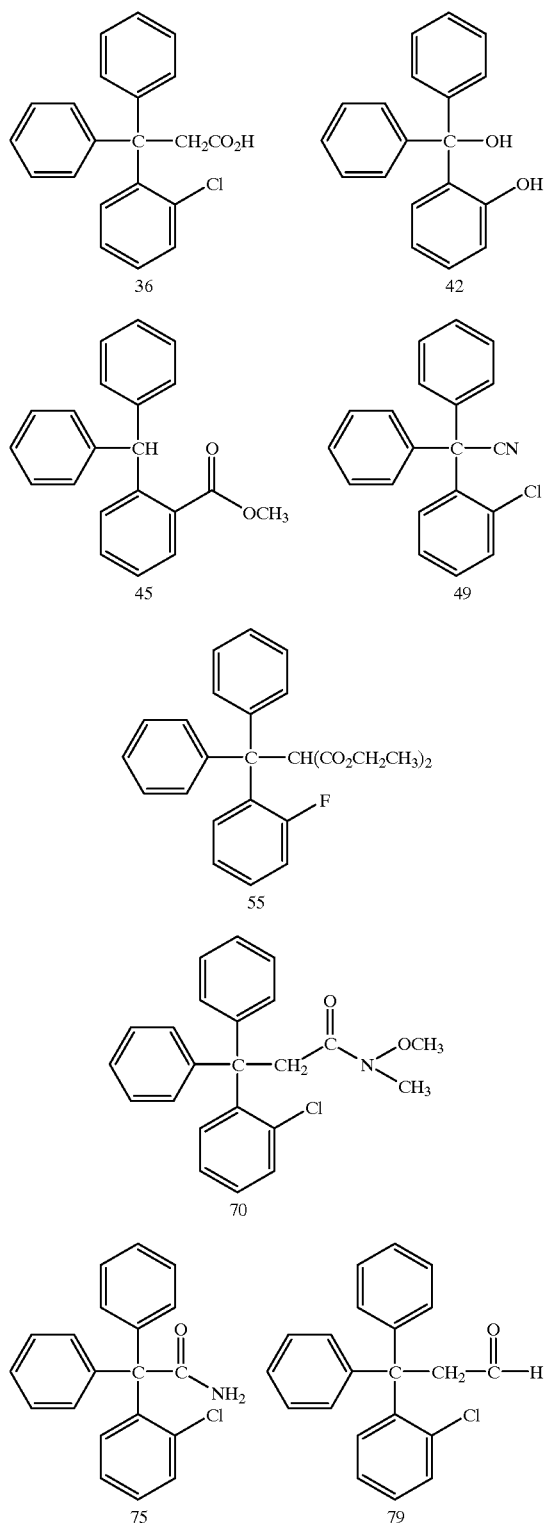
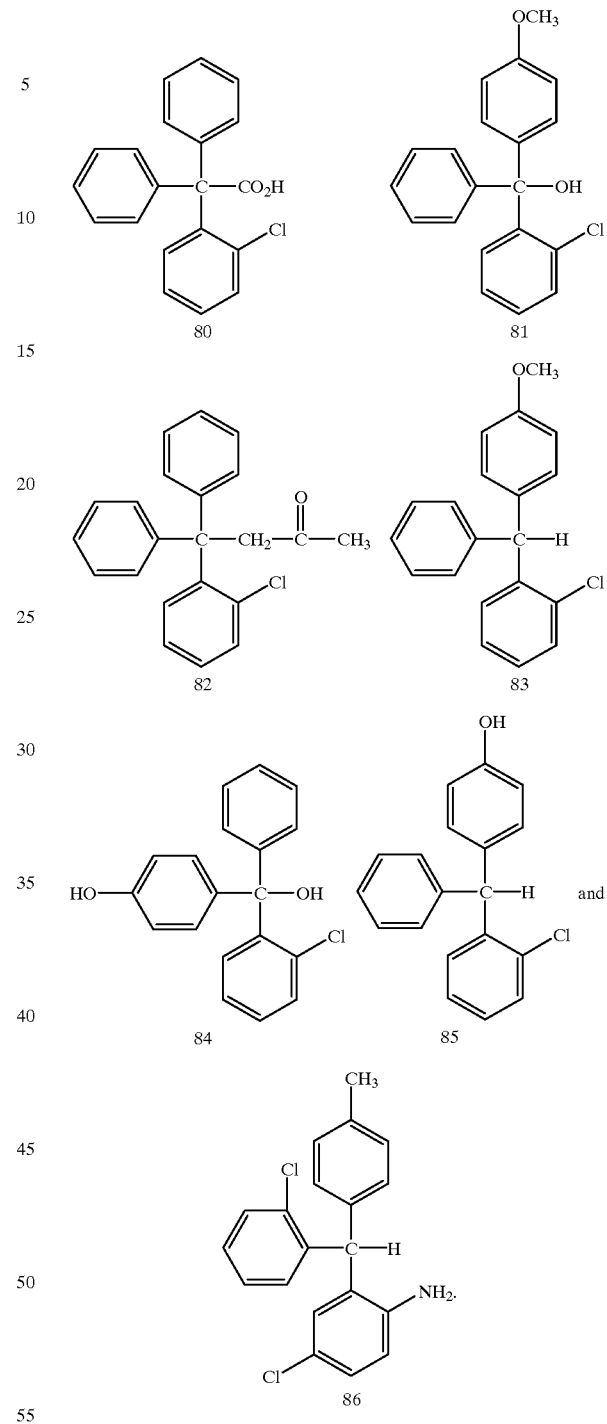
15. The pharmaceutical composition of claim 12, wherein said compound has the structural formula:

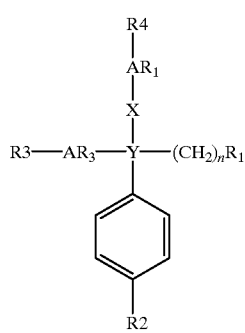

(III)

or a pharmaceutically acceptable salt or hydrate thereof, wherein:

X is absent or —C≡C—;

Y is C, P, Si or Ge;

n is 0, 1, 2, 3 or 4;

$Ar_1$ is phenyl, substituted phenyl, cycloalkyl or heteroarylium other than imidazolium, nitroimidazolium or triazolium;

$Ar_3$ is phenyl, naphthyl, piperidyl or cyclohexyl;

$R_1$ is —R, —OR, —SR, —CN, —$NR_2$, —$ONR_2$, —C(O)R, —C(O)OR, —C(O)$NR_2$, —CH[C(O)R]$_2$, —CH[C(O)OR]$_2$, ($C_1$–$C_6$) alkyl, ($C_1$–$C_6$) alkenyl, ($C_1$–$C_6$) alkynyl, cyclopenta-2,4-diene-1-ylidene or phenyl;

each of $R_2$, $R_3$ and $R_4$ is independently selected from the group consisting of —H, —F, —Cl, —Br, —I, —OR, —SR, —$NR_2$, —$NO_2$, —C(O)R, —C(O)OR, —C(O)$NR_2$, trihalomethyl, ($C_1$–$C_6$) alkyl, ($C_1$–$C_6$) alkenyl, ($C_1$–$C_6$) alkynyl and phenyl;

each R is independently selected from the group consisting of —H, halo, ($C_1$–$C_6$) alkyl, substituted ($C_1$–$C_{C6}$) alkyl, ($C_1$–$C_6$) alkenyl, substituted ($C_1$–$C_6$) alkenyl, ($C_1$–$C_6$) alkynyl, substituted ($C_1$–$C_6$) alkynyl and ($C_1$–$C_6$) alkoxy;

the alkyl, alkenyl or alkynyl substituents are each independently selected from the group consisting of aryl, —C(O)OR, pyrrolidinyl, butyrolactonyl, —F, —Cl, —Br, —I and —CN; and the phenyl substituents are each independently —R.

16. The pharmaceutical composition of claim 15, wherein said compound is selected from the group consisting of compounds

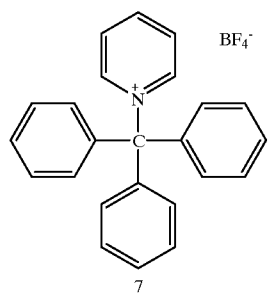

7

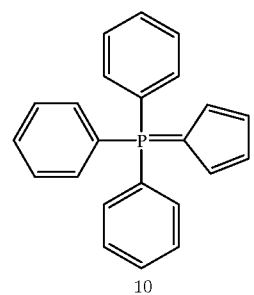

10

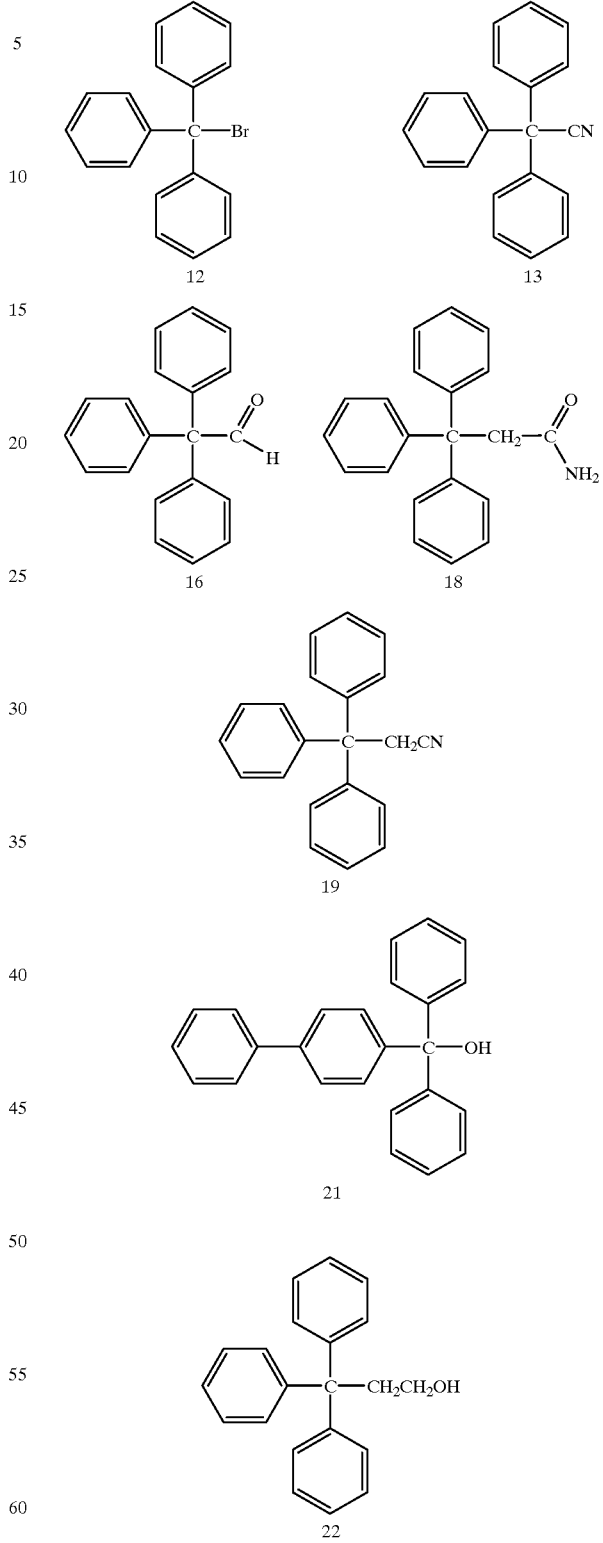

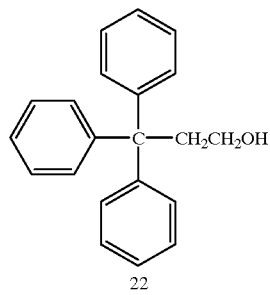

22

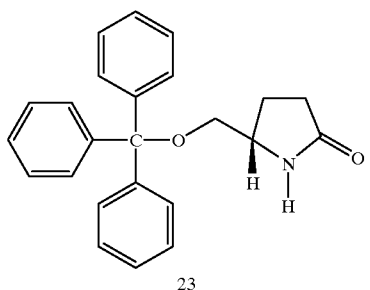
23
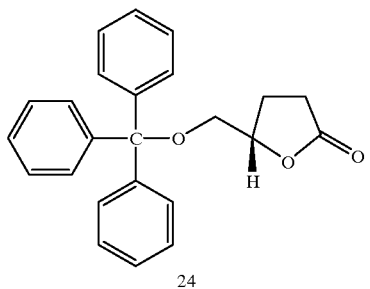
24
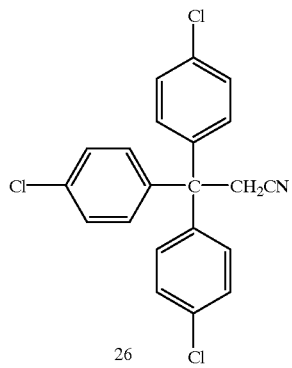
26
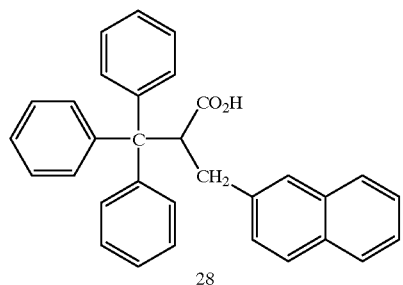
28
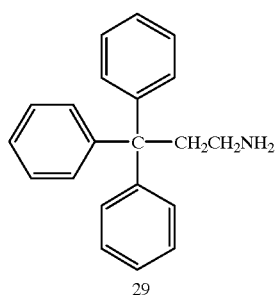
29
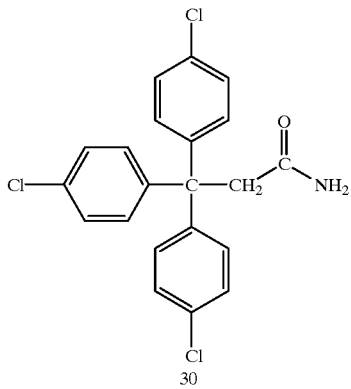
30
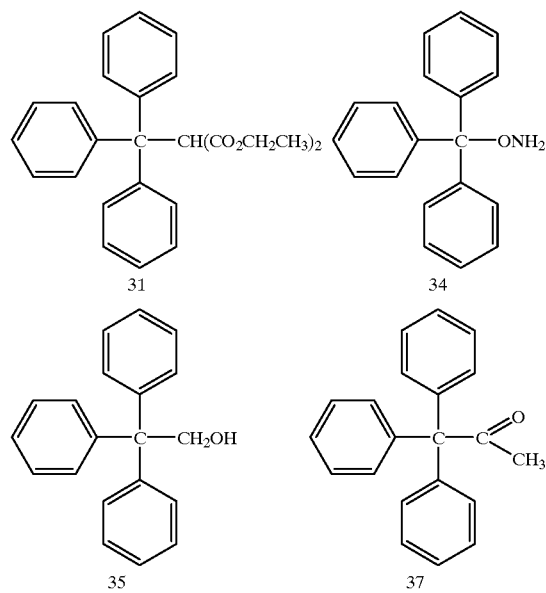
31    34
35    37
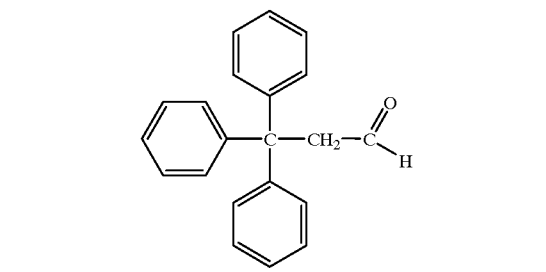
38
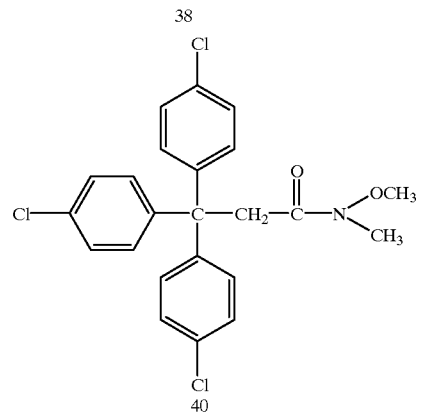
40

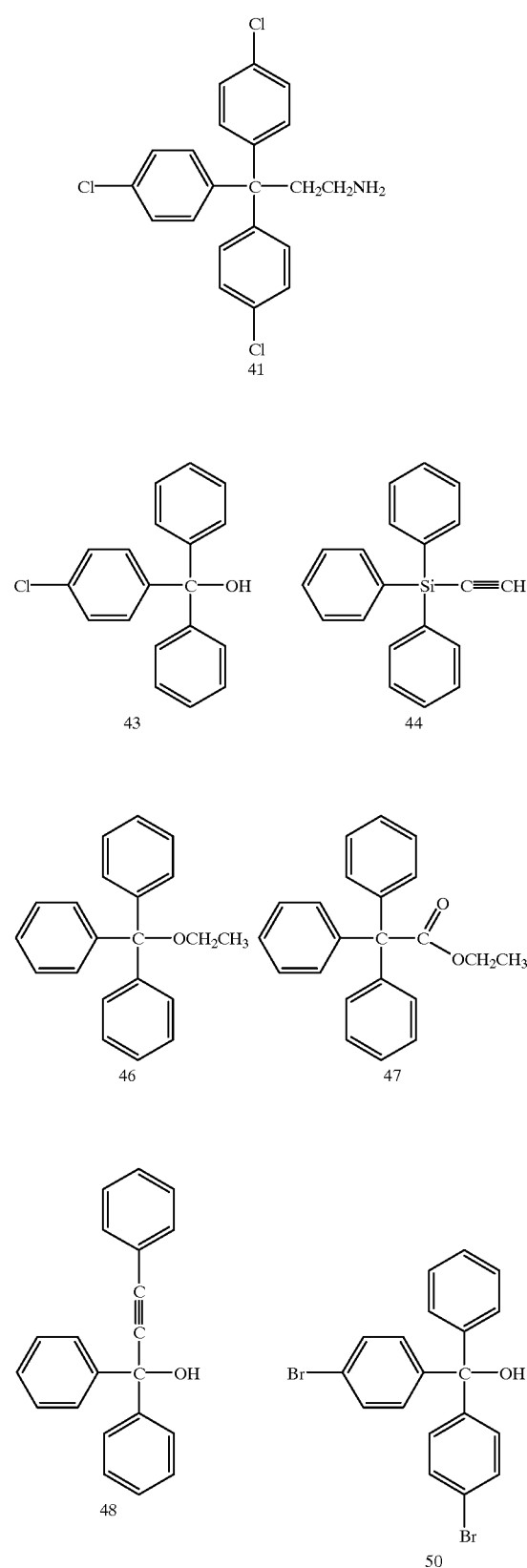
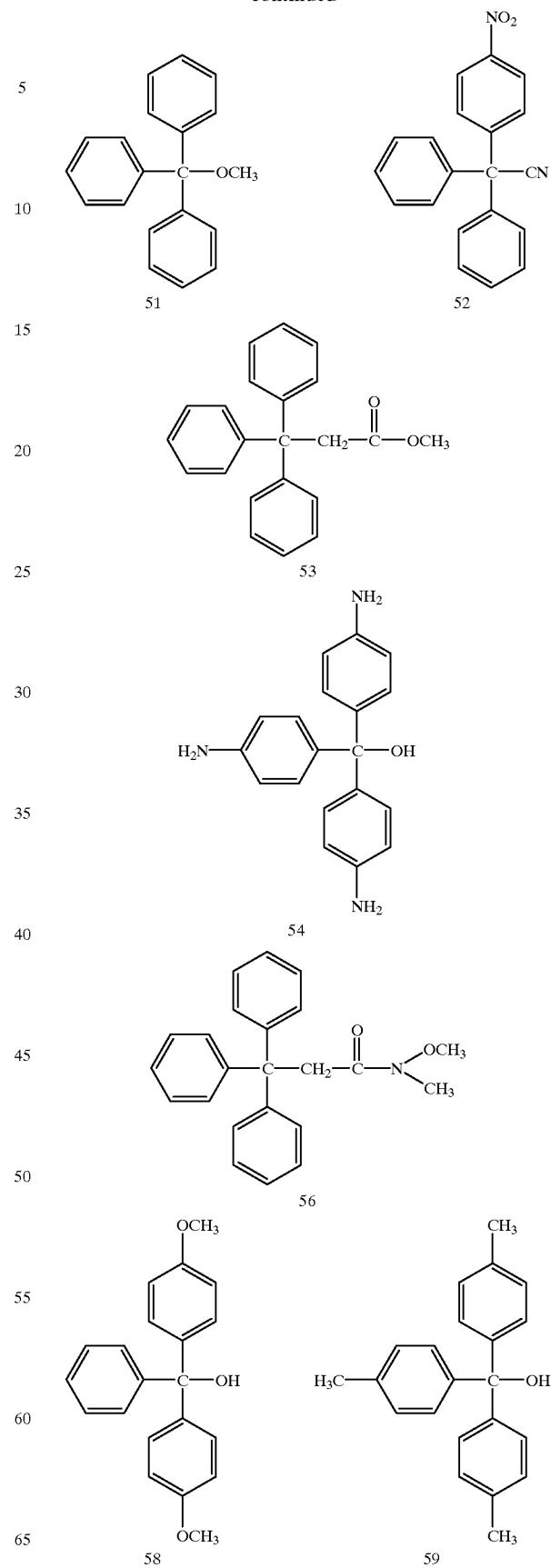

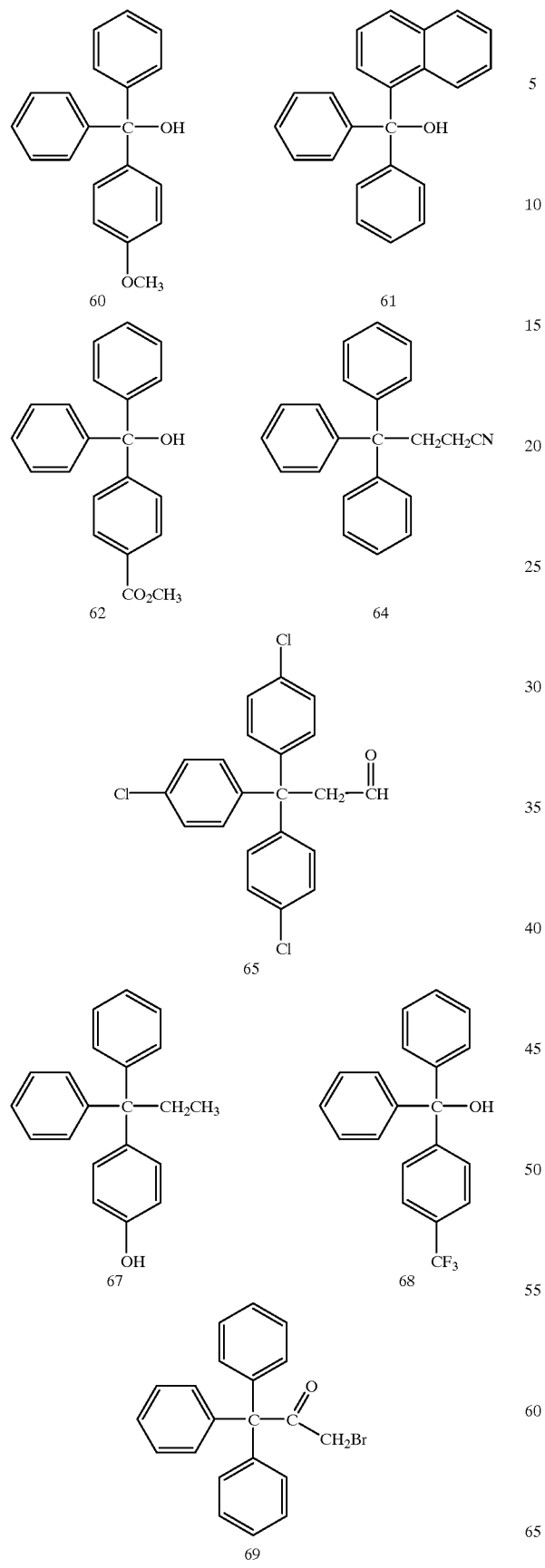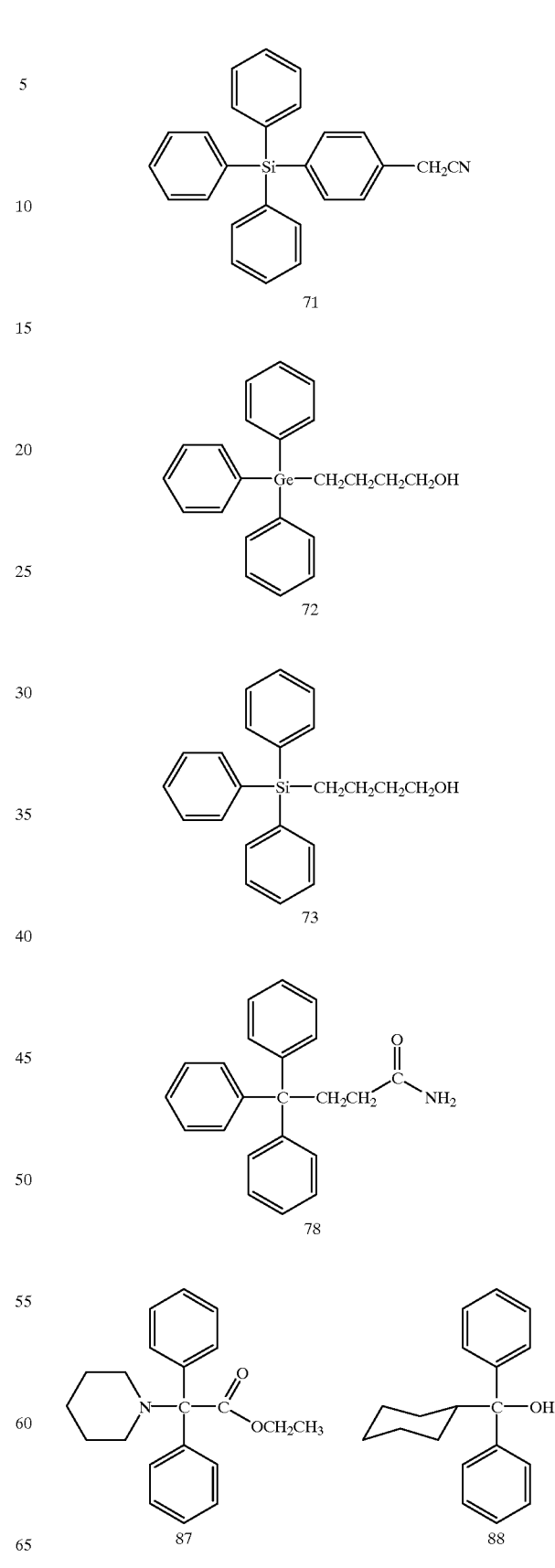

-continued

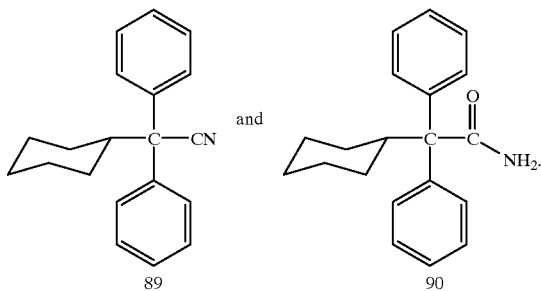

17. A method of inhibiting calcium-activated potassium transport of a cell, said method comprising the step of contacting a cell in situ with an effective amount of a compound having the formula:

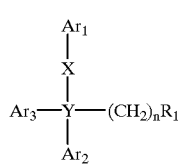

(I)

or a pharmaceutically acceptable salt or hydrate thereof, wherein:
n is 0, 1, 2, 3 or 4;
X is absent, $(C_1-C_3)$, $C_1-C_3$) alkenyl, or $C_1-C_3$) alkynyl;
Y is C, N, P, Si or Ge;
$R_1$ is absent, —halo, —R, —OR, —SR, —NR$_1$, —ONR$_2$, —NO$_2$, —CN, —C(O)R, —C(S)R, —C(O)OR, —C(S)OR, —C(O)SR, —C(S)SR, —C(O)NR$_2$, C(S) NR$_2$, —C(O)NR(OR), —C(S)NR(OR), —C(O)NR (SR), —C(S)NR(SR), —CH(CN)$_2$, —CH[C(O)R]$_2$, —CH[C(S)R]$_2$, —CH[C(O)OR]$_2$, —CH[C(S)OR]$_2$, —CH[C(O)SR]$_2$, —CH[C(O)SR]$_2$ or aryl;
$Ar_1$ is aryl, substituted aryl, heteroarly other than imidazole, nitroimidazole and triazole, heteroarylium other than imidazolium, nitroimidazolium and triazolium, $(C_5-C_5)$ cycloakyl or $(C_5-C_5)$ heterocycloalkyl;
$Ar_2$ is aryl or substituted aryl;
$Ar_3$ is aryl, substituted aryl, biaryl or heteroaryl other than imidazole, nitroimidazole and triazole;
each R is independently selected from the group consisting of —H. $(C_1-C_6)$ alkyl, substituted $(C_1-C_6)$ alkyl, $(C_1-C_6)$ alkenyl, substituted $(C_1-C_6)$ alkenyl, $(C_1-C_6)$ alkynyl, substituted $(C_1-C_6)$ alkynyl and $(C_1-C_6)$ alkoxy;
the aryl substituents are each independently selected from the group consisting of —halo, trihalomethyl, —R, —R —OR, —SR, —NR$_2$, —NO$_2$, —CN, —C(O)R, —C(S)R, —C(O)OR, —C(S)OR, —C(O)SR, and- —C(O)SR;
the alkyl, alkenyl and alkynyl substituents are each independently selected from the group consisting of —halo, —R —OR, —SR, —NR$_2$, —NO$_2$, —CN, —C(O)R, —C(S)R, —C(O)OR, —C(S)OR, —C(O)SR, —C(S) SR, aryl, γ-butyrolactonyl, pyrrolidinyl and succinic anhydridyl; and
each R is independently selected from the group consisting of —H, $(C_1-C_6)$ alkyl, $(C_1-C_6)$ alkenyl and $(C_1-C_6)$ alkynyl.

18. the method of claim 17, wherein said cell is an erythrocyte.

19. The method of claim 17, wherein said compound is selected from the group consisting of

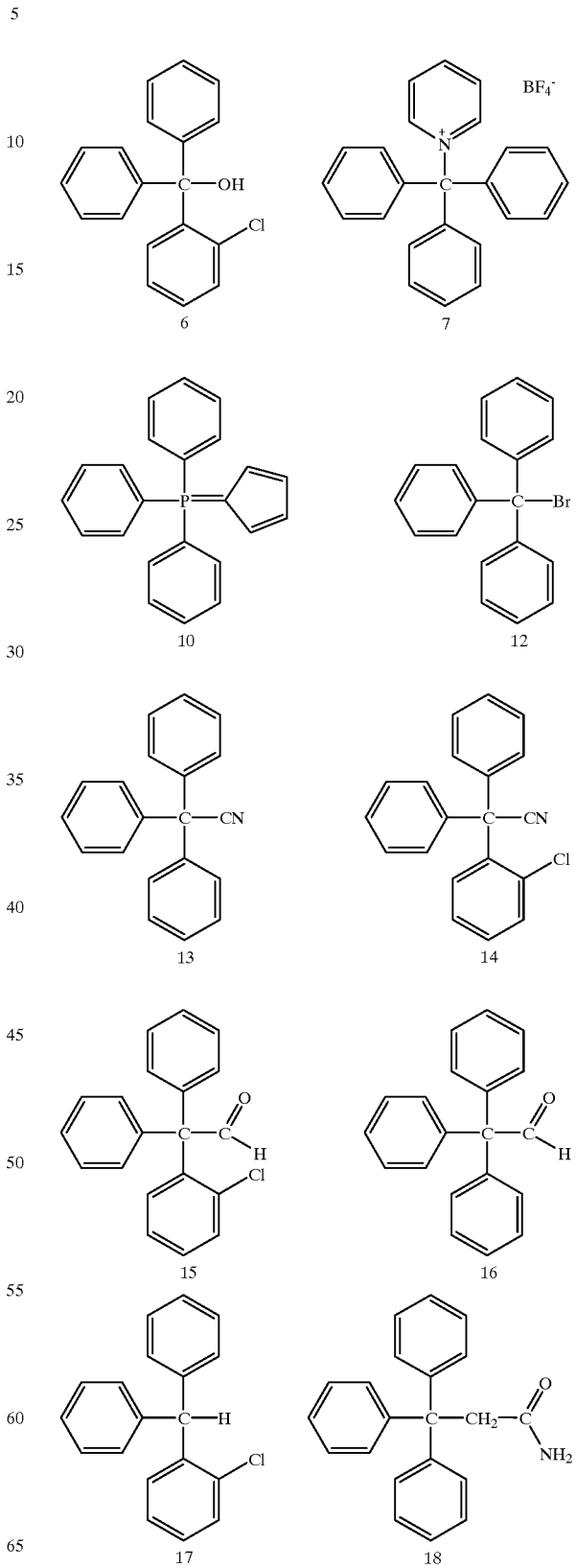

-continued
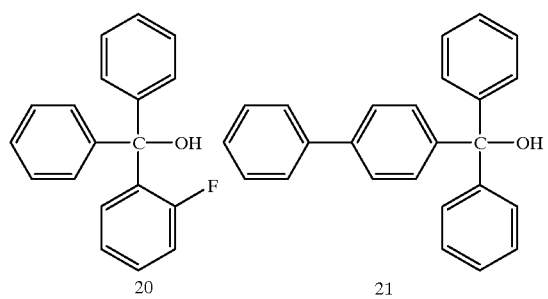
20  21
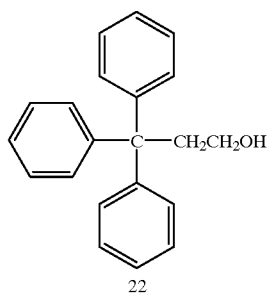
22
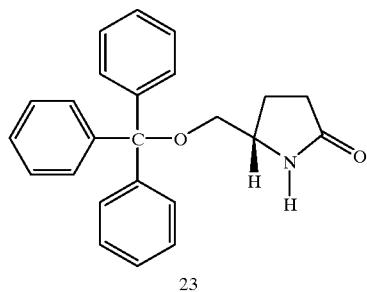
23
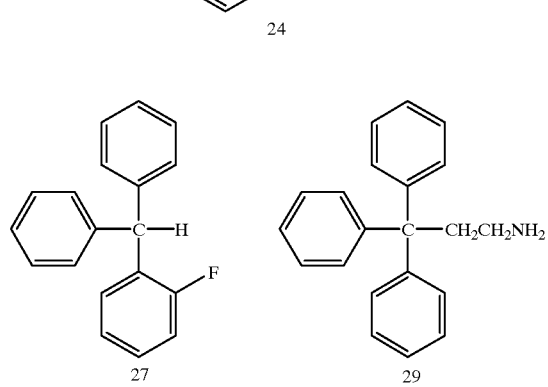
27  29
-continued
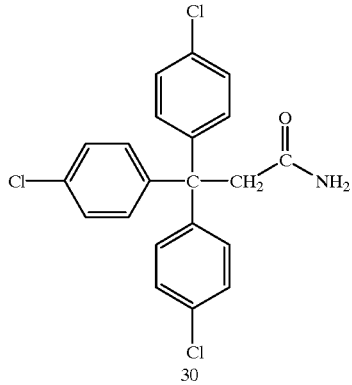
30
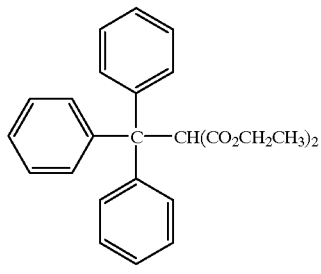
31
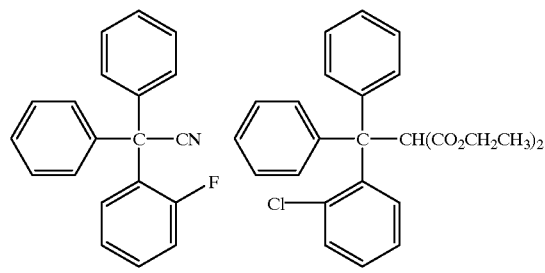
32  33
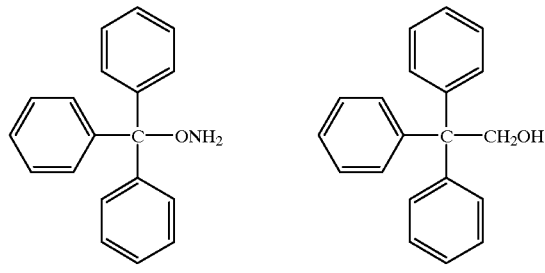
34  35
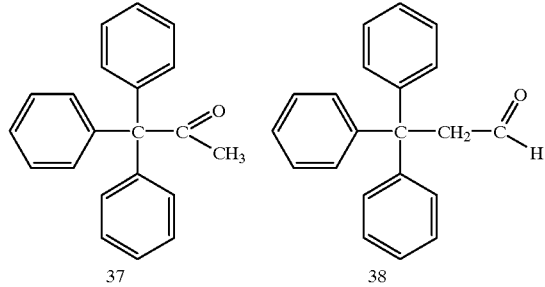
37  38

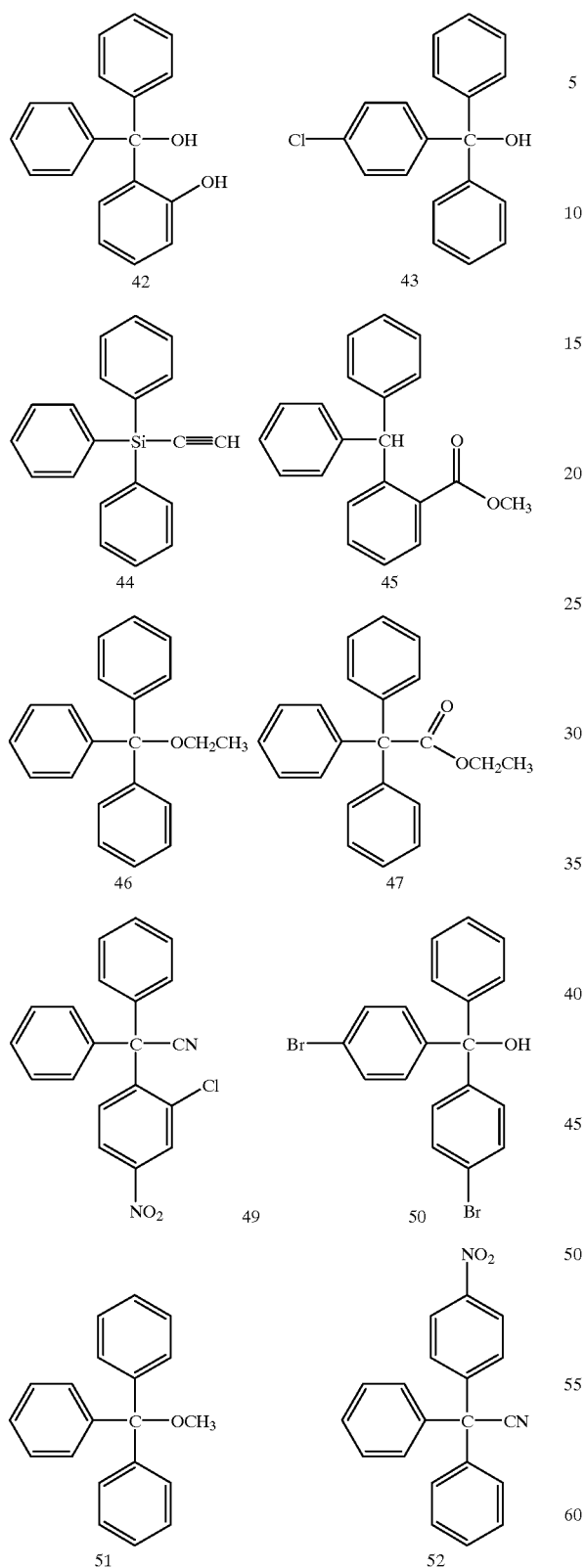
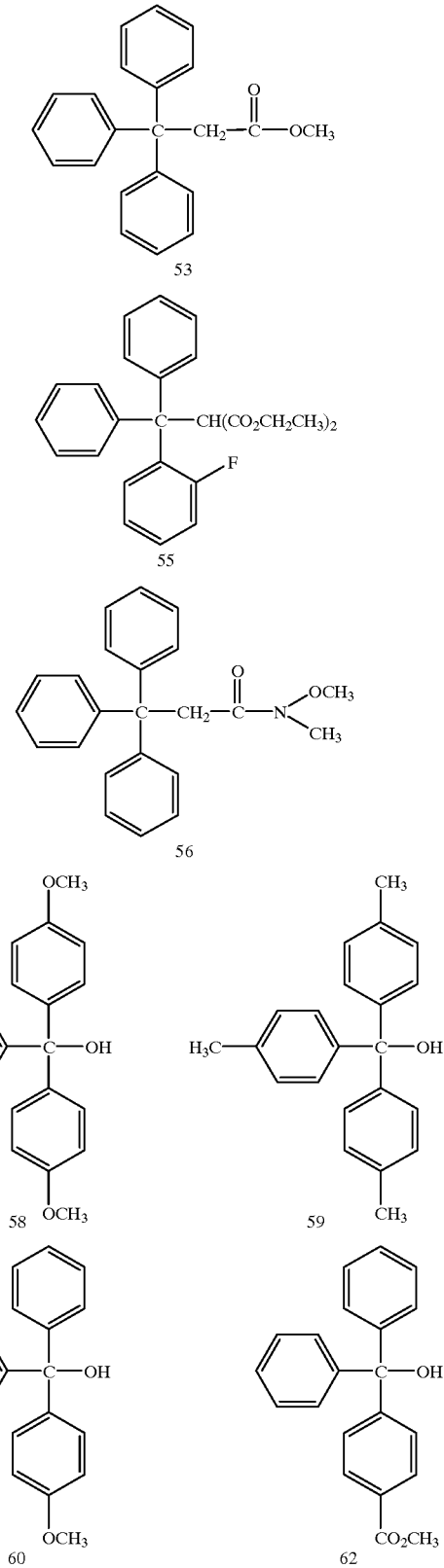

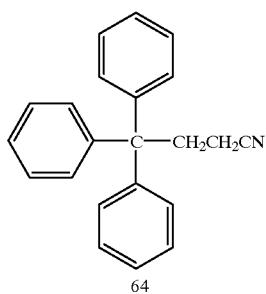
64
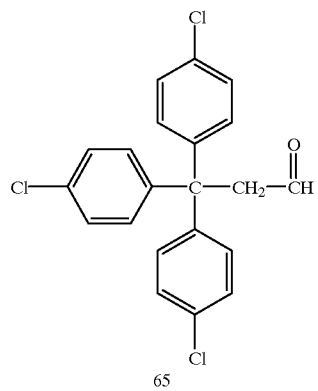
65
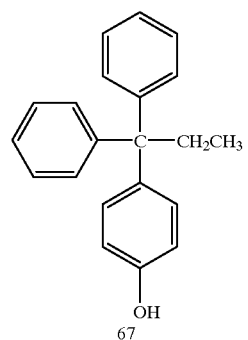
67
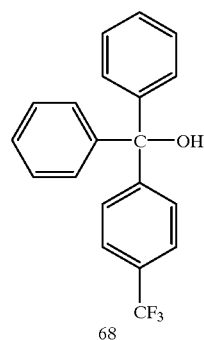
68
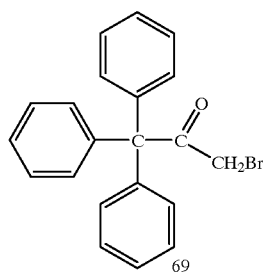
69
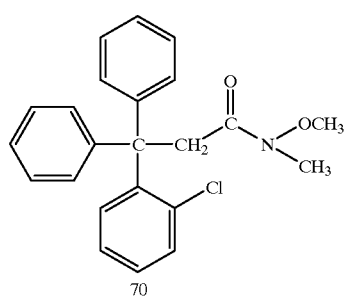
70
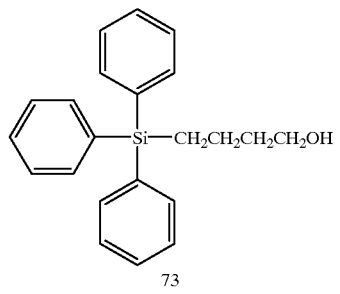
73
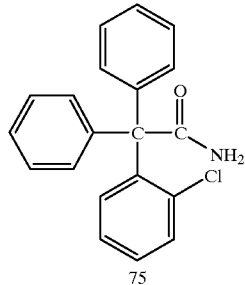
75
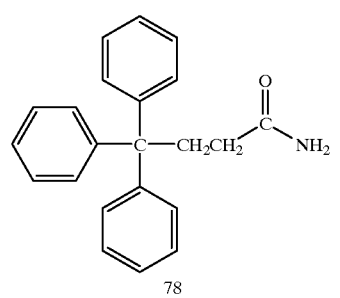
78
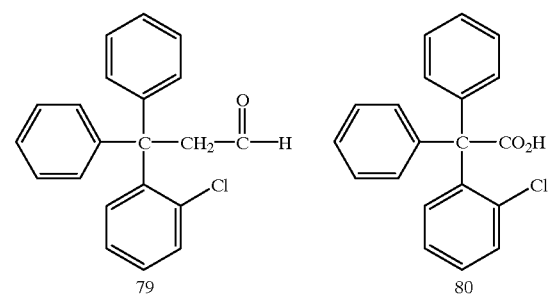
79    80
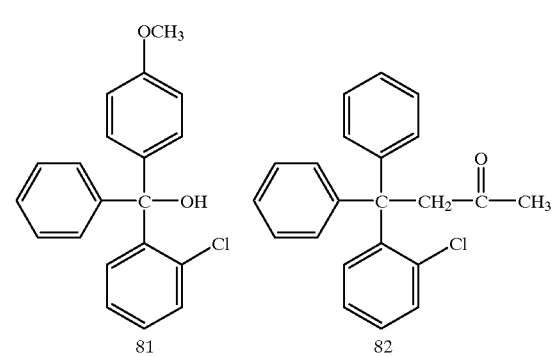
81    82

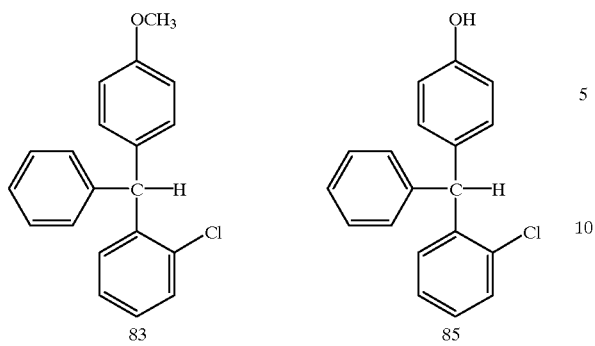
83
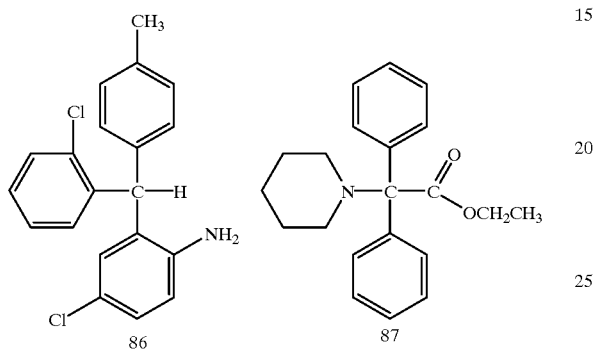
85
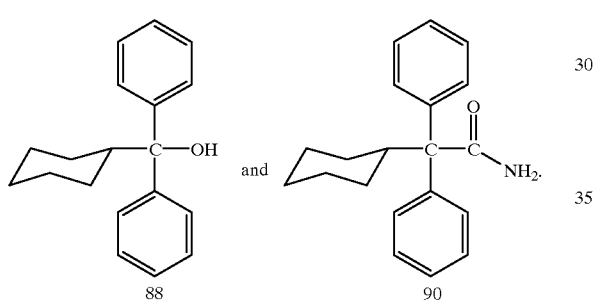
86 87
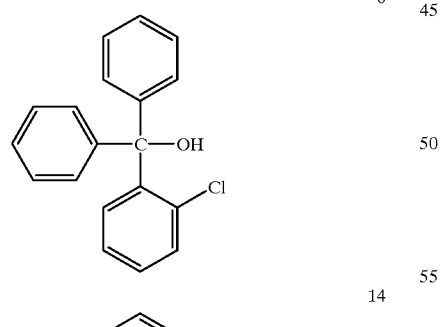
88 and 90
20. The method of claim 19, wherein said compound is selected from the group consisting of
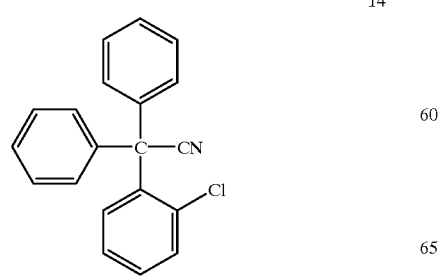
6
14
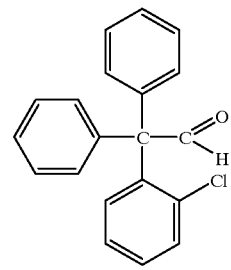
15
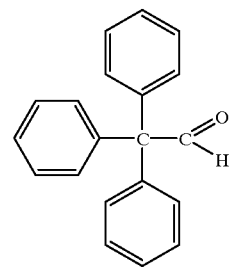
16
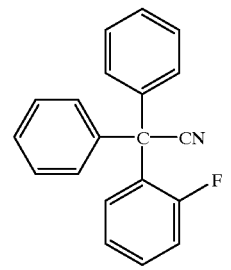
32
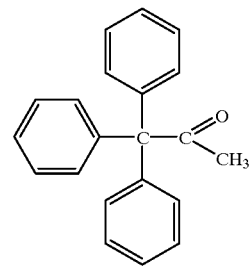
37
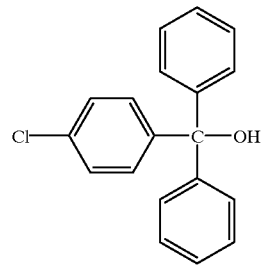
43

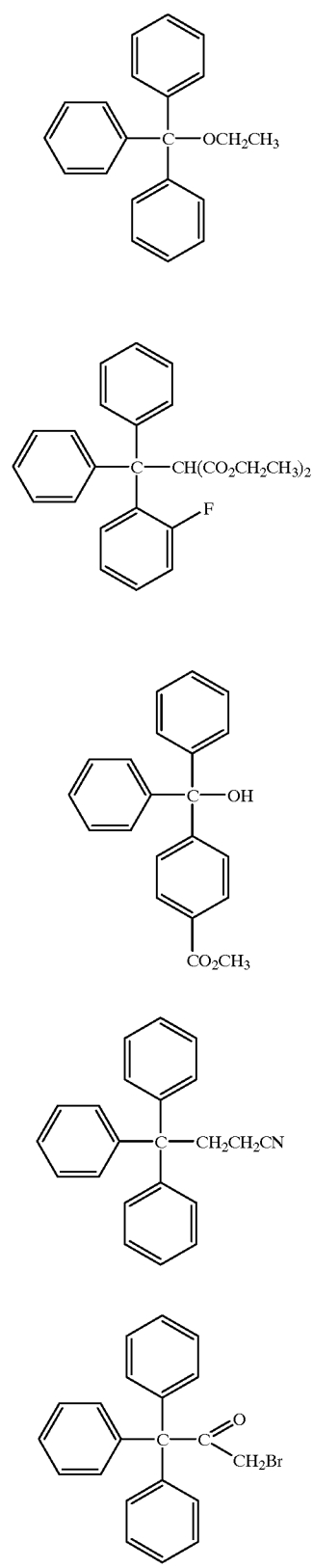
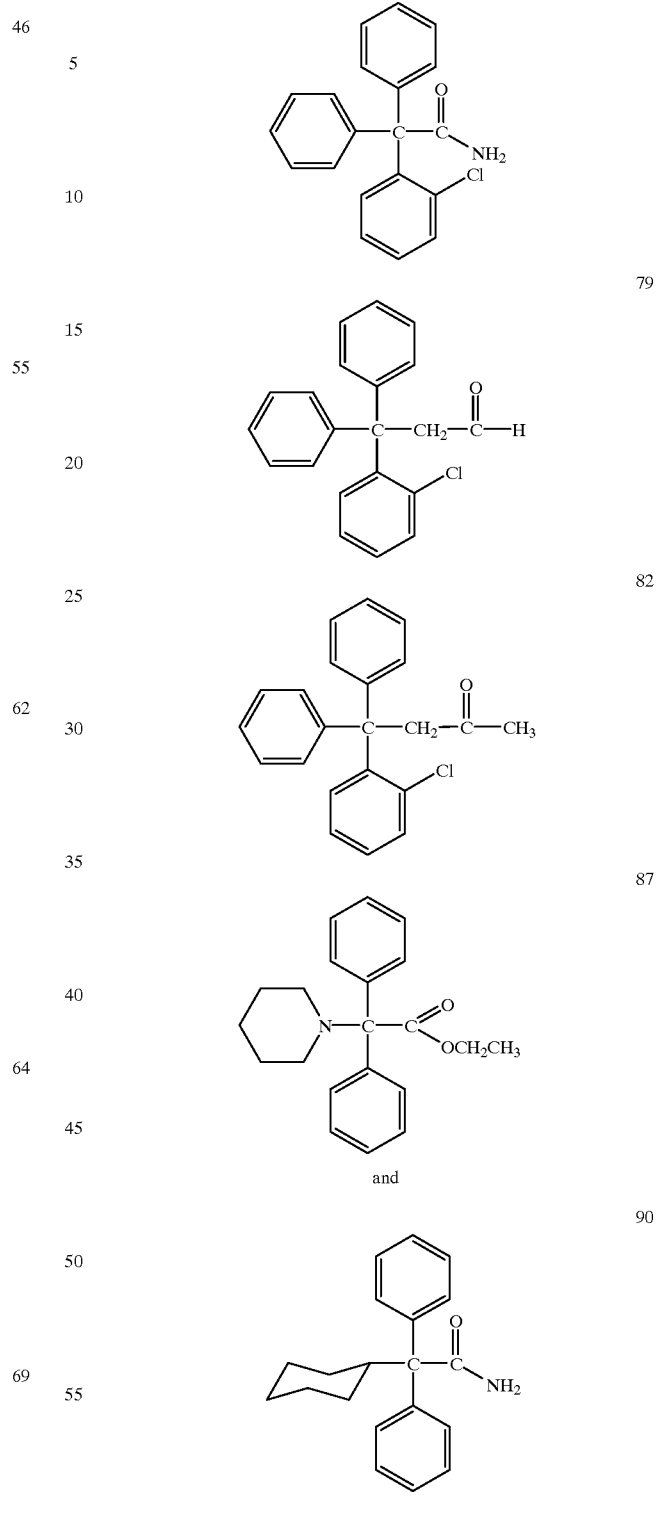
21. A method for reducing sickle erythrocyte dehydration or delaying the occurrence of erythrocyte sickling or deformation, said method comprising the step of contacting a sickle erythrocyte in situ with an effective amount of a compound having the formula:

$$\underset{AR_2}{\overset{AR_1}{\underset{|}{AR_3-Y-(CH_2)_nR_1}}}\overset{X}{|}\quad \text{(I)}$$

or a pharmaceutically acceptable salt or hydrate thereof, wherein:

n is 0, 1, 2, 3 or 4;

X is absent, $(C_1-C_3)$ alkyl, $(C_1-C_3)$ alkenyl, or $(C_1-C_3)$ alkynyl;

Y is C, N, P, Si or Ge;

$R_1$ is absent, -halo, —R, —OR, —SR, —$NR_2$, —$ONR_2$, —$NO_2$, —CN, —C(O)R, —C(S)R, —C(O)OR, C(S)OR, —C(O)SR, —C(S)SR, —C(O)$NR_2$, —C(S)$NR_2$, —C(O)NR(OR), —C(S)NR(OR), C(O)NR(SR), C(S)NR(SR), —CH(CN)$_2$, —CH[C(O)R]$_2$, —CH[C(S)R]$_2$, —CH[C(O)OR]$_2$—CH[C(S)OR]$_2$, —CH[C(O)SR]$_2$, —CH[C(S)SR]$_2$ or aryl;

$Ar_1$ is aryl, substituted aryl, heteroaryl other than imidazole, nitroimidazole and triazole, heteroarylium other than imidazolium, nitroimidazolium and triazolium, $(C_5-C_8)$ cycloalkyl or $(C_5-C_8)$ heterocycloalkyl;

$Ar_2$ is aryl or substituted aryl;

$Ar_3$ is aryl, substituted aryl, biaryl or heteroaryl other than imidazole, nitroimidazole and triazole;

each R is independently selected from the group consisting of —H, $(C_1-C_6)$ alkyl. substituted $(C_1-C_6)$ alkyl, $(C_1-C_6)$ alkenyl, substituted $(C_1-C_6)$ alkenyl, $(C_1-C_6)$ alkynyl, substituted $(C_1-C_6)$ alkynyl and $(C_1-C_6)$ alkoxy;

the aryl substituents are each independently selected from the group consisting of -halo, trihalomethyl, —R, —R', —OR', —SR', NR'$_2$, —NO$_2$, —CN, —C(O)R', —C(S)R', —C(O)OR', —C(S)OR', —C(O)SR'and —C(S)SR';

the alkyl, alkenyl and alkynyl substituents are each independently selected from the group consisting of —halo, —R', —OR', —SR', NR'$_2$, —NO$_2$, —CN, —C(O)R', —C(S)R', —C(O)OR', —C(S)OR', —C(O)SR', —C(S)SR', aryl, γ-butyrolactonyl, pyrrolidinyl and succinic anhydridyl; and each R' is independently selected from the group consisting of —H, $(C_1-C_6)$ alkyl, $(C_1-C_6)$ alkenyl and $(C_1-C_6)$ alkynyl.

22. The method of claim 21, wherein said compound is selected from the group consisting of -continued
15
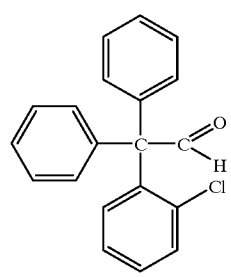
16
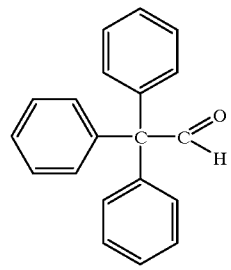
17
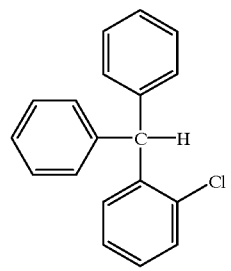
18
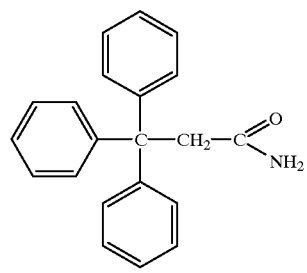
20
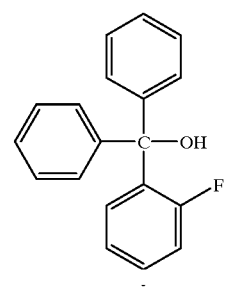
-continued
21
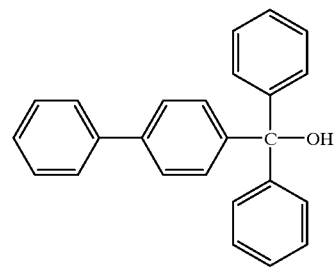
22
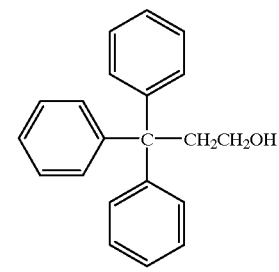
23
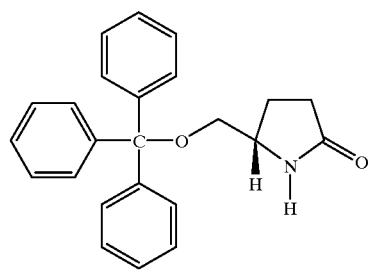
24
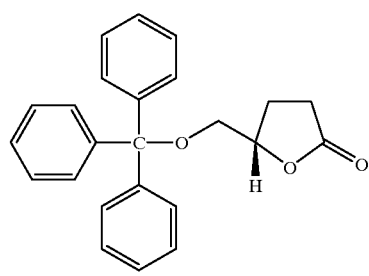
27
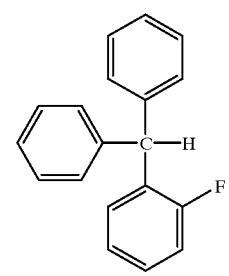

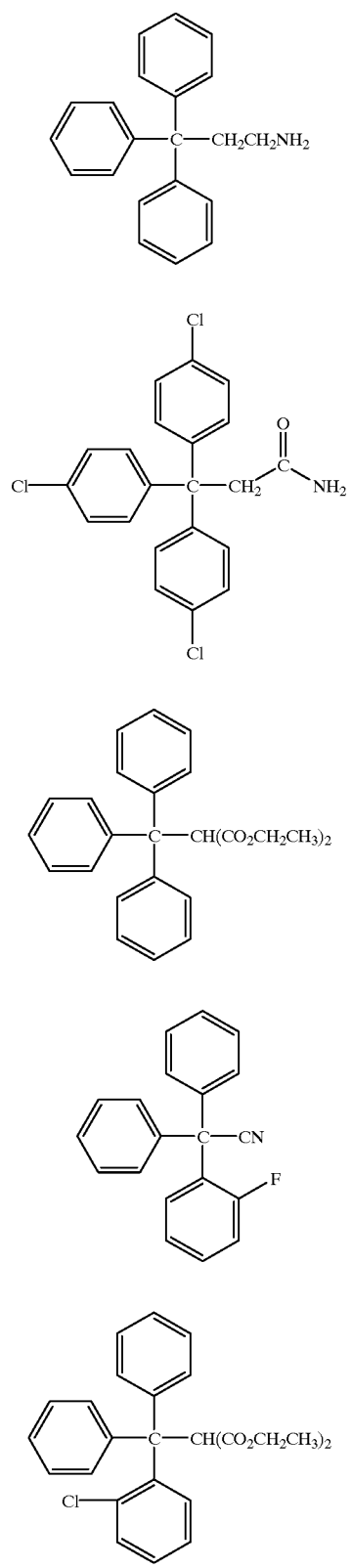
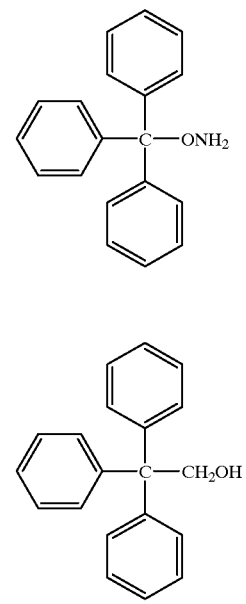

43
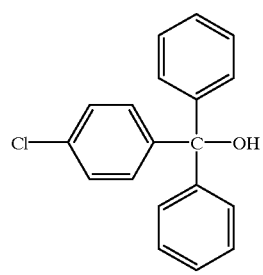
44
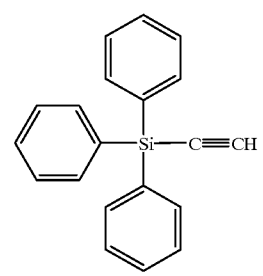
45
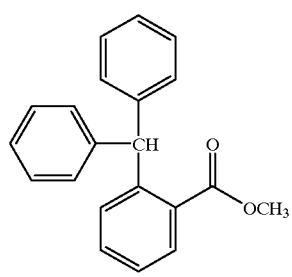
46
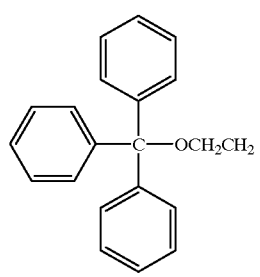
47
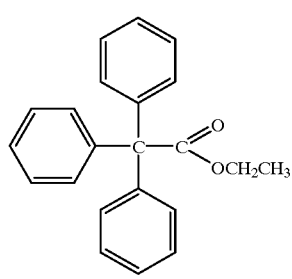
49
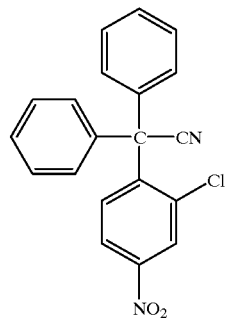
50
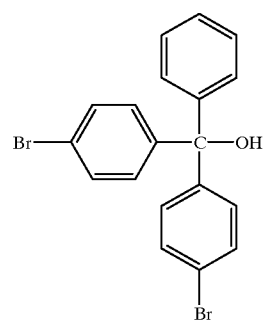
51
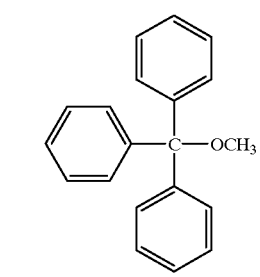
52
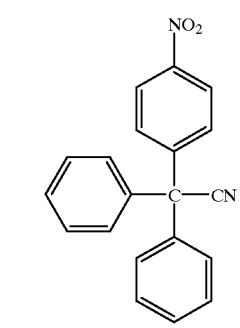
53
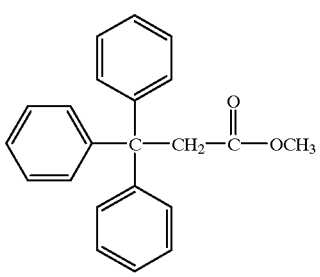

135
-continued
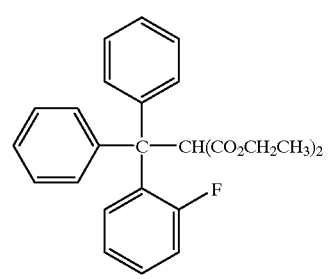
55
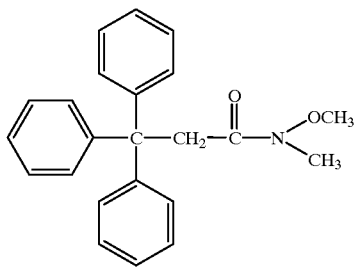
56
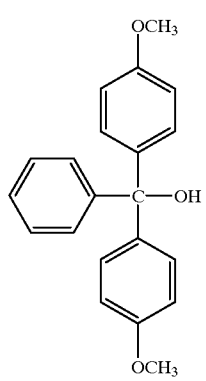
58
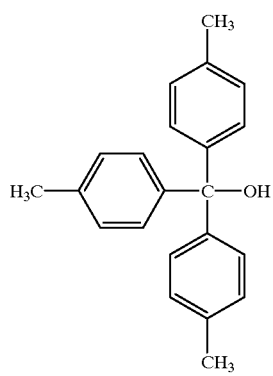
59
136
-continued
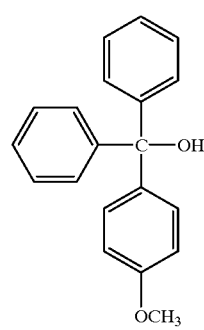
60
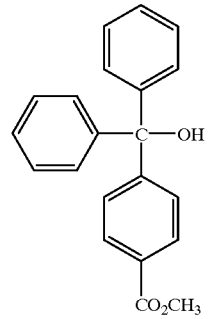
62
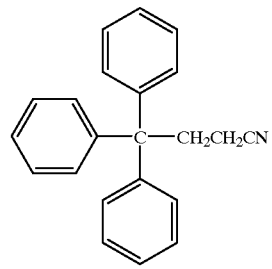
64
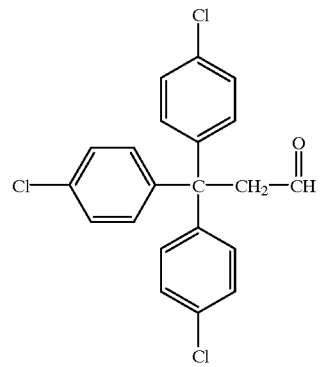
65

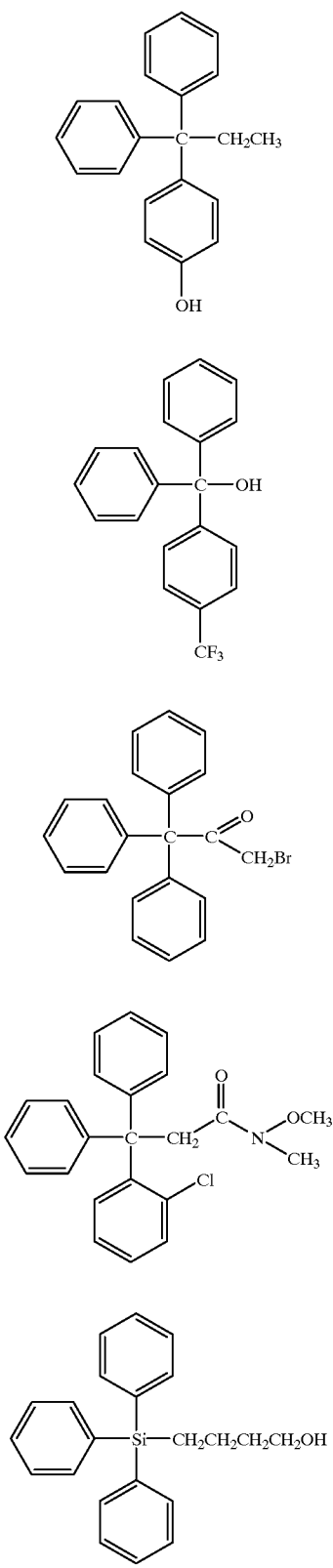
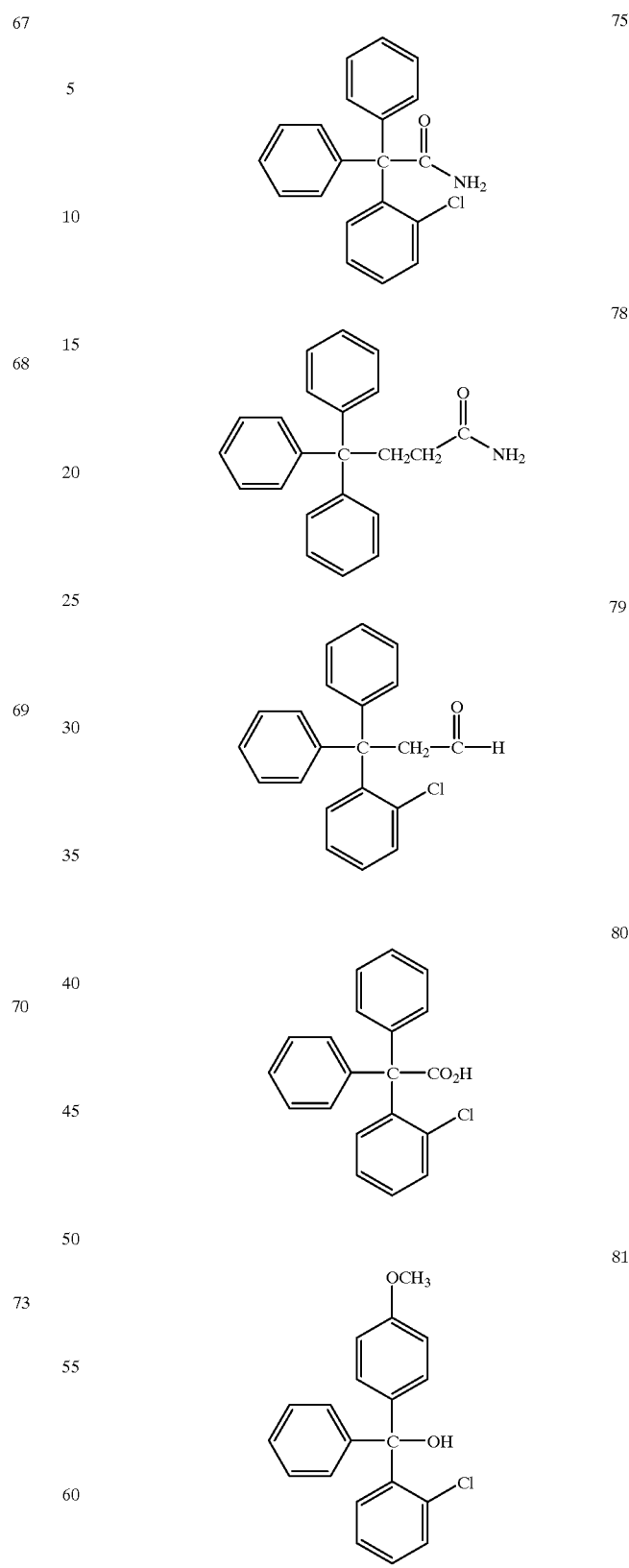

82
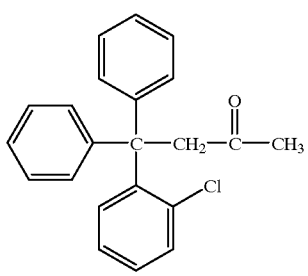
83
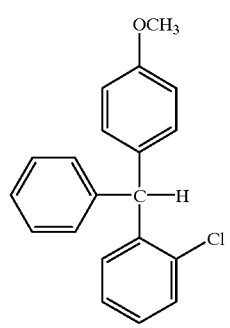
85
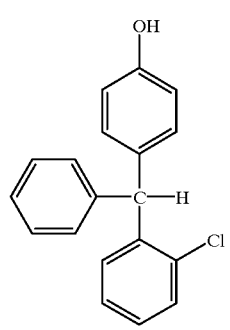
86
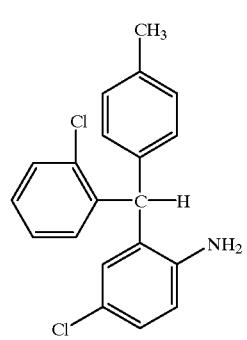
87
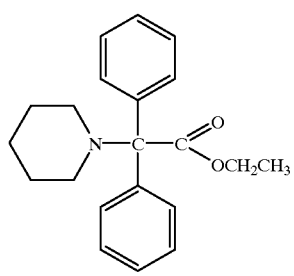
88
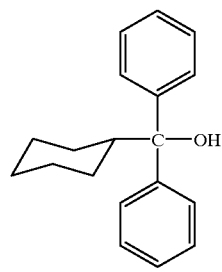
and
90
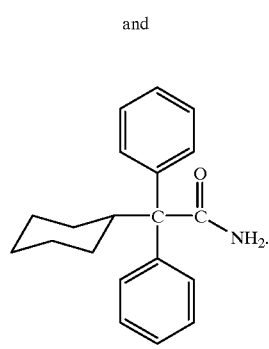
23. The method of claim 22, wherein said compound is selected from the group consisting of
6
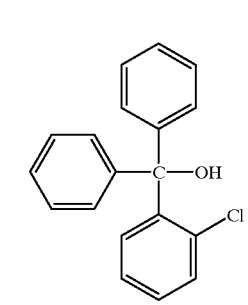
14
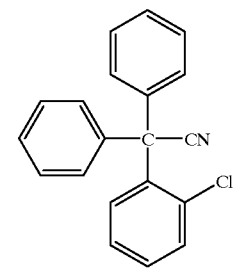
15
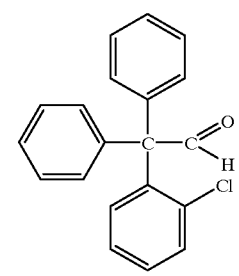

-continued
16
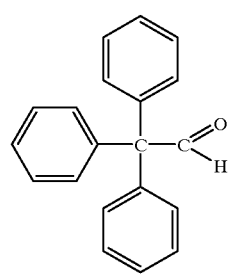
32
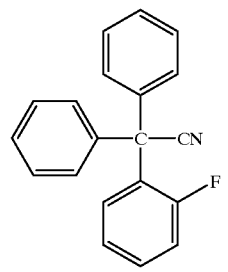
37
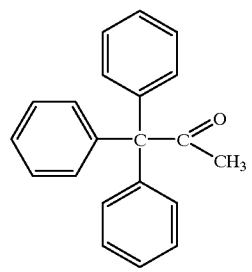
43
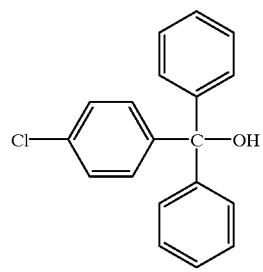
46
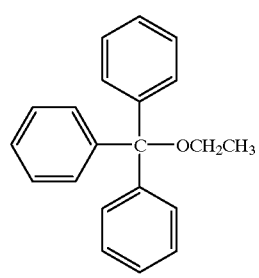
-continued
55
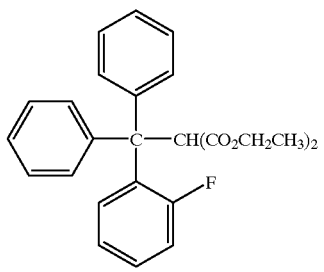
62
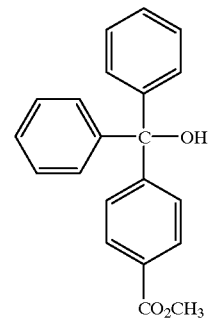
64
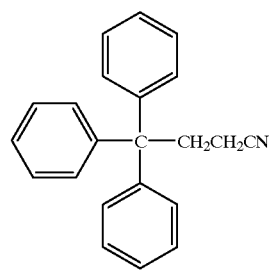
69
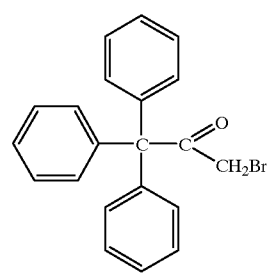
75
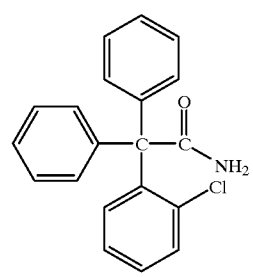

-continued

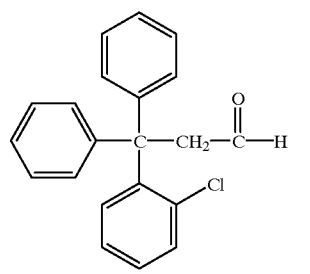
79

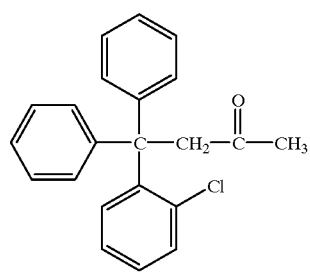
82

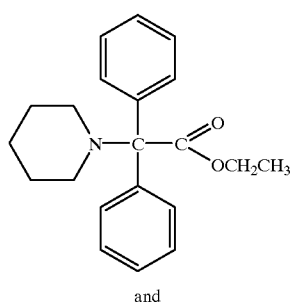
87 and

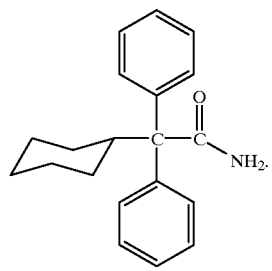
90

24. The method of claim 21, wherein said administration is selected from the group consisting of oral, parenteral, intravenous, subcutaneous, transdermal and transmucosal for a living human.

25. A method of treating or preventing sickle cell disease, said method comprising the step of administering to a subject suffering from sickle cell disease a therapeutically effective amount of a compound having the formula:

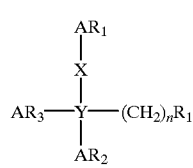
(I)

or a pharmaceutically acceptable salt or hydrate thereof, wherein:

n is 0, 1, 2, 3 or 4;

X is absent $(C_1-C_3)$ alkyl, $(C_1-C_3)$ alkenyl or $(C_1-C_3)$ alkynyl;

Y is C, N, P, Si or Ge;

$R_1$ is absent, -halo, —R, —OR, —SR, —NR$_2$, —ONR$_2$, —NO$_2$, —CN, —C(O)R, —C(S)R, —C(O)OR, —C(S)OR, —C(O)SR, —C(S)SR, —C(O)NR$_2$, —C(S)NR$_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$ or aryl;

Ar$_1$ is aryl, substituted aryl, heteroaryl other than imidazole, nitroimidazole and triazole, heteroarylium other than imidazolium, nitroimidazolium and triazolium, $(C_5-C_8)$ cycloalkyl or $(C_5-C_8)$ heterocycloalkyl;

Ar$_2$ is aryl or substituted aryl;

Ar$_3$ is aryl, substituted aryl, biaryl or heteroaryl other than imidazole, nitroimidazole and triazole;

each R is independently selected from the group consisting of —H, $(C_1-C_6)$ alkyl, substituted $(C_1-C_6)$ alkyl, $(C_1-C_6)$ alkenyl, substituted $(C_1-C_6)$ alkenyl, $(C_1-C_6)$ alkynyl, substituted $(C_1-C_6)$ alkynyl and $(C_1-C_6)$ alkoxy;

the aryl substituents are each independently selected from the group consisting of -halo, trihalomethyl, —R, —R', —OR', —SR', NR'$_2$, —NO$_2$, —CN, —C(O)R', —C(S)R', —C(O)OR', —C(S)OR', —C(O)SR' and —C(S)SR';

the alkyl, alkenyl and alkynyl substituents are each independently selected from the group consisting of -halo, —R', —OR', —SR', NR'$_2$, —NO$_2$, —CN, —C(O)R', —C(S)R', —C(O)OR', —C(S)OR', —C(O)SR', —C(S)SR', aryl, γ-butyrolactonyl, pyrrolidinyl and succinic anhydridyl; and each R' is independently selected from the group consisting of —H, $(C_1-C_6)$ alkyl, $(C_1-C_6)$ alkenyl and $(C_1-C_6)$ alkynyl.

26. The method of claim 25, wherein said compound is selected from the group consisting of

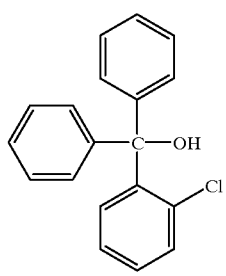
6

7
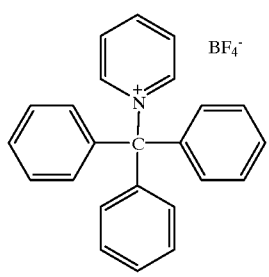
10
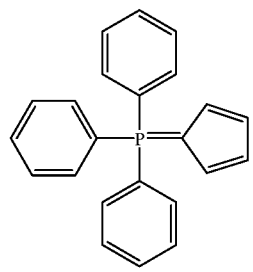
12
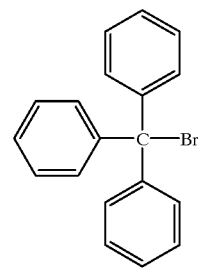
13
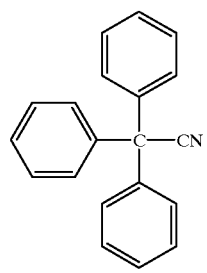
14
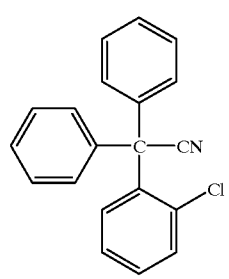
15
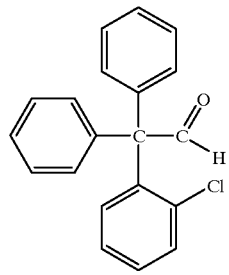
16
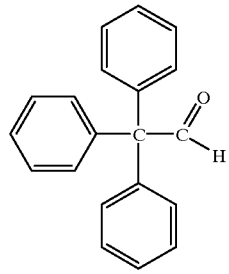
17
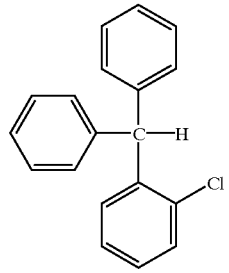
18
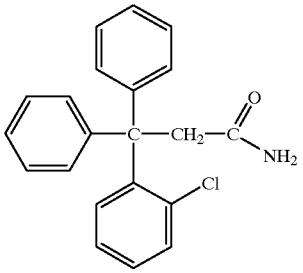
20
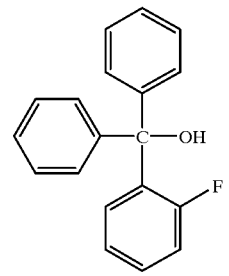

21 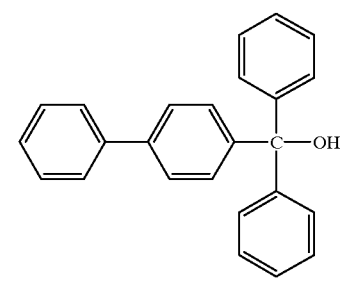
22 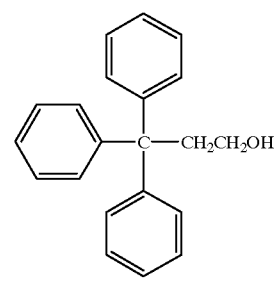
23 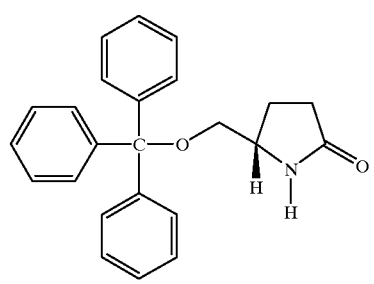
24 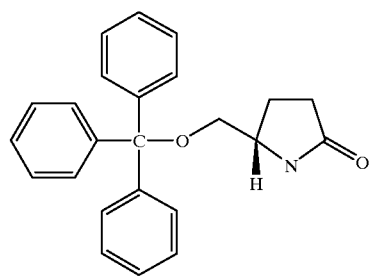
27 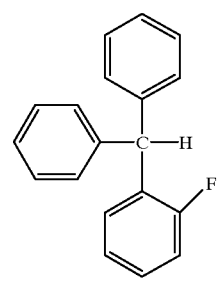
29 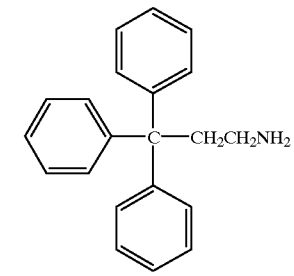
30 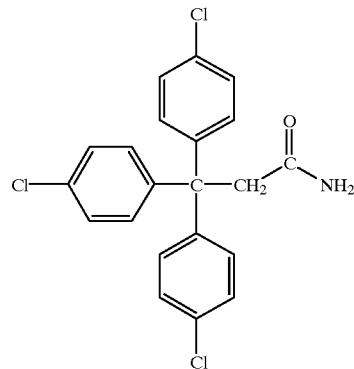
31 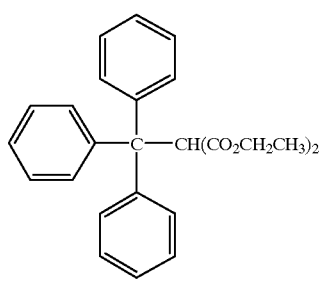
32 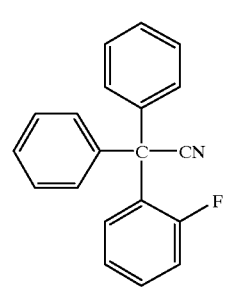
33 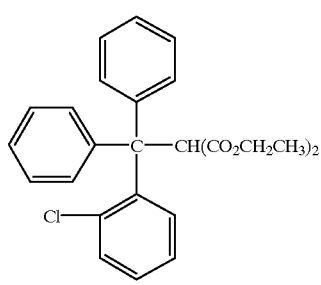

34
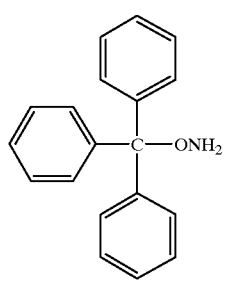
35
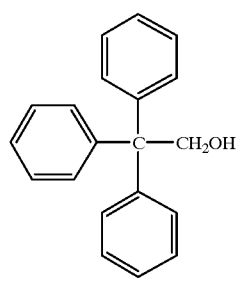
37
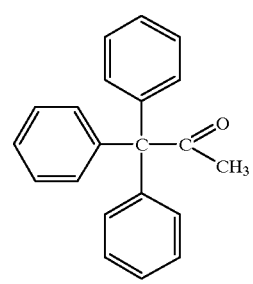
38
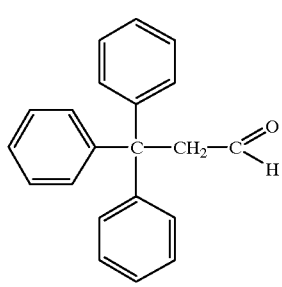
42
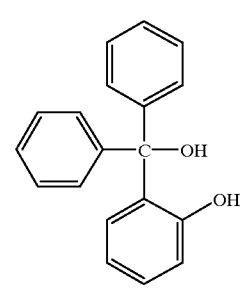
43
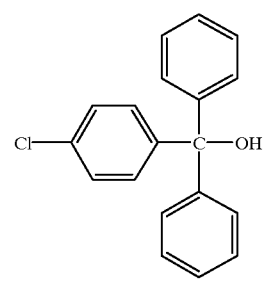
44
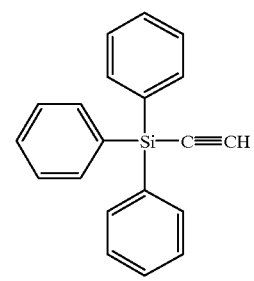
45
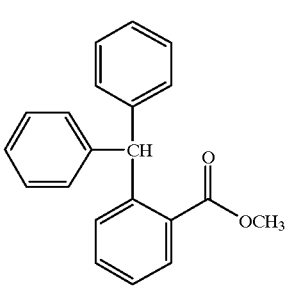
46
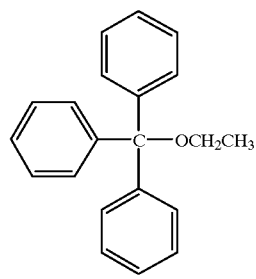
47
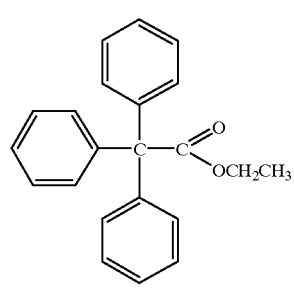

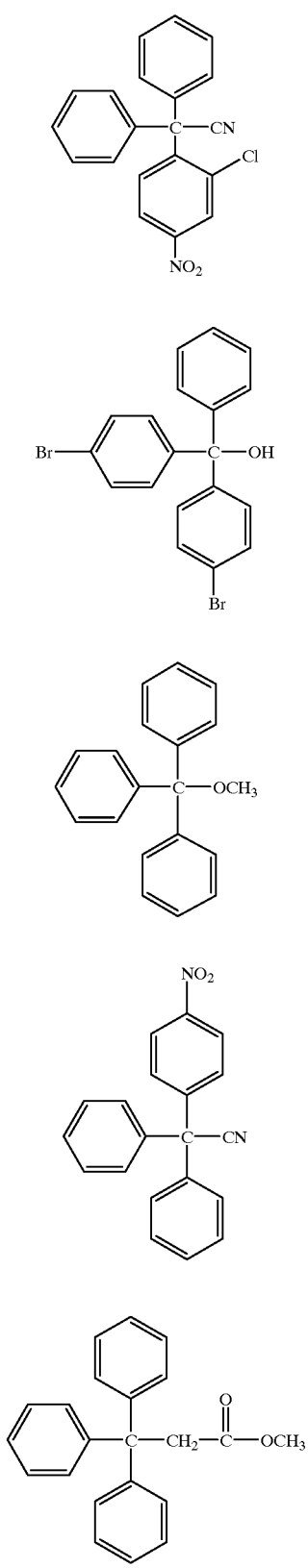
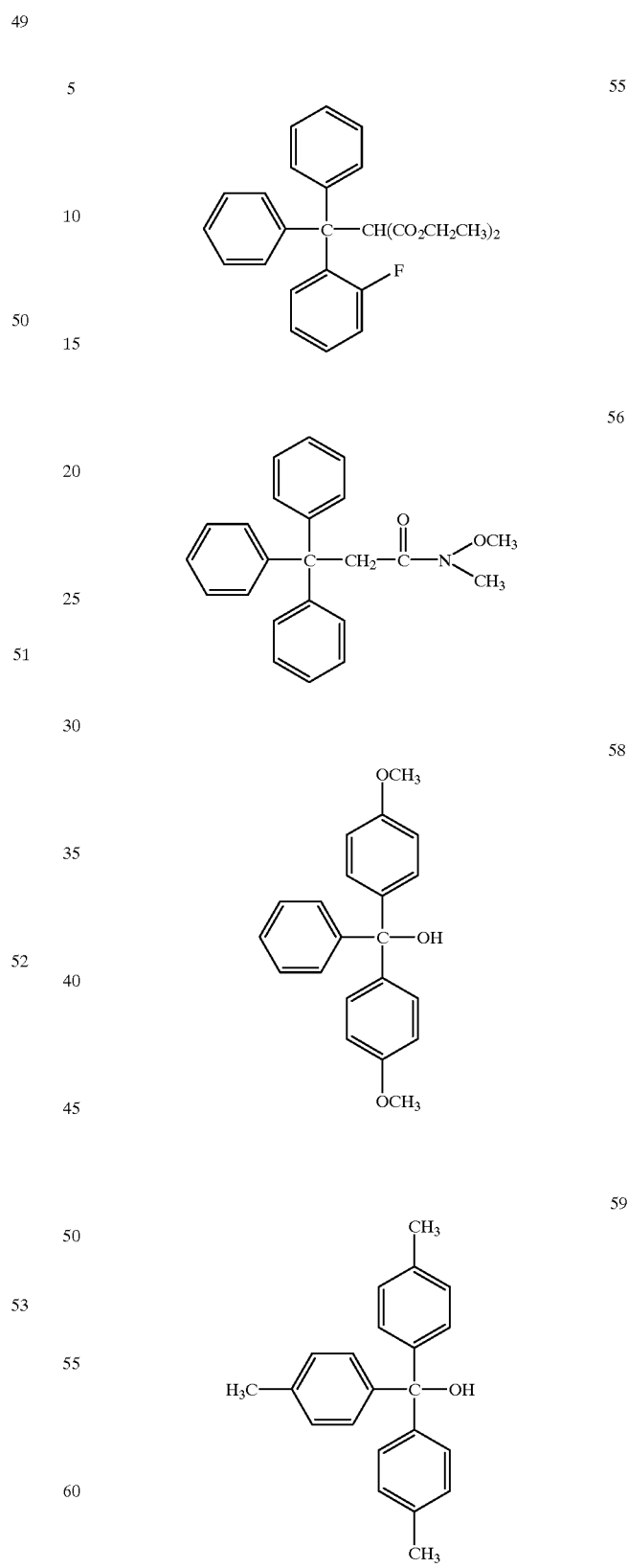

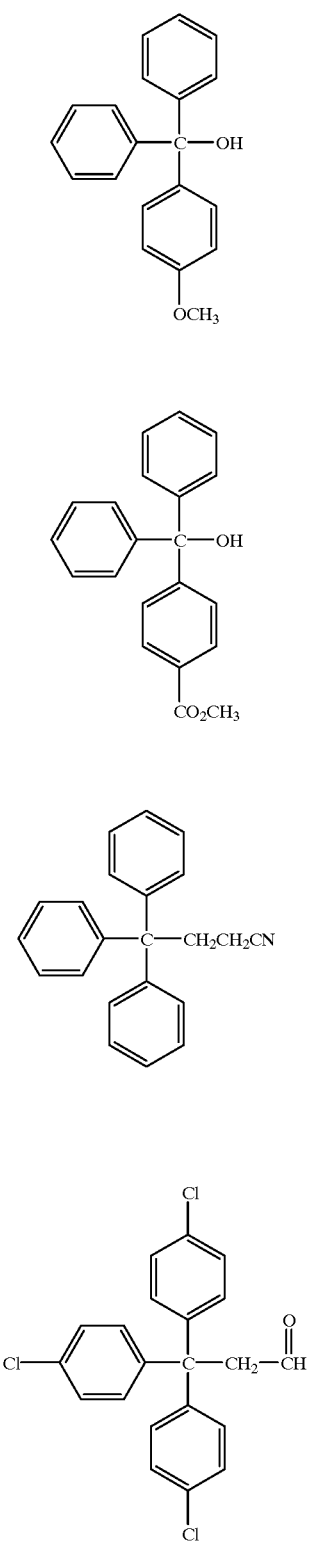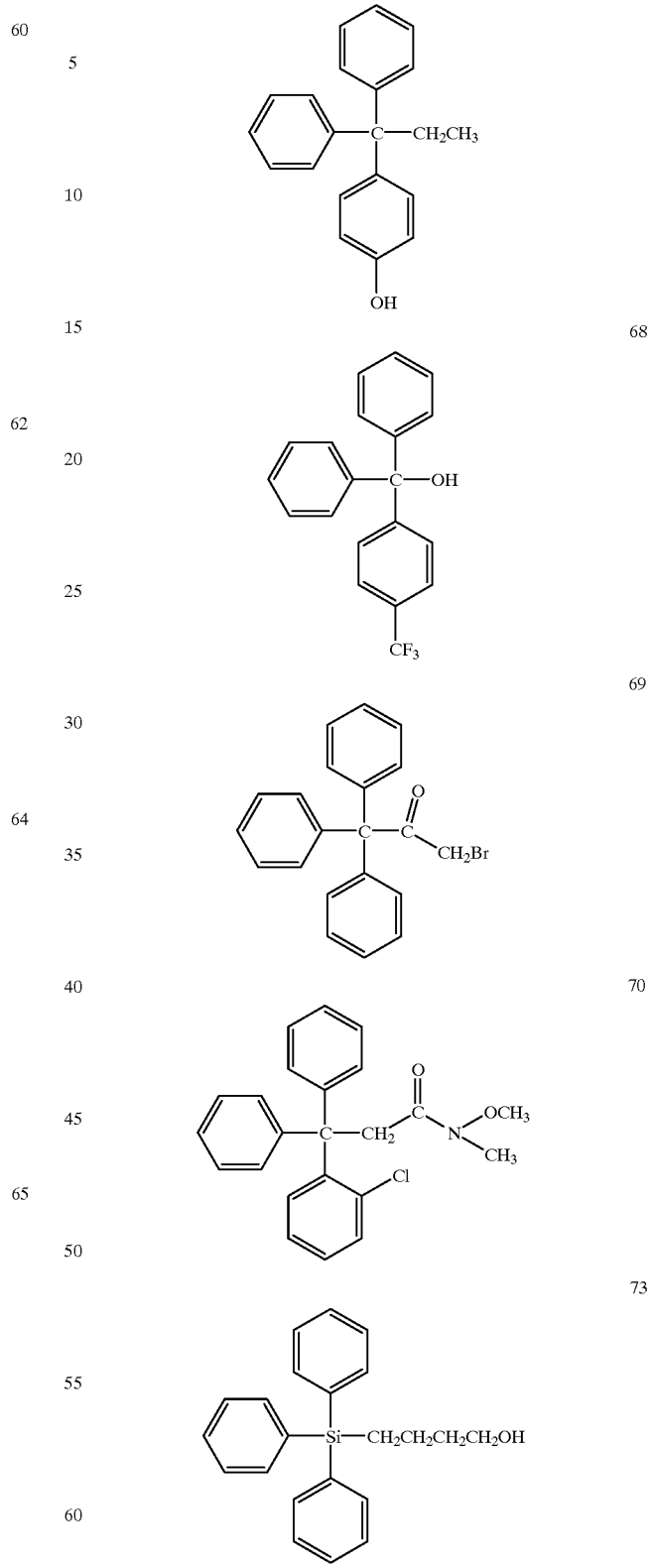

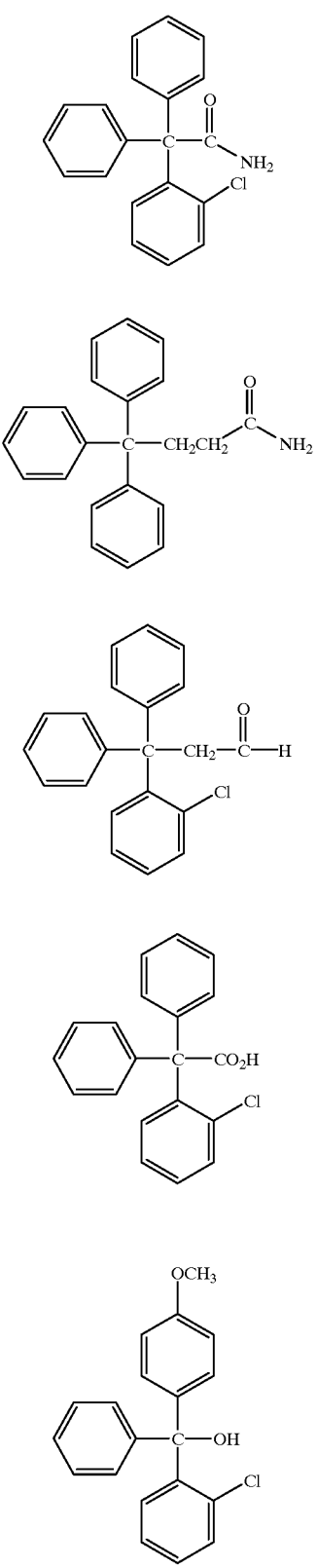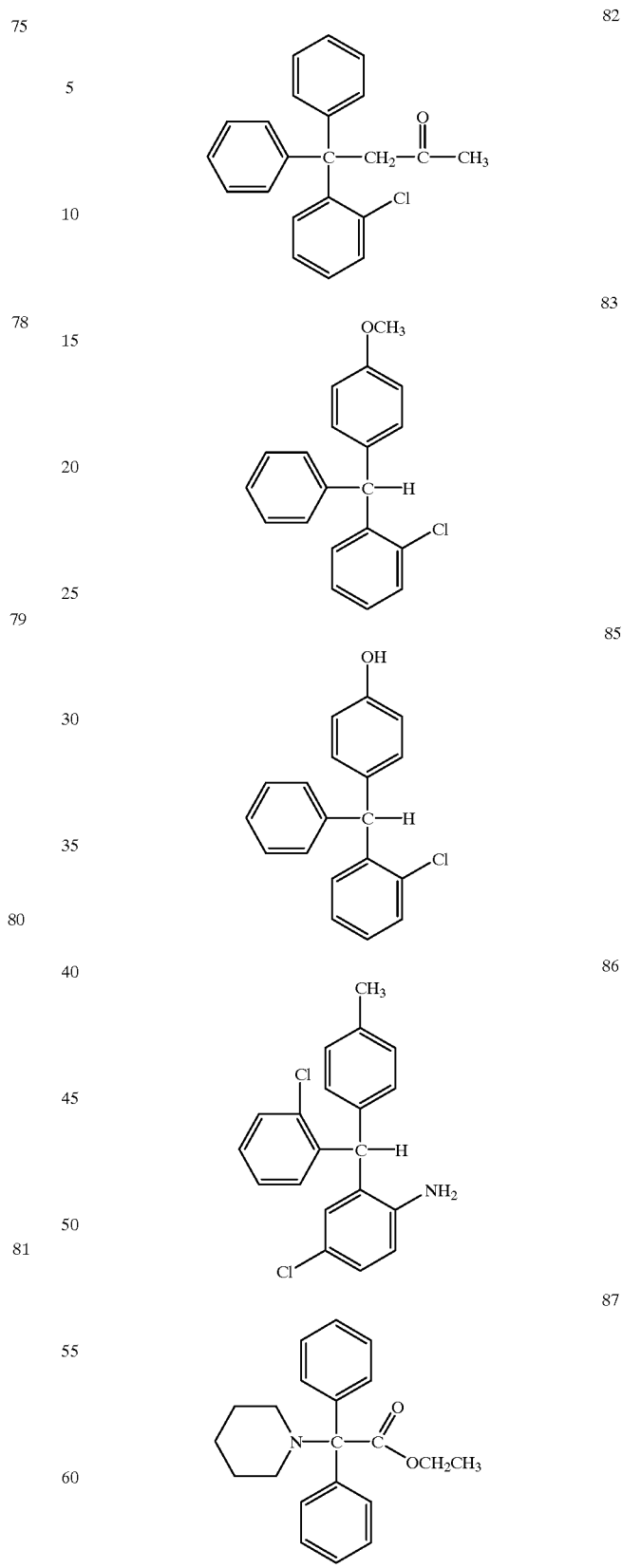

-continued
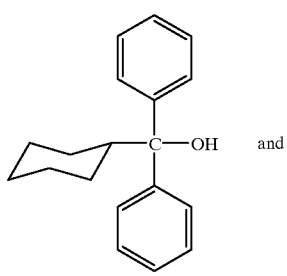
88
and
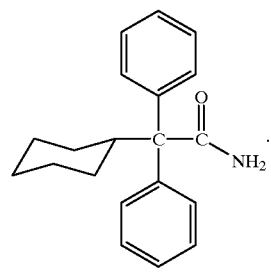
90
27. The method of claim 26, wherein said compound is selected from the group consisting of
6
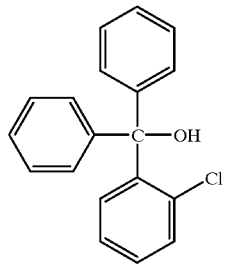
14
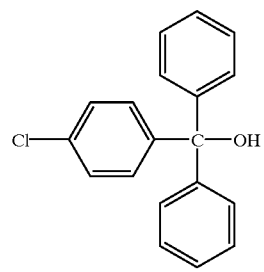
15
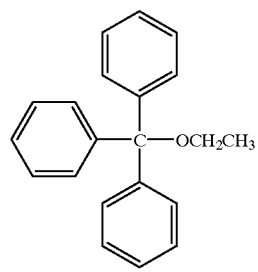
-continued
16
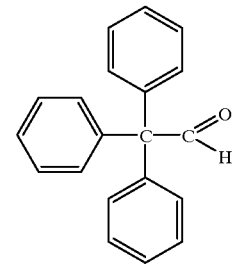
32
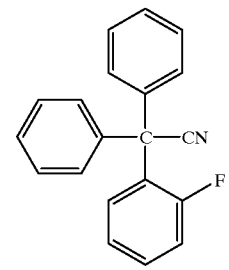
37
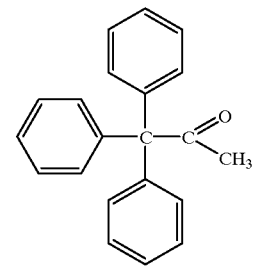
43
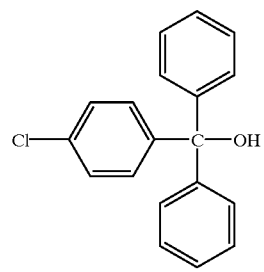
46
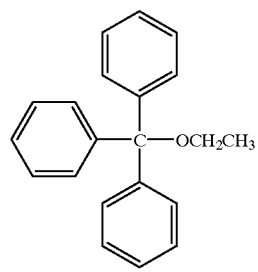

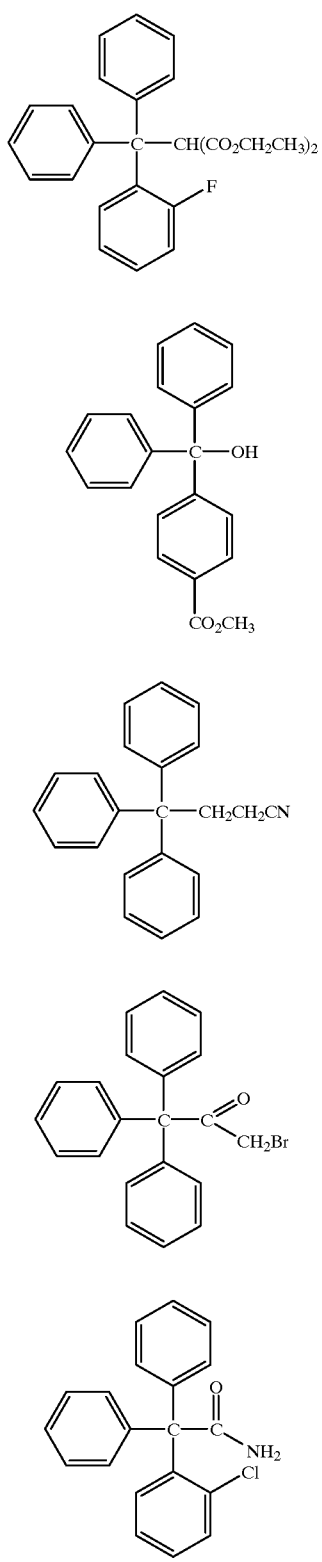

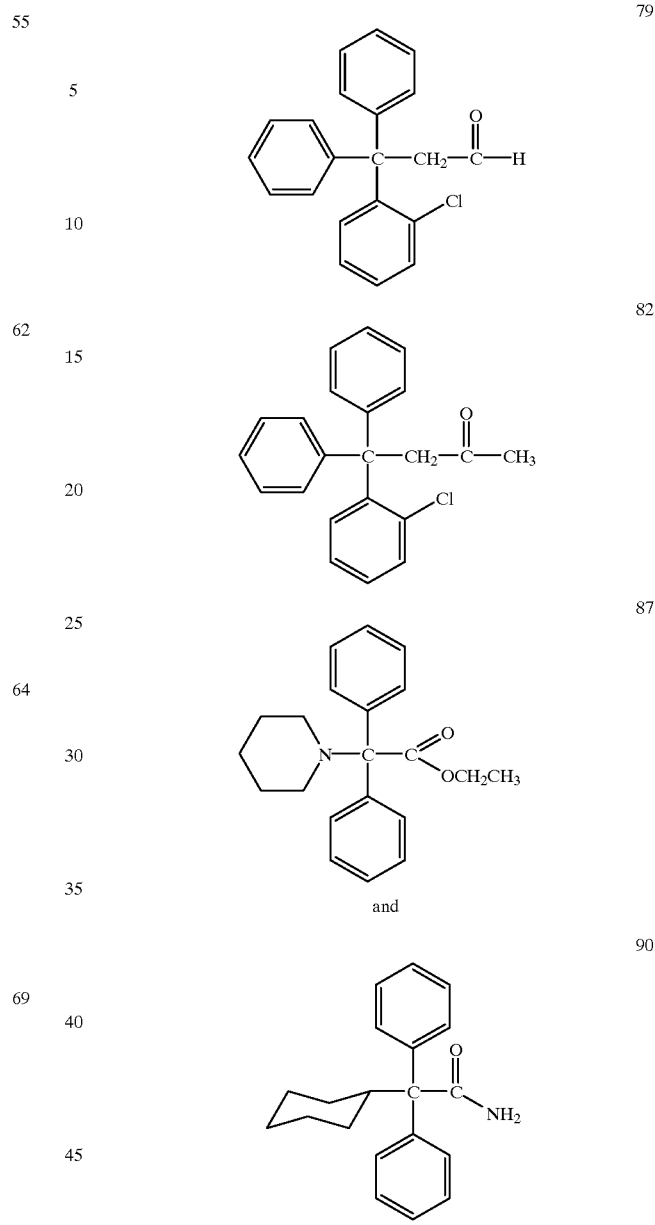

28. The method of claim 25, wherein said patient is suffering from acute sickle crisis.

29. The method of claim 25, wherein said administration is parenteral.

30. The method of claim 24, wherein said patient is suffering from chronic sickle cell episodes.

31. The method of claim 30, wherein said administration is per oral.

32. A method of inhibiting mammalian cell proliferation, said method comprising the step of contacting a mammalian cell in situ with an effective amount of a compound having the formula:

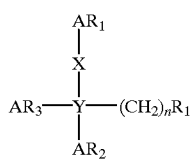
(I)

or pharmaceutically acceptable salts of hydrates thereof, wherein:

n is 0, 1, 2, 3 or 4;

X is absent, $(C_1-C_3)$ alkyl, $(C_1-C_3)$ alkenyl or $(C_1-C_3)$ alkynyl;

Y is C, N, P, Si or Ge;

$R_1$ is absent, -halo, —R, —OR, —SR, —$NR_2$, —$ONR_2$, —$NO_2$, —CN, —C(O)R, —C(S)R, —C(O)OR, —C(S)OR, —C(O)SR, —C(S)SR, —C(O)$NR_2$, —C(S)$NR_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O)OR]$_2$, —CH[C(O)SR]$_2$, —CH[C(O)SR]$_2$, —CH[C(S)SR]$_2$ or aryl;

$Ar_1$ is aryl, substituted aryl, heteroaryl other than imidazole, nitroimidazole and triazole, heteroarylium other than imidazolium, nitroimidazolium and triazolium, $(C_5-C_8)$ cycloalkyl or $(C_5-C_8)$ heterocycloalkyl;

$Ar_2$ is aryl or substituted aryl;

$Ar_3$ is aryl, substituted aryl, biaryl or heteroaryl other than imidazole, nitroimidazole and triazole;

each R is independently selected from the group consisting of —H, $(C_1-C_6)$ alkyl, substituted $(C_1-C_6)$ alkyl, $(C_1-C_6)$ alkenyl, substituted $(C_1-C_6)$ alkenyl, $(C_1-C_6)$ alkynyl, substituted $(C_1-C_6)$ alkynyl and $(C_1-C_6)$ alkoxy;

the aryl substituents are each independently selected from the group consisting of -halo, trihalomethyl, —R, —R', —OR', —SR', NR'$_2$, —NO$_2$, —CN, —C(O)R', —C(S)R', —C(O)OR', —C(S)OR', —C(O)SR' and —C(S)SR';

the alkyl, alkenyl and alkynyl substituents are each independently selected from the group consisting of -halo, —R', —OR', —SR', NR'$_2$, —NO$_2$, —CN, —C(O)R', —C(S)R', —C(O)OR', —C(S)OR', —C(O)SR', —C(S)SR', aryl, γ-butyrolactonyl, pyrrolidinyl and succinic anhydridyl; and each R' is independently selected from the group consisting of —H, $(C_1-C_6)$ alkyl, $(C_1-C_6)$ alkenyl and $(C_1-C_6)$ alkynyl.

33. The method of claim 32, wherein said compound is selected from the group consisting of compounds

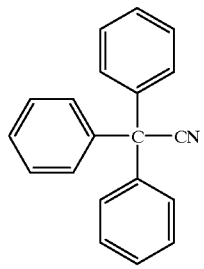

13

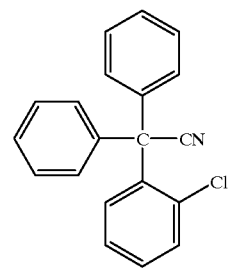

14

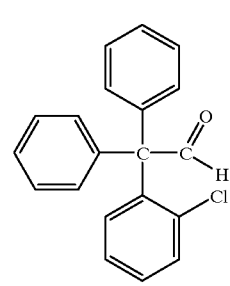

15

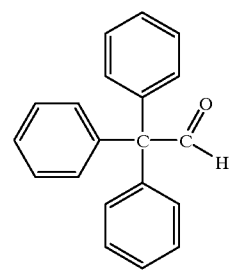

16

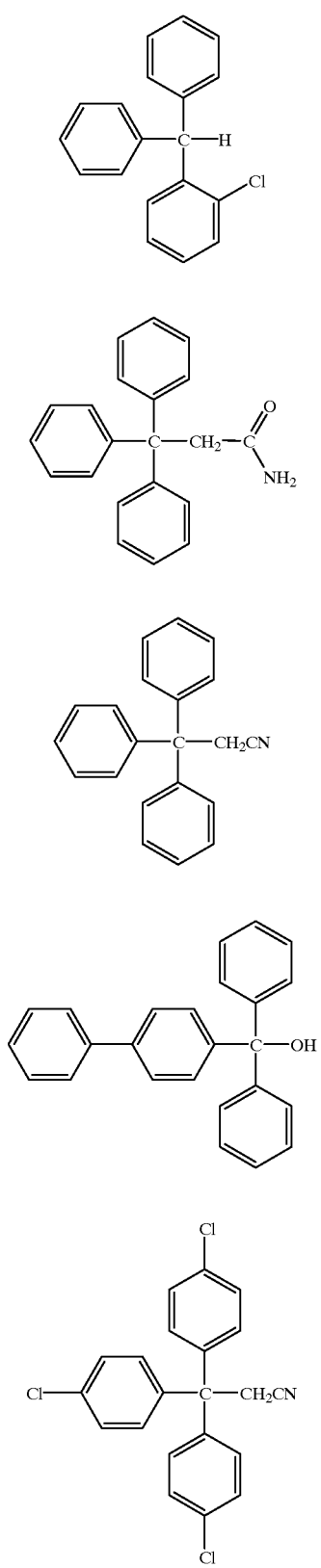
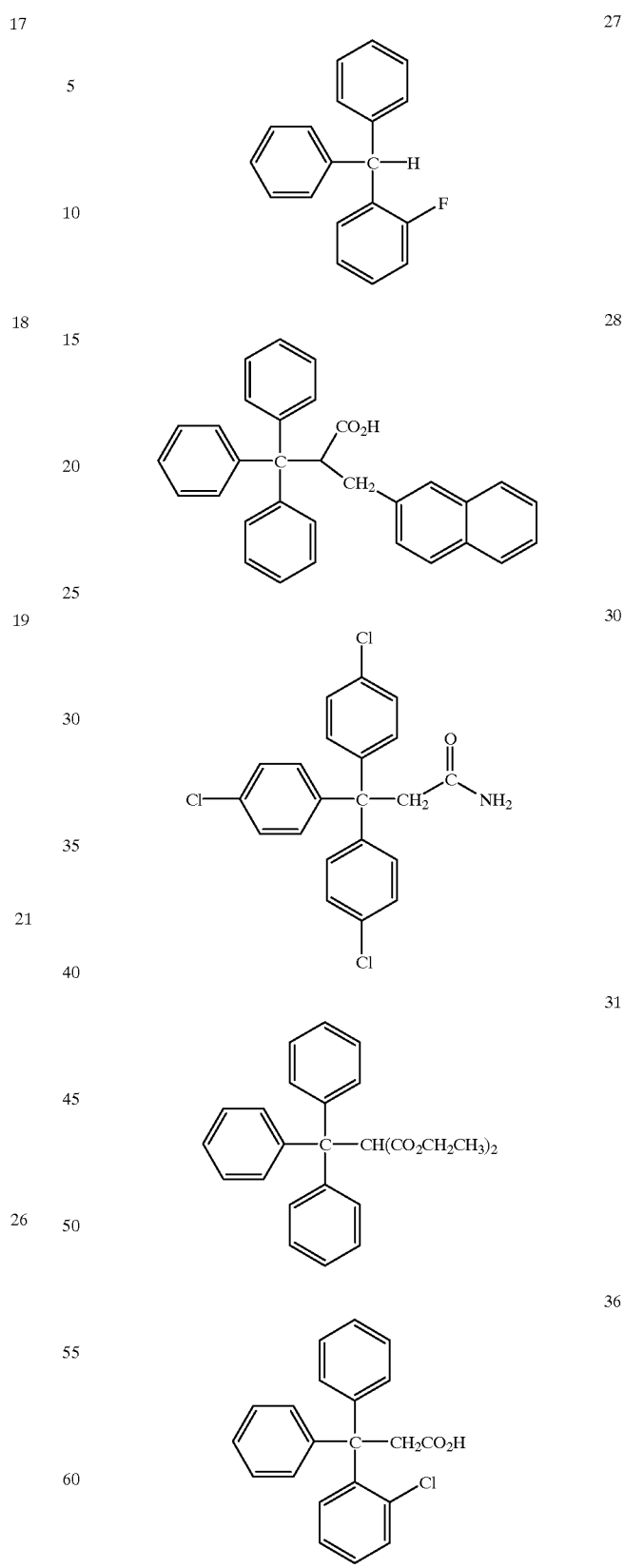

38
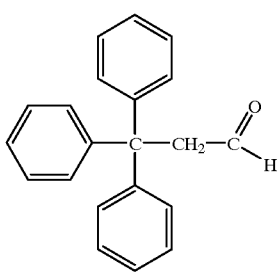
40
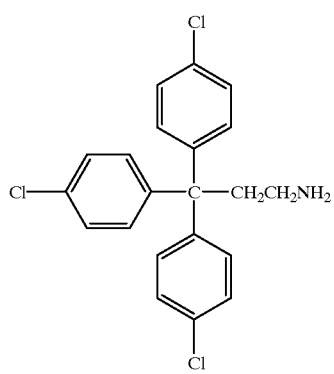
41
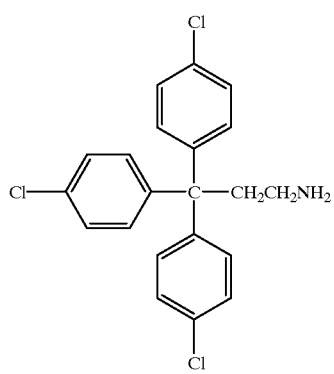
42
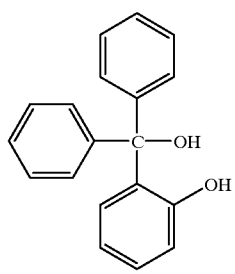
43
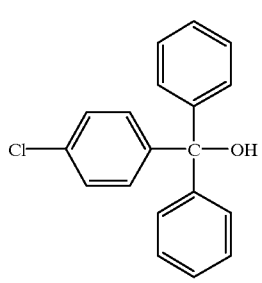
45
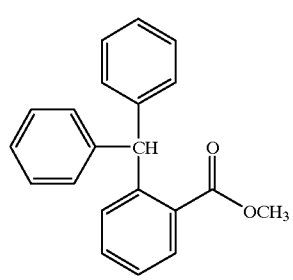
46
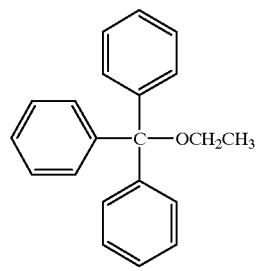
47
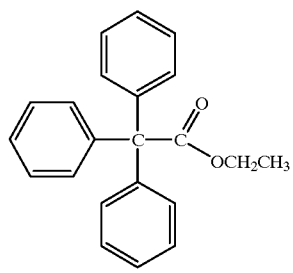
48
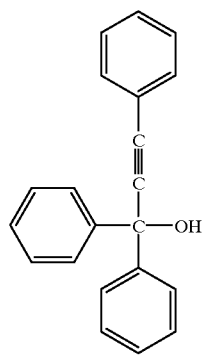
49
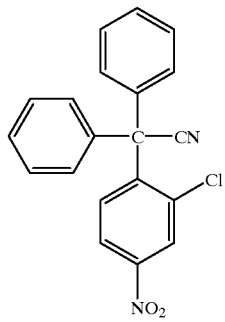

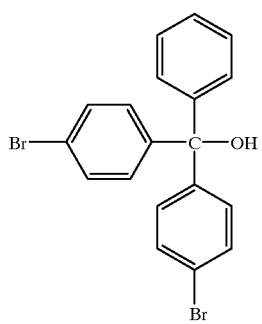
50
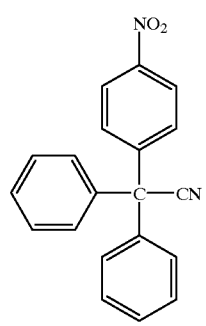
52
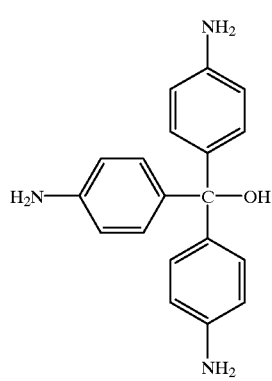
54
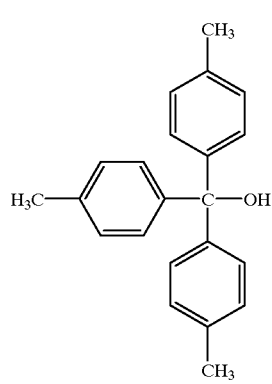
59
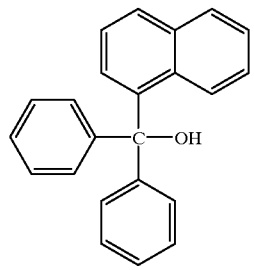
61
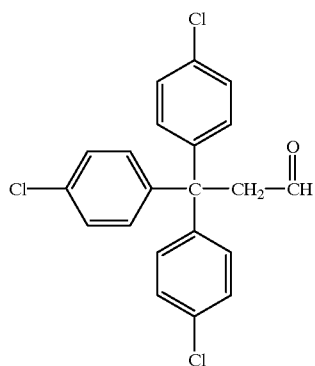
65
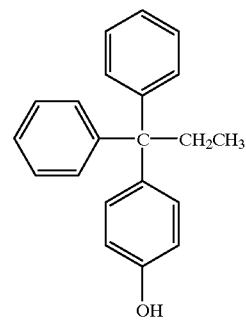
67
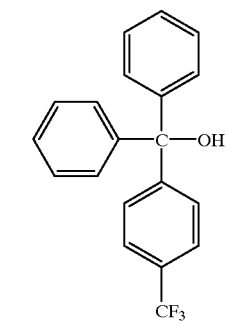
68
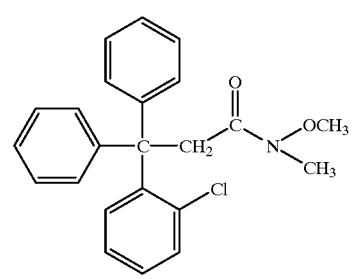
70

71 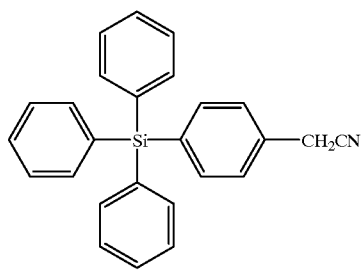
72 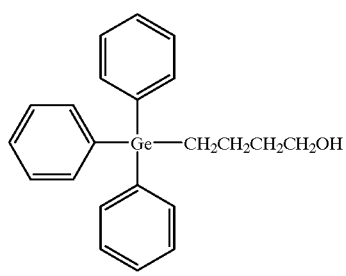
73 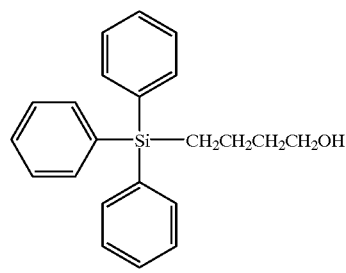
79 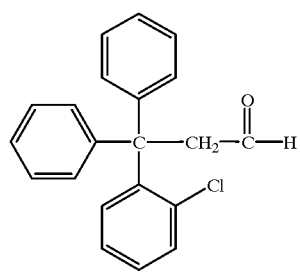
82 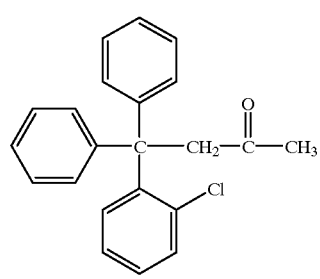
83 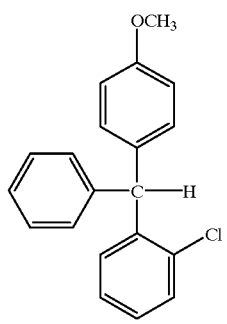
84 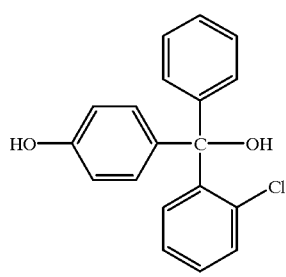
85 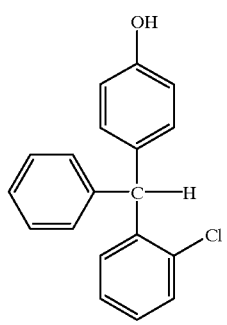
86 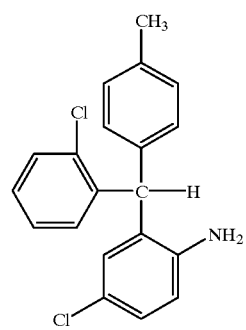
89 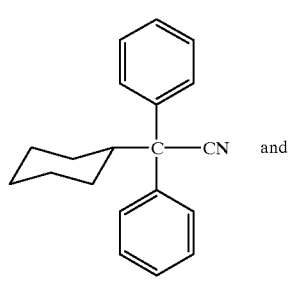 and

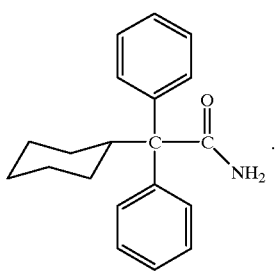
90
34. The method of claim 33, wherein said compound is selected from the group consisting of compounds
16
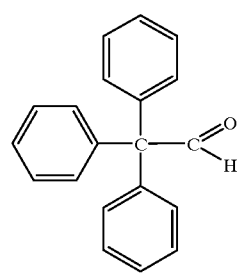
28
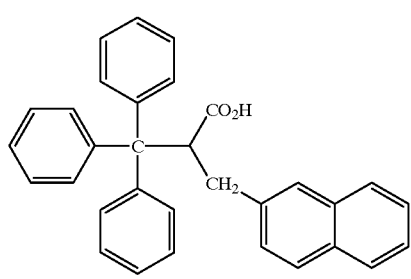
30
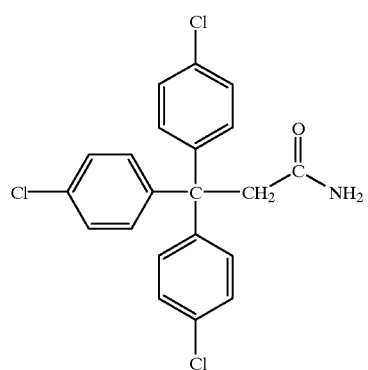
36
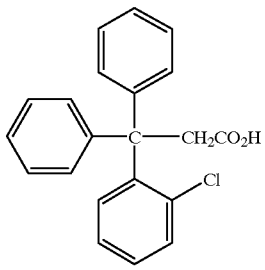
43
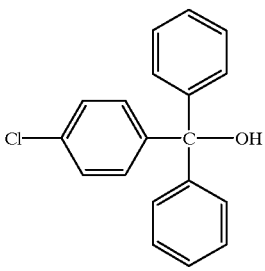
45
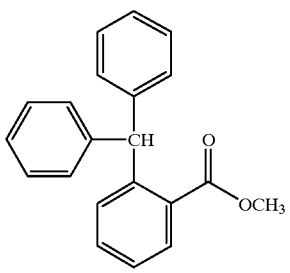
47
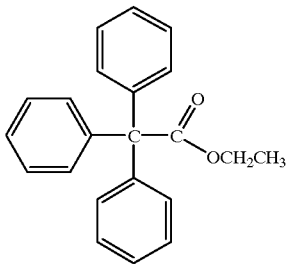
48
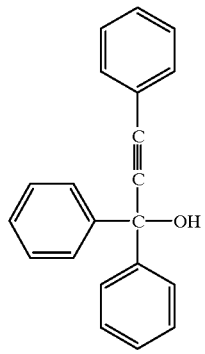

-continued

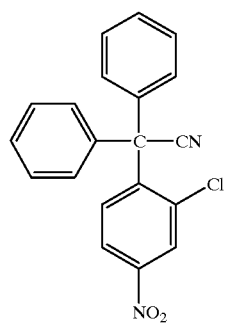
49

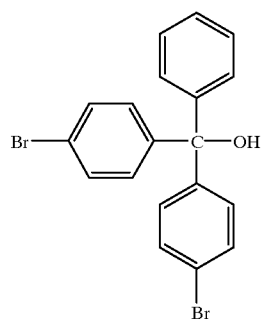
50

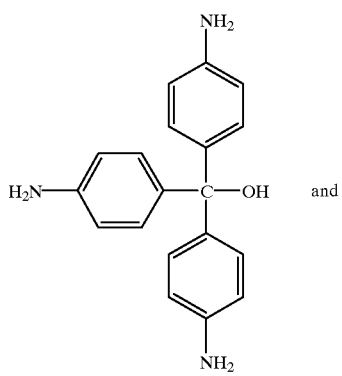
54
and

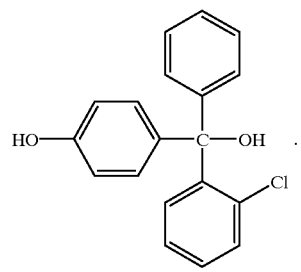
84

35. The method of claim 32, wherein said mammalian cell is an endothelial cell, a fibrotic cell or a vascular smooth muscle cell.

36. A method of treating a disorder characterized by abnormal cell proliferation, said method comprising the step of administering to a subject a therapeutically effective amount of a composition having the formula:

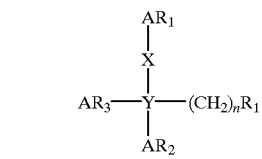
(I)

or pharmaceutically acceptable salts of hydrates thereof, wherein:

n is 0, 1, 2, 3 or 4;

X is absent ($C_1$–$C_3$) alkyl, ($C_1$–$C_3$) alkenyl or ($C_1$–$C_3$) alkynyl;

Y is C, N, P, Si or Ge;

$R_1$ is absent, -halo, —R, —OR, —SR, —$NR_2$, —$ONR_2$, —$NO_2$, —CN, —C(O)R, —C(S)R, —C(O)OR, —C(S)OR, —C(O)SR, —C(S)SR, —C(O)$NR_2$, C(S)$NR_2$, —C(O)NR(OR), —C(S)NR(OR), —C(O)NR(SR), C(S)NR(SR), —CH$(CN)_2$, —CH$[C(O)R]_2$, —CH$[C(S)R]_2$, —CH$[C(O)OR]_2$, —CH$[C(O)SR]_2$, —CH$[C(O)SR]_2$, —CH$[C(S)SR]_2$ or aryl;

$Ar_1$ is aryl, substituted aryl, heteroaryl other than imidazole, nitroimidazole and triazole, heteroarylium other than imidazolium, nitroimidazolium and triazolium, ($C_5$–$C_8$) cycloalkyl or ($C_5$–$C_8$) heterocycloalkyl;

$Ar_2$ is aryl or substituted aryl;

$Ar_3$ is aryl, substituted aryl, biaryl or heteroaryl other than imidazole, nitroimidazole and triazole;

each R is independently selected from the group consisting of —H, ($C_1$–$C_6$) alkyl, substituted ($C_1$–$C_6$) alkyl, ($C_1$–$C_6$) alkenyl, substituted ($C_1$–$C_6$) alkenyl, ($C_1$–$C_6$) alkynyl, substituted ($C_1$–$C_6$) alkynyl and ($C_1$–$C_6$) alkoxy;

the aryl substituents are each independently selected from the group consisting of -halo, trihalomethyl, —R, —R', —OR', —SR', NR'$_2$, —$NO_2$, —CN, —C(O)R', —C(S)R', —C(O)OR', —C(S)OR', —C(O)SR' and —C(S)SR';

the alkyl, alkenyl and alkynyl substituents are each independently selected from the group consisting of -halo, —R', —OR', —SR', NR'$_2$, —$NO_2$, —CN, —C(O)R', —C(S)R', —C(O)OR', —C(S)OR', —C(O)SR', —C(S)SR', aryl, γbutyrolactonyl, pyrrolidinyl and succinic anhydridyl; and each R' is independently selected from the group consisting of —H, ($C_1$–$C_6$) alkyl, ($C_1$–$C_6$) alkenyl and ($C_1$–$C_6$) alkynyl.

37. The method of claim 36, wherein said compound is selected from the group consisting of compounds
13
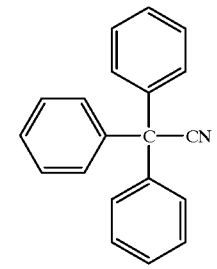
14
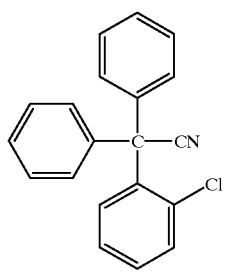
15
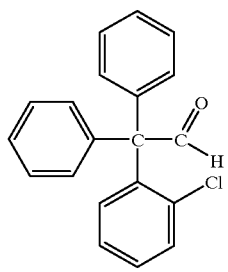
16
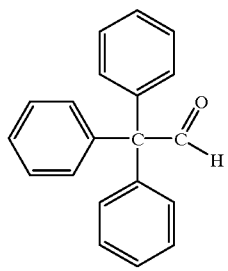
17
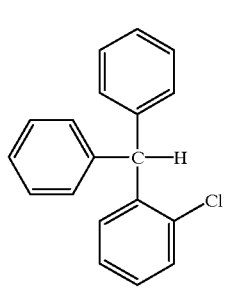
-continued
18
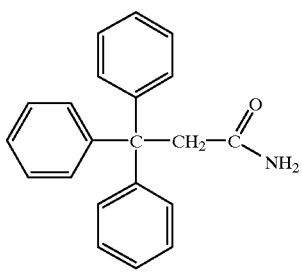
19
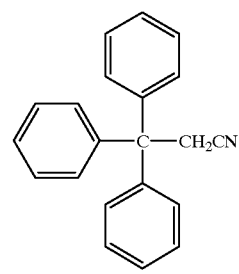
21
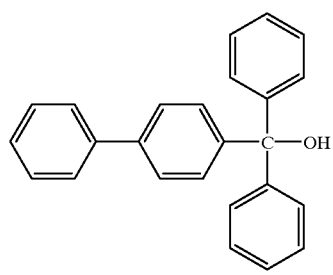
26
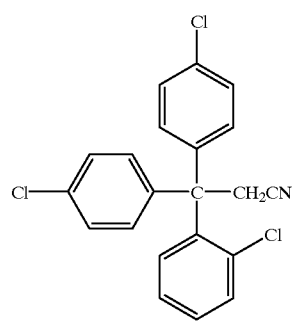
27
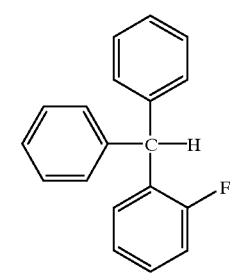

28
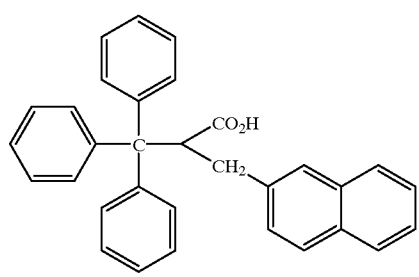
30
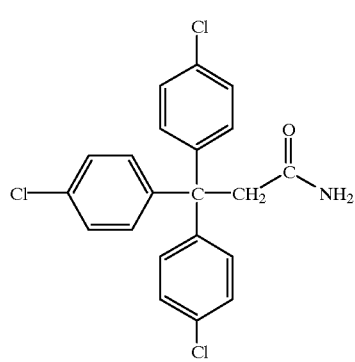
31
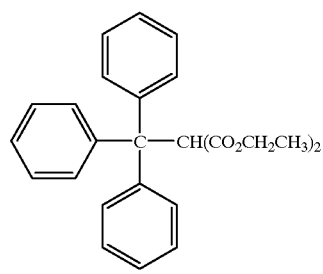
36
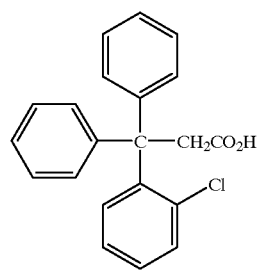
38
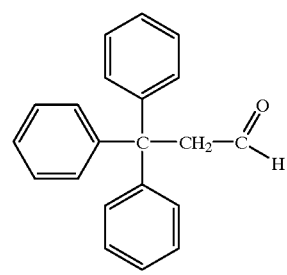
40
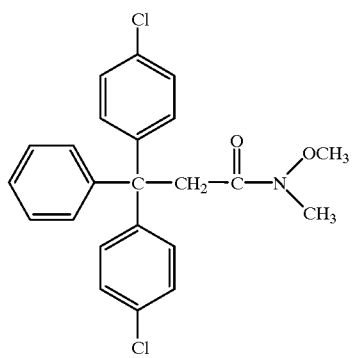
41
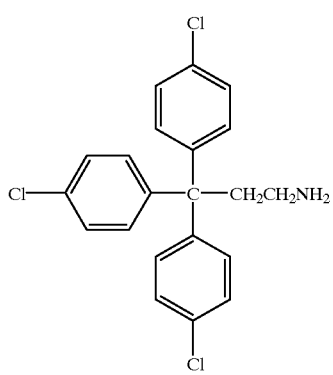
42
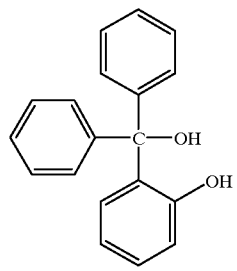
43
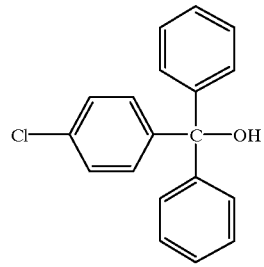
45
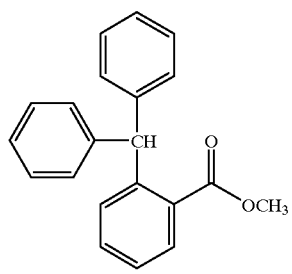

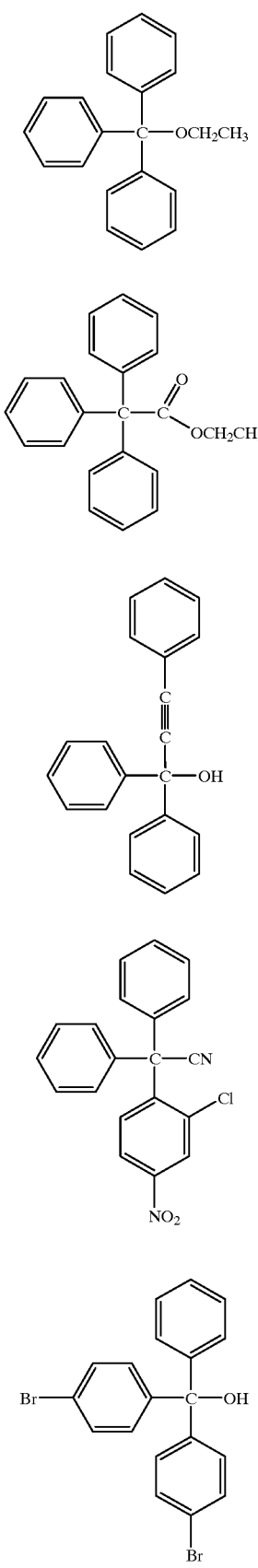
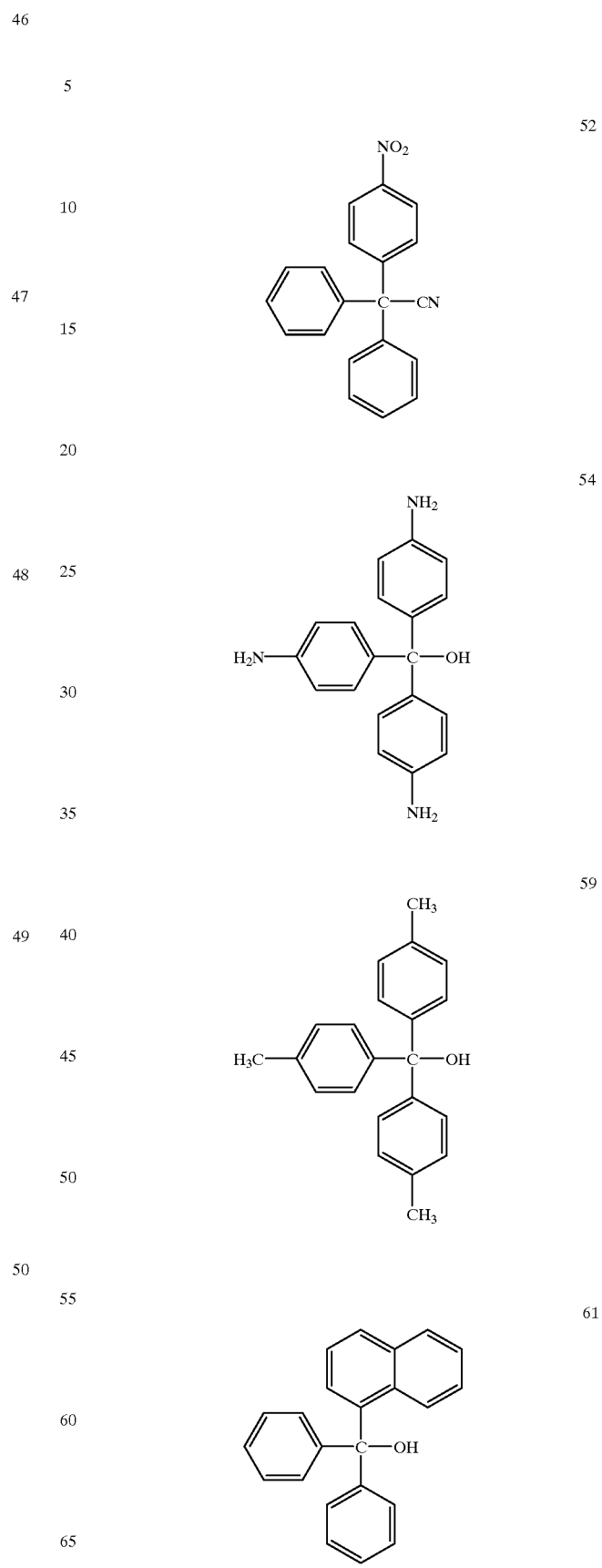

65
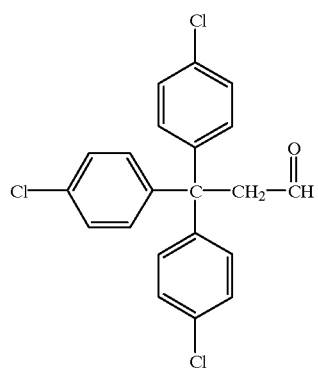
67
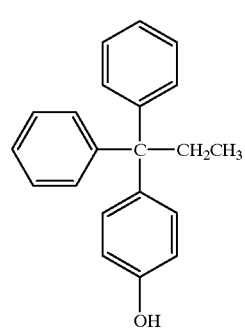
68
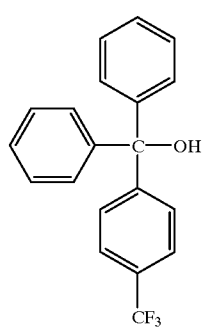
70
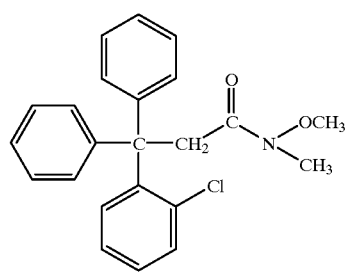
71
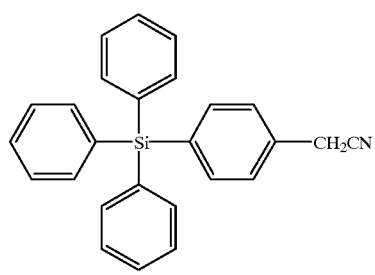
72
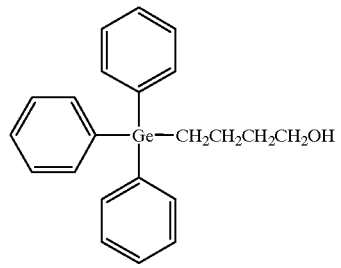
73
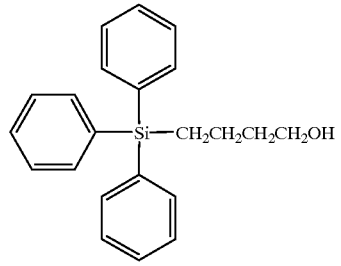
79
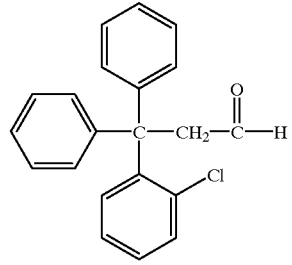
82
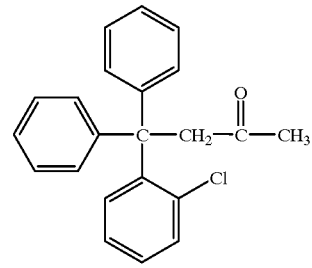
83
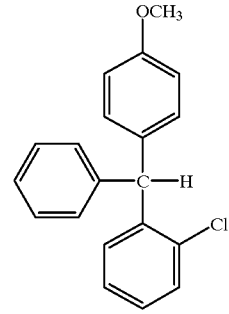

-continued
84
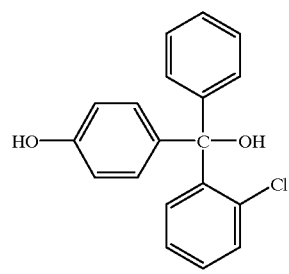
85
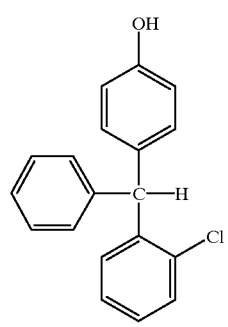
86
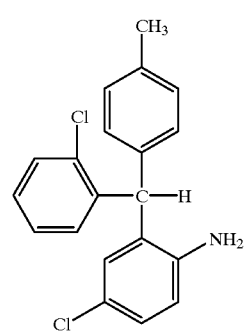
89
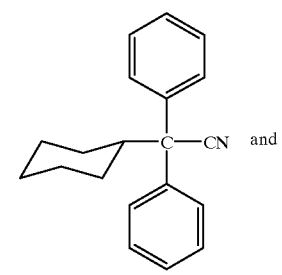 and
90
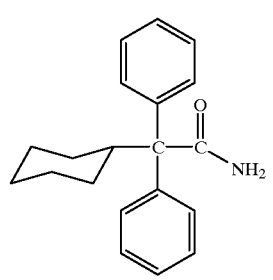
16
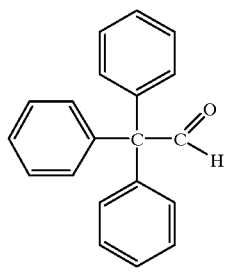
28
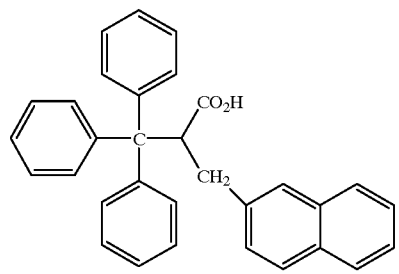
30
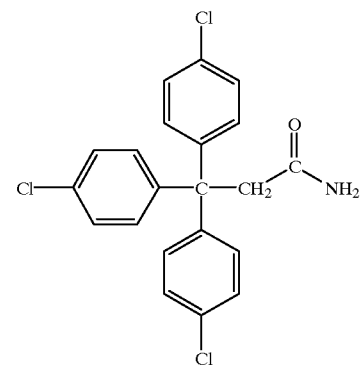
36
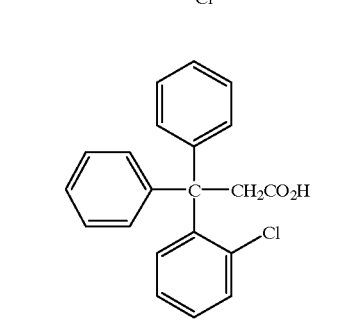
43
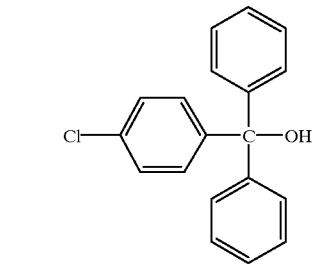
38. The method of claim 37, wherein said compound is selected from the group consisting of compounds

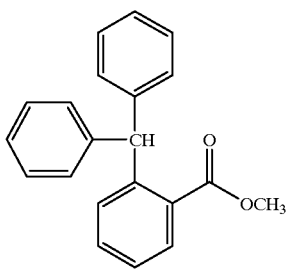

45

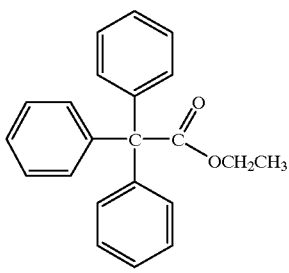

47

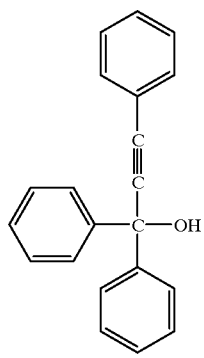

48

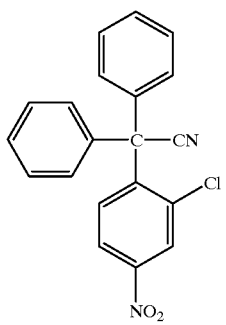

49

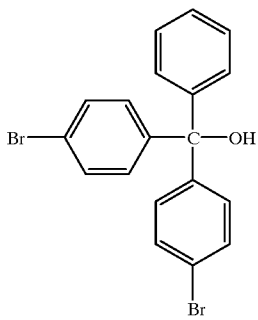

50

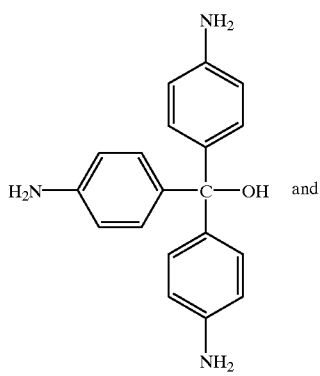

54

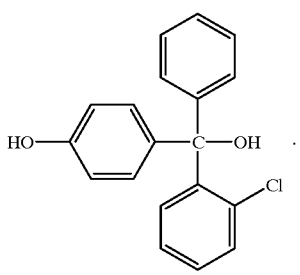

84

39. The method of claim 36, wherein said disease characterized by abnormal cell proliferation is cancer, a blood vessel proliferative disorder, a fibrotic disorder or an arteriosclerotic condition.

40. The method of claim 39, wherein said administration of said compound is per oral, parenteral or intravenous.

41. The method of claim 36, wherein said disease characterized by abnormal cell proliferation is a dermatological disease or Kaposi's sarcoma and said administration is transdermal.

42. The method of claim 41, wherein said dermatological disease is selected from the group consisting of keloids, hypertonic scars, seborrheic dermatosis, papilloma virus infection, eczema and actinic keratosis.

* * * * *

UNITED STATES PATENT AND TRADEMARK OFFICE
CERTIFICATE OF CORRECTION

PATENT NO. : 6,028,103
DATED : FEBRUARY 22, 2000
INVENTOR(S) : FALGUNI M. KHER, CARLO BRUGNARA, MARK FROIMOWITZ, JOHN J. CLIFFORD, YING-DUO GAO, EUGENE W. KELLEHER, YESH P. SACHDEVA, MINGHUA SUN, HEATHER N. TAFT, JOSE HALPERIN, ADEL M. MOUSSA, EMILE M. BELLOTT, JR., REEM M. HAIDAR AND RICHARD JOHN LOMBARDY

It is certified that error appears in the above-identified patent and that said Letters Patent is hereby corrected as shown below:

[73] Assignees: Children's Medical Center Corporation, Boston Mass.; NuChem Pharmaceuticals Inc., Scarborough, Ontario, Canada; President & Fellows of Harvard College, Cambridge, Mass.

Signed and Sealed this

Twenty-seventh Day of March, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

| | | |
|---|---|---|
| PATENT NO. | : 6,028,103 | Page 1 of 1 |
| APPLICATION NO. | : 08/822550 | |
| DATED | : February 22, 2000 | |
| INVENTOR(S) | : Brugnara et al. | |

It is certified that error appears in the above-identified patent and that said Letters Patent is hereby corrected as shown below:

Please add the following to Section 63:

[63] --Continuation-in-part of application No. 08/618,762, March 20, 1996, and a continuation-in-part of application No. 618,759, March 20, 1996, each is a continuation-in-part of application No. 08/307,887, September 16, 1994.--

Signed and Sealed this

Third Day of October, 2006

JON W. DUDAS
*Director of the United States Patent and Trademark Office*